(12) United States Patent
Miklatzky et al.

(10) Patent No.: US 10,806,234 B2
(45) Date of Patent: Oct. 20, 2020

(54) APPARATUS AND METHOD FOR ANALYZING HAIR AND/OR PREDICTING AN OUTCOME OF A HAIR-COLORING TREATMENT

(71) Applicant: COLORIGHT LTD., Rehovot (IL)

(72) Inventors: Efraim Miklatzky, Neve Ilan (IL); Daniel Mandelik, Rehovot (IL); Gilad Davara, Rehovot (IL); Eliyahu Benny, Rishon-LeZion (IL); Oded Livneh, Holon (IL); Tal Marcu, Mevaseret Zion (IL); Thierry Wasserman, Tel Aviv (IL)

(73) Assignee: COLORIGHT LTD., Rehovot (IL)

( * ) Notice: Subject to any disclaimer, the term of this patent is extended or adjusted under 35 U.S.C. 154(b) by 906 days.

(21) Appl. No.: 15/303,727

(22) PCT Filed: Mar. 25, 2015

(86) PCT No.: PCT/IB2015/000724
§ 371 (c)(1),
(2) Date: Oct. 12, 2016

(87) PCT Pub. No.: WO2015/166340
PCT Pub. Date: Nov. 5, 2015

(65) Prior Publication Data
US 2017/0156476 A1 Jun. 8, 2017

Related U.S. Application Data
(63) Continuation-in-part of application No. PCT/IL2014/050850, filed on Sep. 28, 2014.
(Continued)

(30) Foreign Application Priority Data
Sep. 24, 2014 (WO) .................. PCT/IB2014/064809

(51) Int. Cl.
*A45D 44/00* (2006.01)
*G01J 3/50* (2006.01)
(Continued)

(52) U.S. Cl.
CPC .......... *A45D 44/005* (2013.01); *A61B 5/1032* (2013.01); *A61B 5/448* (2013.01);
(Continued)

(58) Field of Classification Search
None
See application file for complete search history.

(56) References Cited

U.S. PATENT DOCUMENTS 4,643,313 A 2/1987 Robson
5,205,837 A 4/1993 Andrean et al.
(Continued)

FOREIGN PATENT DOCUMENTS

CA 2828363 A1 3/2015
CN 1665444 A 9/2005
(Continued)

OTHER PUBLICATIONS

European Office Action dated Mar. 5, 2018 in Patent Application No. 15 729 219.4, 5 pages.
(Continued)

*Primary Examiner* — Shawn Decenzo
(74) *Attorney, Agent, or Firm* — Oblon, McClelland, Maier & Neustadt, L.L.P.

(57) ABSTRACT

The present disclosure relates to devices and methods for analyzing hair and/or predicting an outcome of hair-coloring treatment. disclosed is method of predicting a result of a hair-color-modifying treatment on a sample of hair, the method comprising: a. for each given region of a plurality of distinct regions, respectively measuring a region-specific spectrum of respective material of the hair-sample respec-
(Continued)

tively disposed within the given region; and b. computing first and second predicted post-treatment spectra respectively from first and second initial spectra by respectively predicting a transformation of the first and second initial spectra following subjecting the sample of hair to the hair-color-modifying treatment, the first and second initial spectra being distinct and (i) derived from the plurality of measured region-specific spectra and/or (ii) corresponding to first and second of the measured region-specific spectra.

18 Claims, 41 Drawing Sheets

Related U.S. Application Data

(60) Provisional application No. 62/106,426, filed on Jan. 22, 2015, provisional application No. 61/985,331, filed on Apr. 28, 2014, provisional application No. 61/984,798, filed on Apr. 27, 2014, provisional application No. 61/984,861, filed on Apr. 27, 2014.

(51) Int. Cl.
| | |
|---|---|
| *G01J 3/02* | (2006.01) |
| *A61B 5/103* | (2006.01) |
| *A61B 5/00* | (2006.01) |
| *G01J 3/46* | (2006.01) |
| *G01N 21/84* | (2006.01) |
| *B01F 13/10* | (2006.01) |
| *G01N 21/25* | (2006.01) |
| *G01N 21/31* | (2006.01) |
| *G01N 21/01* | (2006.01) |

(52) U.S. Cl.
CPC ...... *B01F 13/1055* (2013.01); *B01F 13/1058* (2013.01); *B01F 13/1063* (2013.01); *G01J 3/0272* (2013.01); *G01J 3/463* (2013.01); *G01J 3/50* (2013.01); *G01N 21/01* (2013.01); *G01N 21/25* (2013.01); *G01N 21/31* (2013.01); *G01N 21/84* (2013.01); *A45D 2044/007* (2013.01); *A61B 5/0075* (2013.01); *A61B 5/4848* (2013.01)

(56) References Cited

U.S. PATENT DOCUMENTS

| | | | |
|---|---|---|---|
| 5,660,342 A | 8/1997 | Bock | |
| 5,754,283 A | 5/1998 | Keane et al. | |
| 5,851,181 A | 12/1998 | Talmor | |
| 5,990,058 A | 11/1999 | Bac et al. | |
| 6,096,359 A | 8/2000 | Bombardelli et al. | |
| 6,170,980 B1 | 1/2001 | Martin | |
| 6,248,749 B1 | 6/2001 | Demarchez et al. | |
| 6,330,341 B1* | 12/2001 | Macfarlane ......... A45D 44/005 132/202 | |
| 6,362,885 B1 | 3/2002 | Osumi et al. | |
| 6,529,446 B1 | 3/2003 | De | |
| 6,547,833 B2 | 4/2003 | Casperson et al. | |
| 6,613,311 B2 | 9/2003 | Imperial | |
| 6,707,929 B2 | 3/2004 | Marapane et al. | |
| 6,764,523 B2 | 7/2004 | Casperson et al. | |
| 6,790,240 B2 | 9/2004 | Schulze Zur Wiesche et al. | |
| 6,807,297 B1* | 10/2004 | Tankovich ......... A45D 44/005 382/100 | |
| 6,818,022 B2 | 11/2004 | Massoni | |
| 6,984,377 B2 | 1/2006 | Withiam et al. | |
| 7,110,117 B2 | 9/2006 | Grossinger et al. | |
| 7,204,856 B2 | 4/2007 | Schulze Zur Wiesche et al. | |
| 7,304,739 B2 | 12/2007 | Grossinger et al. | |
| 7,458,992 B2 | 12/2008 | Schmenger et al. | |
| 7,463,356 B2 | 12/2008 | Grossinger et al. | |
| 7,508,508 B2 | 3/2009 | Grossinger et al. | |
| 7,523,018 B2 | 4/2009 | Grossinger et al. | |
| 7,708,021 B2 | 5/2010 | Ghannad et al. | |
| 2001/0002025 A1 | 5/2001 | Rolf-Dieter et al. | |
| 2002/0010556 A1 | 1/2002 | Marapane et al. | |
| 2002/0157191 A1 | 10/2002 | Casperson et al. | |
| 2002/0194684 A1 | 12/2002 | Wiesche et al. | |
| 2003/0028978 A1 | 2/2003 | Schulze Zur Wiesche et al. | |
| 2004/0000015 A1* | 1/2004 | Grossinger ......... A45D 44/005 8/405 | |
| 2004/0013616 A1 | 1/2004 | Withiam et al. | |
| 2005/0015895 A1 | 1/2005 | Azizova et al. | |
| 2005/0019398 A1 | 1/2005 | Kotharl et al. | |
| 2005/0036677 A1* | 2/2005 | Ladjevardi ......... G01N 21/84 382/162 | |
| 2005/0039271 A1 | 2/2005 | Schulze Zur Wiesche et al. | |
| 2005/0165705 A1* | 7/2005 | Lauper ......... B01F 13/1055 705/500 | |
| 2005/0177032 A1 | 8/2005 | Grossinger et al. | |
| 2005/0244343 A1 | 11/2005 | Withiam et al. | |
| 2006/0149151 A1* | 7/2006 | Ladjevardi ......... A61B 5/0059 600/475 | |
| 2006/0195300 A1 | 8/2006 | Grossinger et al. | |
| 2007/0159290 A1* | 7/2007 | Grossinger ......... A45D 44/005 336/215 | |
| 2007/0265867 A1 | 11/2007 | Lin | |
| 2008/0013077 A1 | 1/2008 | Orelli et al. | |
| 2008/0068604 A1 | 3/2008 | Grossinger et al. | |
| 2008/0256724 A1 | 10/2008 | Bolton et al. | |
| 2009/0119852 A1 | 5/2009 | Marsh | |
| 2011/0038818 A1 | 2/2011 | Onyebuagu et al. | |
| 2012/0320191 A1* | 12/2012 | Meschkat ......... G01N 21/84 348/135 | |
| 2014/0082854 A1 | 3/2014 | Landa et al. | |
| 2014/0118521 A1* | 5/2014 | Conti ......... G01J 3/0202 348/77 | |
| 2015/0089751 A1* | 4/2015 | Landa ......... B65D 1/0223 8/406 | |
| 2016/0209272 A1* | 7/2016 | Miklatzky ......... A45D 44/005 | |

FOREIGN PATENT DOCUMENTS

| | | |
|---|---|---|
| CN | 101394764 A | 3/2009 |
| CN | 103635176 A | 3/2014 |
| DE | 3609962 A1 | 6/1987 |
| DE | 4205112 A1 | 8/1993 |
| DE | 10260880 A1 | 7/2004 |
| DE | 102006008149 A1 | 8/2007 |
| EP | 0590538 A1 | 4/1994 |
| EP | 1817976 A1 | 8/2007 |
| EP | 2081668 A1 | 7/2009 |
| EP | 2133673 A1 | 12/2009 |
| EP | 2193781 A1 | 6/2010 |
| FR | 2402446 A1 | 4/1979 |
| FR | 2532174 A1 | 3/1984 |
| FR | 2901131 A1 | 11/2007 |
| JP | 2000116622 A | 4/2000 |
| JP | 2000-227360 A | 8/2000 |
| JP | 2004198398 A | 7/2004 |
| JP | 2004212088 A | 7/2004 |
| JP | 2007212140 A | 8/2007 |
| JP | 2008-539441 A | 11/2008 |
| JP | 2008285429 A | 11/2008 |
| JP | 2009-522585 A | 6/2009 |
| KR | 100802645 A | 9/2004 |
| KR | 20040076861 A | 9/2004 |
| WO | 0145647 A2 | 6/2001 |
| WO | 02083282 A1 | 10/2002 |
| WO | 03012728 A1 | 2/2003 |
| WO | 03074015 A1 | 9/2003 |
| WO | WO 2004/002300 A2 | 1/2004 |
| WO | 2004058202 A1 | 7/2004 |
| WO | 2004082650 A1 | 9/2004 |
| WO | 2004101689 A2 | 11/2004 |
| WO | 2008046518 A1 | 4/2008 |
| WO | 2009121643 A2 | 10/2009 |
| WO | 2009152033 A1 | 12/2009 |
| WO | 2010004565 A2 | 1/2010 |

(56) References Cited

FOREIGN PATENT DOCUMENTS

| WO | 2010060601 A1 | 6/2010 |
| WO | 2010100231 A1 | 9/2010 |
| WO | 11003554 A2 | 1/2011 |
| WO | 2012032671 A1 | 3/2012 |
| WO | 2012127429 A1 | 9/2012 |

OTHER PUBLICATIONS

European Office Action dated May 24, 2019 in European Patent Application No. 15729219.4, 5 pages.
Korean Office Action dated Mar. 19, 2018 in Patent Application No. 10-2016-7031811 (with English translation), 8 pages.
Birngruber C et al: The color(s) of human hair-Forensic hair analysis with SpectraCube; vol. 185, No. 1-3, Mar. 10, 2009, pp. e19-e23; Forensic Science International, Elsevier Scientific Publishers Ireland Ltd, IE; available online Jan. 24, 2009.
WO 2008046518 Machine Translation (by EPO and Google); published on Apr. 24, 2008 Beiersdorf AG et al.
DE 10260880 Machine Translation (by EPO and Google); published on Jul. 1, 2004, Henkel KGAA.
DE 3609962 Machine Translation (by EPO and Google); published on Jun. 19, 1987, Panke Hartmut.
DE 4205112 Machine Translation (by EPO and Google); published on Aug. 26, 1993, Brackmann Hans Peter Dr Med.
EP 2081668 Machine Translation (by EPO and Google); published on Jul. 29, 2009, Beiersdorf AG.
WO 2009121643 Machine Translation (by EPO and Google); published on Oct. 8, 2009, Henkel AG & CO KGAA et al.
FR 2402446 Machine Translation (by EPO and Google); published on Apr. 6, 1979, Oreal.
FR 2532174 Machine Translation (by EPO and Google); published on Mar. 2, 1984, Bristol Myers Co.
FR 2901131 Machine Translation (by EPO and Google); published on Nov. 23, 2007, Oreal.
International Search Report for PCT/IB2015/000724; search report dated Nov. 16, 2015.
International Search Report for PCT/IB2015/053065; search report dated Sep. 1, 2015.
International Search Report for PCT/IL2014/50850; search report dated Mar. 23, 2015.
JP 2000116622 Machine Translation (by EPO and Google); published on Apr. 25, 2000, Kose Corp.
JP 2004198398 Machine Translation (by EPO and Google); published on Jul. 15, 2004, Kose Corp.
JP 2004212088 Machine Translation (by EPO and Google); published on Jul. 29, 2004, Kose Corp.
JP 2007212140 Machine Translation (by EPO and Google); published on Aug. 23, 2007, Kose Corp.
JP 2008285429 Machine Translation (by EPO and Google); published on Nov. 27, 2008, Shiseido Co Ltd.
KR100802645 Machine Translation (by EPO and Google); published on Sep. 3, 2004.
KR20040076861 Machine Translation (by EPO and Google); published on Sep. 3, 2004.
WO 0145647 Machine Translation (by EPO and Google); published on Jun. 28, 2001, Henkel KGAA et al.
WO 03074015 Machine Translation (by EPO and Google); published on Sep. 12, 2003, Henkel KGAA et al.
WO 2004082650 Machine Translation (by EPO and Google); published on Sep. 3, 2004, Henkel KGAA et al.
Written Opinion for PCT/IB2015/000724; written opinion dated Nov. 16, 2015.
Written Opinion for PCT/IB2015/053065; written opinion dated Sep. 1, 2015.
Written Opinion for PCT/IL2014/50850; written opinion dated Mar. 23, 2015.
DE 102006008149 Machine Translation (by EPO and Google); published on Aug. 23, 2007, Henkel KGAA.
Office Action dated Dec. 21, 2018 in Korean Patent Application No. 10-2016-7031811 (with English language translation).
Mexican Office Action dated Feb. 14, 2019 in Patent Application No. MX/A/2016/013960, 3 pages.
Japanese Office Action dated Nov. 27, 2018 in Japanese Patent Appplication No. 2016-584995 (with unedited computer generated English translation), 9 pages.
Mexican Office Action dated Jul. 5, 2018 in Mexican Patent Application No. MX/A/2016/013960, 4 pages.
Combined Chinese Office Action and Search Report dated Dec. 25, 2019, in Patent Application No. 201580022937.1 (with English translation), 15 pages.
Japanese Office Action dated Oct. 1, 2019, in Patent Application No. 2016-564995, 6 pages (with unedited computer generated English translation).
Office Action dated Apr. 30, 2020 in Brazilian Application No. BR112016025101-6 (w/English translation).

* cited by examiner

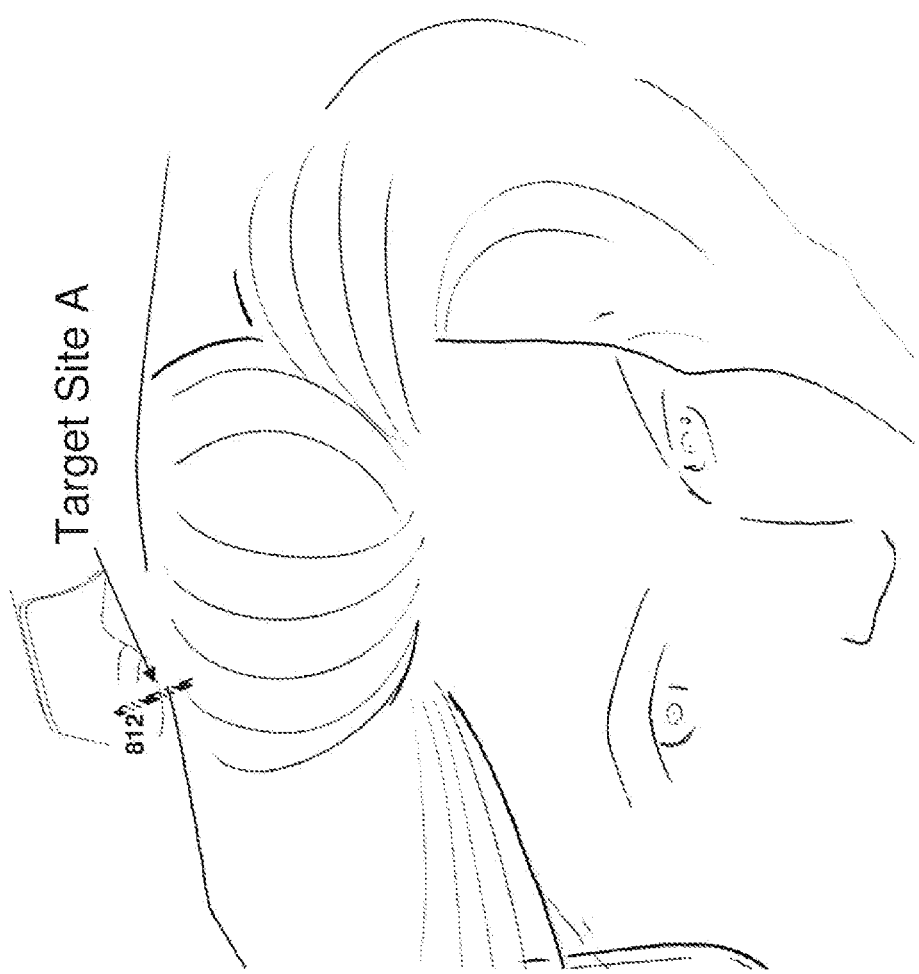

APPARATUS AND METHOD FOR ANALYZING HAIR AND/OR PREDICTING AN OUTCOME OF A HAIR-COLORING TREATMENT

CROSS-REFERENCE TO RELATED APPLICATIONS

This application is a National Stage of PCT/IB2015/000724 filed Mar. 25, 2015, which claims the benefit of U.S. Provisional Application Nos. 61/984,798 filed Apr. 27, 2014, 61/984,861 filed Apr. 27, 2014, 61/985,331 filed Apr. 28, 2014 and 62/106,426 filed Jan. 22, 2015, which claims the benefit of priority from PCT/IB2014/064809 filed Sep. 24, 2014 and PCT/IL2014/050850 filed Sep. 28, 2014, the entire contents of each of which are incorporated herein by reference.

BACKGROUND

Embodiments of the present invention relate to methods and apparatus for analyzing "natural gray hair"—e.g. in order to provide a customized hair-coloring composition suitable for the natural gray hair.

For a significant segment of the population, as people age, their hair grays, and their hair becomes 'natural gray.' 'Natural gray hair' may be distinguished from 'artificial gray' hair, where a presence of artificial colorant gives individual hair-shafts their gray color.

Natural gray hair is a mixture of two types of hair-shafts: (i) natural-pigment-containing hair shafts (e.g. melanin-containing hair shafts such as black shafts or red shafts or blond shafts or brown shafts or other natural-pigment-containing shafts) and (ii) natural white hair shafts which are substantially melanin-free e.g. due to age. The presence of both color-types of hair-shafts within a single hair-mixture causes the mixture as a whole to appear as 'gray hair' to the casual naked-eye viewer.

For the present disclosure, the term 'shaft' refers to an individual hair and is not limited to the 'shaft portion' (i.e. away from the root portion) of an individual hair.

Natural gray hair is one example, but not the only example, of a shaft-color-heterogeneous 'mixture' of hair-shafts also referred to herein as 'a color-heterogeneous mixture of hair.'

Sometimes, natural gray hair is subjected to a 'hair-coloring treatment' which may change the overall appearance so it is no longer considered 'natural gray.' For the present disclosure, a 'hair-coloring treatment' is any treatment which modifies the color of hair shafts. Examples of hair-coloring treatments include hair-dying treatments (e.g. based upon artificial colorants) and bleaching. Hair-dying treatments include temporary, demi-permanent, semi-permanent or permanent hair-dying (e.g. oxidative hair-dying) treatments.

For the present disclosure, 'formerly natural gray hair' is mixture of hair that (i) in the past was "natural gray" but has been transformed by a hair-coloring treatment and (ii) is presently recognizable (e.g. upon inspection by a hair-stylist or other skilled artisan) to have properties indicative of its former status as naturally grey hair. In one example, a mixture of natural black and natural white hair-shafts (i.e. one type of natural gray hair) is artificially dyed red—e.g. by an oxidative hair-dying process.

In this example, as a result of the red hair-dye treatment, each natural white hair-shaft becomes a relatively light shade of red, while each natural black hair shaft become a darker shade of red—this is observable upon close inspections of the individual hair shafts. In contrast, the overall appearance of the mixture (i.e. as whole) differs from that of the individual shafts (i.e. viewed in isolation).

In this example, before treatment with the red dye, the hair is natural-gray and is a mixture of natural-black and natural white hair-shafts. After the hair-dying process, the hair is 'formerly-natural-gray' and is a mixture of hair-shafts of first and second color-types. The hair shafts of the first color type are the shafts that, before the dying process, are natural black—after the dying process, these hair-shafts are dark red. The hair shafts of the second color type are the shafts that, before the dying process, are natural white—after the dying process, these hair-shafts are light red.

Hair-coloring has been practiced for millennia, and continues to play an important in modern society. A central problem in the art of hair-coloring is to provide the correct treatment—e.g. the appropriate hair-coloring composition and/or treatment parameters (e.g. treatment time, temperature, etc).

PCT/IB2012/051351 discloses a dispensing device comprising a plurality of containers, where each container contains a different respective ingredient for a hair-coloring composition. An initial spectrum of the hair is measured and analyzed. In accordance with the results of the analysis, a combination of ingredients for a customized hair-coloring composition (i.e. specific to the user's hair and a desired result to be achieved) is dispensed from the containers by a dispensing device.

The combination of ingredients for the hair-coloring composition is selected according to analysis of a measured hair-spectrum. Therefore, it is highly desirable to accurately measure the initial spectrum of the hair-sample, in order to provide the customized hair-coloring best suited to the user's hair and his/her hair-coloring goals.

To date, there is an ongoing need for apparatus and methods of ascertaining a current status of a user's hair—e.g. for the purpose of accurately dispensing the correct combination of ingredients for a hair-coloring composition.

SUMMARY

Embodiments of the present invention relate to methods and apparatus for predicting a result of hair-color-modifying treatment on a sample of natural-gray hair (i.e. a mixture of natural-pigment-containing shafts and natural-white shafts) based upon measuring and analyzing region-specific spectra.

In some embodiments, (i) a region-specific spectra of hair material within a first region of the sample is measured and (ii) a region-specific spectra of hair material within a second region of the sample is measured.

In contrast to a sample-representative spectrum (i.e. generated from light scattered from locations throughout the sample), the measured region-specific spectra corresponding to the first region is generated primarily from light scattered from natural-white shaft(s). In contrast to the sample-representative spectrum, the measured region-specific spectra corresponding to the second region is generated primarily from light scattered from natural-pigment-containing shaft(s).

Based upon the first and second region-specific spectra, it is possible to respectively predict a post-treatment state (i.e. after subjecting the sample of hair-color-modifying treatment) of the natural-white and natural-pigment-containing shaft(s) by respectively computing first and second post-treatment predicted spectra.

Subsequently, in order to predict a post-treatment state representative of the entire sample of hair, the first and second post-treatment spectra may be combined with each other—e.g. in a manner that taking into account relative fractions of natural white and natural-pigment-containing shafts within the sample. Thus, in hair samples where natural white shafts are more common, a greater weight may be assigned to a predicted spectrum representing a post-treatment state of the natural white shafts. Conversely, in hair samples where natural-pigment-containing shafts are more common, a greater weight may be assigned to a predicted spectrum representing a post-treatment state of the natural-pigment-containing shafts.

Not wishing to be bound by theory, it is noted that different shaft types may respond differently to the same hair-coloring treatment. In situations where the sample of hair is relatively homogeneous, there is no need to compute region-specific spectra. In these situations, a single spectra, generated by light scattered from locations throughout the sample, may suffice to characterize a 'typical' hair-shaft within the sample.

In contrast, for samples of natural-gray hair there is no 'typical' hair-shaft-instead, hair-shafts are either natural white or natural-pigment-containing shafts, each of which responds differently to the hair treatment. In order to accurately predict a sample-representative post-treatment spectrum, it may therefore be necessary to predict the final spectrum for each type of hair-shaft, and to combine the results.

However, in order to accurately predict the final spectrum for each type of hair-shaft, the initial hair-spectrum of each type of hair-shaft should be accurately characterized. Towards this end, methods and apparatus are now disclosed where the initial hair-spectrum of each type of hair-shaft is directly measured by performing region-specific spectral measurement for specific regions within the hair-sample.

The preceding paragraphs relate to the specific example of natural gray hair. As will be discussed below, other embodiments relate to formerly natural gray hair.

Thus, without limitation on the specifics on the hair-sample, a region-specific spectrum may be respectively measured for a each given region of plurality of regions. Each region-specific spectrum is specific to material of the hair-sample within the given region.

The aforementioned teachings may be implemented using a variety of devices for measuring spectra, including but not limited to a hyperspectral imaging device and device comprising color-dispersion optics (e.g. prism or grating) for breaking light into spectral components.

Alternatively or additionally, a configuration is disclosed where (i) the spectrum-measurement device defines an object-plane; (ii) the hair is disposed so that the object-plane passes through each given region of the plurality of regions to define, for each given region, a respective "region-object-plane intersection-area" of the given region; (iii) for each of the given regions, (A) the respective region-object-plane intersection-area has an elongated shape and an aspect ratio of at least 5 (or at least 10 or at least 15) to define an 'elongate axis' and/or a respective width of the respective region-object-plane intersection-area is at most 100 microns or at most 50 microns or at most 25 microns or at most 15 microns.

In this way, when the hair shafts of the sample are aligned with each other to define a hair-shaft elongate axis, and the elongate axis of the respective region-object-plane intersection-area is aligned with that of the hair shafts of the sample, the region-object-plane intersection-area is adapted to a shape of hair-shafts.

Not wishing to be bound by theory, in situations where the hair-sample is homogeneous with respect to shaft color, it is, in general, not problematic if material of multiple shafts is "captured" by a single measure spectrum. In contrast, in other situations (e.g. where the sample is natural gray hair or formerly natural gray hair), there is a need to avoid this as much as possible, without resorting to unnecessarily restricting the region size.

Without limiting the scope of claimed subject-matter, it is noted that by employing an optical arrangement and device geometry which adapts the region-object-plane intersection-area to the shape of hair-shafts, it is possible to accomplish this goal.

A method of optically acquiring data from keratinous fiber(s) comprises: a. illuminating the keratinous fiber(s) such that light reflected and/or deflected and/or transmitted by the fiber(s) is incident upon a detector and converted into electrical signal(s) by the detector; and b. computing, from electrical signal(s), a plurality of spectra of the keratinous fiber(s) such that each spectrum of the plurality of spectra respectively corresponds to (i) a different respective portion of the keratinous fiber(s) and/or (ii) material within a different sub-region of space within which at least a portion of the keratinous fiber(s) are disposed.

In some embodiments, the method is performed so that i. the illuminated fiber(s) are in a first object plane; ii. a first image is formed at an intermediate location along an optical path between the fiber(s) and the detector(s), the intermediate location being configured both as a first image plane and a second object plane, the first image being an at least 1D-focused image of the fiber(s); and iii. a second image is formed at the detector, the second image being an image of the first image.

In some embodiments the method is performed so that due to a presence of at least one imaging system(s): i. the illuminated fiber(s) are in a first object plane; ii. a first image is formed at an intermediate location along an optical path between the fiber(s) and the detector(s), the intermediate location being configured both as a first image plane and a second object plane, the first image being an at least 1D-focused image of the fiber(s); and iii. a second image is formed at the detector, the second image being an image of the first image.

In some embodiments, the image system(s) are disposed along the optical path.

In some embodiments, a slit or aperture is disposed along the optical path between the keratinous fiber(s) and the detector(s) and the intermediate location substantially corresponds to the slit or aperture.

In some embodiments, the detector comprises a plurality of constitutive photodetectors arranged in a two-dimensional planar array, a plane of which corresponds to an image plane of the second image.

In some embodiments, first and second sub-sets (e.g. disjoint sub-sets) of the constitutive photodetectors respectively generate first reflection and second spectra that respectively correspond (i) to first and second portions of the keratinous fibers and/or (ii) material within a first and second subs-region of space within which at least a portion of the keratinous fiber(s) are disposed.

In some embodiments, in one direction the sub-sets of photodetectors are parallel to each other.

In some embodiments, the illuminated fibers are aligned with one another along an alignment axis and the first and second portions of the fibers corresponding to the first and second spectra are aligned with each other along the alignment axis.

In some embodiments, a first direction of the array of photodetectors corresponds to varying wavelength and a second direction perpendicular to the first direction corresponds to different portions of the keratinous fibers.

In some embodiments, each reflection spectrum of the plurality of spectra respectively corresponds to a different respective disjoint portion of the keratinous fibers.

In some embodiments, the method further comprises: c. electronically comparing a spectrum specific to a first of the portions of the keratinous fiber(s) with a spectrum specific to the second of the portions of the keratinous fiber(s); and d. in accordance with the results of the comparison, classifying the keratinous fiber(s) as homogeneous or heterogeneous with respect to color.

In some embodiments, the method further comprises: c. electronically comparing a reflection spectrum specific to a first of the portions of the keratinous fiber(s) with a reflection spectrum specific to the second of the portions of the keratinous fiber(s); and d. in accordance with the results of the comparison, classifying the keratinous fiber(s) as homogeneous or heterogeneous with respect to color.

In some embodiments, the method further comprises: c. electronically comparing a spectrum specific to a first of the portions of the keratinous fiber(s) with a spectrum specific to the second of the portions of the keratinous fiber(s); and d. dispensing a combination of hair-coloring agents according to the results of the comparing.

In some embodiments, the method further comprises: c. electronically comparing a reflection spectrum specific to a first of the portions of the keratinous fiber(s) with a reflection spectrum specific to the second of the portions of the keratinous fiber(s); and d. dispensing a combination of hair-coloring agents according to the results of the comparing.

A fiber-coloring-related method comprises: a. disposing keratinous fibers of a subject so that a different portion of the fiber(s) is respectively located in a different sub-region of a region of space divided into a plurality of sub-regions; b. for each sub-region of the plurality, respectively acquiring spectral data specific to the respective portion of the keratinous fibers disposed within the sub-region; and c. electronically comparing spectral data specific to a first of the portions of the keratinous fiber(s) with spectral data specific to the second of the portions of the keratinous fiber(s).

A fiber-coloring-related method comprises: a. disposing keratinous fibers of a subject so that a different portion of the fiber(s) is respectively located in a different sub-region of a region of space divided into a plurality of sub-regions; b. for each sub-region of the plurality, measuring a respective spectrum specific to the respective portion of the keratinous fibers disposed within the sub-region; and c. electronically comparing a first of the spectra descriptive of a first portion of the fiber(s) with a second of the spectra of descriptive of a second portion of the fiber(s).

In some embodiments, one or both of the first and second spectra are reflection spectra.

In some embodiments, the method is performed to compute a uniformity and/or homogeneity parameter.

In some embodiments, the uniformity and/or homogeneity parameter is a hair-strand uniformity and/or homogeneity parameter.

In some embodiments, the uniformity and/or homogeneity parameter is a color-space parameter.

In some embodiments, the color-space parameter is a LAB color-space value.

In some embodiments, the method further comprises in accordance with the results of the comparing, dispensing a combination of hair-coloring agents.

In some embodiments, the method further comprises: classifying the keratinous fiber(s) as homogeneous or heterogeneous with respect to color and/or color-space value, wherein the dispensing is performed in accordance with the results of the classifying.

In some embodiments, the method further comprises: classifying the keratinous fiber(s) as homogeneous or heterogeneous with respect to color and/or color-space value.

A method of coloring keratinous fibers comprises: a. disposing keratinous fibers of a subject so that a different fiber(s) sub-population is respectively located in each sub-region of a region of space divided into a plurality of sub-regions; b. for each of the sub-regions, respectively acquiring spectral data specific to the respective sub-population of the keratinous fibers disposed within the sub-region; c. electronically comparing spectral data specific to a first of the sub-populations with spectral data specific to the second of the sub-populations; and d. computing a parameter related to hair homogeneity in accordance with the results of the electronic comparing.

In some embodiments, (i) the method further comprises: e. in accordance with the comparing of the spectral data, electronically classifying the keratinous fibers as natural-grey hair or as artificially colored grey hair; and the dispensing is performed in accordance with the results of the classifying.

In some embodiments, the image is anisotropically magnified at different magnification values in orthogonal axes in the image plane—i.e. a first magnification value which may be equal to one or to any other value; i.e. a second magnification value which is different from the first t magnification value in the second axis.

In some embodiments, the method is performed so that the image plane that is co-planar with the slit or aperture is an image plane containing a only-1D-focused-image that is focused in a first axis within the image plane and blurred in a second axis that is orthogonal to the first axis.

A system for acquiring spectral data from keratinous fiber(s) comprises: a. a device housing defining a fiber(s)-placement location; b. a source light configured to illuminate keratinous fiber(s) when situated at the fiber-placement location so that at least a portion of the fiber(s) is situated within a region of space; c. apparatus configured for each of the sub-regions, to respectively acquire spectral data specific to the material disposed within each sub-region.

A system for acquiring spectral data from keratinous fiber(s) comprises: a. a device housing defining a fiber(s)-placement location; b. a source light configured to illuminate keratinous fiber(s) when situated at the fiber-placement location so that at least a portion of the fiber(s) is situated within a region of space; c. apparatus configured for each of the sub-regions, to respectively acquire spectral data specific to a different portion of the keratinous fiber(s).

In some embodiments, the apparatus comprises a monochromator or spectral analyzer.

In some embodiments, the monochromator or spectral analyzer comprises at least one of a grating and a prism.

In some embodiments, a slit or aperture is disposed upon an optical path between the fiber(s) and a light detector.

A system for acquiring spectral data from keratinous fiber(s) comprises: a. a device housing defining a fiber(s)-placement location; b. a source of light configured to illuminate keratinous fibers when situated at the fiber-placement location; c. a slit or aperture or collimating lens; d. a grating and/or prism and/or other color-dispersion optics; e. a detector for detecting light; and f. first and second optical systems configured to focus light reflected and/or deflected and/or transmitted by the illuminated keratinous fibers so that: i. light reflected and/or deflected and/or transmitted by the keratinous fiber(s) is focused by the first imaging system to form an at least 1D-focused image of the keratinous fiber(s) at an intermediate location along an optical path between the fiber(s) and the detector; and ii. the grating and/or prism and/or other color-dispersion optics and the second optical system are situated on an optical path between the slit or aperture or collimating lens and the detector such that the light reflected from and/or deflected by and/or transmitted by the keratinous fibers reaches the detector via the grating and/or prism and/or other color-dispersion optics and the second optical system, wherein: A. a presence of the grating and/or prism and/or other color-dispersion optics causes the detector to detect spectral data of the keratinous fiber(s); and B. a presence of the second imaging system focuses keratinous-fiber(s)-reflected and/or deflected and/or transmitted light on the detector (e.g. on a planar array thereof) to form, on the detector, an image of the keratinous fiber(s) at the intermediate location(s). This image may be In some embodiments, the intermediate location(s) may correspond to a location of the slit (or other aperture) or to a location of the grating and/or prism and/or other color-dispersion optics.

A system for acquiring spectral data from keratinous fiber(s) comprises: a. a device housing defining a fiber(s)-placement location; b. a light source configured to illuminate keratinous fibers when situated at the fiber-placement location; c. a 2D planar array of photodetectors; and d. optical components configured to form, from light reflected and/or deflected and/or transmitted by the fiber(s): i. spectral data in a first dimension of the 2D planar array of photodetectors; and ii. an at least 1D-focused image of the keratinous fibers in a second direction of the 2D planar array of photodetectors, the second direction being perpendicular to the first direction.

In some embodiments, the slit defines an elongate axis and the keratinous fibers(s) are substantially aligned in a direction that is perpendicular to the elongate axis of the slit.

A method of optically acquiring data from keratinous fiber(s) comprises: a. illuminating the fiber(s) by light such that light reflected by the fiber(s) subsequently passes through a slit or aperture; and b. analyzing the output of photodetector(s) to (i) determine spectral data of the illuminated fiber(s) and/or (ii) calculate a hair treatment from the analyzed output, wherein the illuminated fiber(s) are in an object plane and a presence of one or more optical components on an optical path between the fiber(s) and the slit or aperture cause the formation of an image plane so that the slit or aperture is located within the image plane.

In some embodiments, the image is anisotropically magnified at different magnification values in orthogonal axes in the image plane—i.e. a first magnification value which may be equal to one or to any other value; i.e. a second magnification value which is different from the first magnification value in the second axis.

In some embodiments, the image plane that is co-planar with the slit or aperture is an image plane containing a only-1 D-focused-image that is focused in a first axis within the image plane and blurred in a second axis that is within the image plane and is orthogonal to the first axis.

A method of optically acquiring data from keratinous fiber(s) comprises: a. illuminating the fiber(s) by light such that light reflected by the fiber(s) subsequently passes through a slit or aperture; and b. analyzing the output of photodetector(s) to (i) determine spectral data of the illuminated fiber(s) and/or (ii) calculate a hair treatment from the analyzed output, wherein the illuminated fiber(s) are in an object plane and a presence of one or more optical components on an optical path between the fiber(s) and the slit or aperture cause the formation first and second only-1D-focused-images on opposite sides of the slit or aperture and wherein light from both the first and second only-1D-focused-images is incident upon and detected by the photodetector(s) (e.g. to re-combine the only-1D-focused-image.

In some embodiments, the first only-1D-focused-image is focused in a first direction and blurred in a second direction orthogonal to the first direction, and the second only-1D-focused-image is focused in the second direction and blurred in the first direction.

In some embodiments, the illuminated fibers are aligned with each other.

In some embodiments, at least one of the spectrum(s), or at least a plurality of spectrum(a) are reflection spectrum(a) or absorption spectrum(a) or transmission spectrum(a).

In some embodiments, the keratinous fiber(s) are illuminated by incoherent light.

A method of optically acquiring data from keratinous fiber(s) comprises: a. illuminating the keratinous fiber(s); b. from light reflected and/or deflected and/or transmitted by the fiber(s), respectively forming first and second only-1D-focused images of the fiber(s) at first and second intermediate locations; c. passing from light of the first and second only-1D-focused images through color-dispersion optics; and d. receiving, by a light detector, light from the first and second only-1D-focused images after this light has passed through the color-dispersion optics so as to detect spectrum (a) of the keratinous fiber(s).

In some embodiments, the first and second only-1D-focused images are formed are formed by optical components comprising a toric lens.

A system for optically acquiring data from keratinous fiber(s), the system comprising: a. a source of light configured to illuminate the keratinous fiber(s); b. an imaging system configured to respectively form, from light reflected and/or deflected and/or transmitted by the fiber(s), first and second only-1D-focused images of the fiber(s) at first and second intermediate locations; c. color-dispersion optics configured to receive light of the first and second only-1D-focused images; and d. by a light detector configured to receive light from the first and second only-1D-focused images after this light has passed through the color-dispersion optics so as to detect spectrum(a) of the keratinous fiber(s).

In some embodiments, the first only-1D-image is focused in a first image-plane direction and blurred in a second image-plane direction orthogonal to the first image-plane direction and the second only-1D-image is focused in the second image-plane direction and blurred in the first image-plane direction.

In some embodiments, the keratinous fiber(s) are aligned along an alignment axis.

In some embodiments, i. the keratinous fiber(s) are aligned along an alignment axis; ii. the first only-1D-image is focused in a first image-plane direction along the alignment axis and blurred in a second image-plane direction orthogonal to the first image-plane direction; and iii. the second only-1D-image is focused in the second image-plane direction and blurred in the first image-plane direction.

In some embodiments, the first and second only-1D-focused images are recombined at the light detector.

In some embodiments, the first and second only-1D-focused images are recombined into a 2D-focused-image at the light detector.

In some embodiments, the reflected and/or deflected and/or transmitted by the fiber(s) passes through an aperture or a slit en route to the color-dispersion optics.

In some embodiments, an image plane location of the first or second only-1D-focused image corresponds to a plane of slit or the aperture.

In some embodiments, further comprising according to the detected spectrum(a), calculating a hair-treatment recipe and/or dispensing a combination of hair-coloring agents.

A method of predicting a result of a hair-color-modifying treatment on a sample of hair, the method comprising: a. for each given region of a plurality of distinct regions, respectively measuring a region-specific spectrum of respective material of the hair-sample respectively disposed within the given region; and b. computing first and second predicted post-treatment spectra respectively from first and second initial spectra by respectively predicting a transformation of the first and second initial spectra following subjecting the sample of hair to the hair-color-modifying treatment, the first and second initial spectra being distinct and (i) derived from the plurality of measured region-specific spectra and/or (ii) corresponding to first and second of the measured region-specific spectra.

In some embodiments, the method wherein: i. the hair-sample is a sample of natural-gray hair that is a mixture of natural white shafts and natural-pigment-containing shafts; ii. each measured region-specific spectrum of a first set of the measured region-specific spectra is generated primarily by light scattered from natural white shaft(s); iii. each measured region-specific spectrum of a second set of the measured region-specific spectra is generated primarily by light scattered from natural-pigment-containing shaft(s); iv. the first and second initial spectra are respectively representative of the first and second set of spectra and are respectively derived therefrom.

Examples of natural-pigment-containing shafts include natural-black shafts, natural-brown shafts, natural-red shafts and natural-blond shafts.

In some embodiments, the method i. the hair-sample is a sample of formerly natural-gray hair that: (A) was formerly mixture of natural white shafts and natural-pigment-containing shafts; and (B) is presently a mixture of shafts of first and second color-types that are respectively derived from the natural white and the natural-pigmented-containing shafts; ii. each measured region-specific spectrum of a first set of the measured region-specific spectra is generated primarily by light scattered from shaft(s) of the first color-type; iii. each measured region-specific spectrum of a second set of the measured region-specific spectra is generated primarily by light scattered from shaft(s) of the second color-type; and iv. the first and second initial spectra are respectively representative of the first and second set of spectra and are respectively derived therefrom.

In some embodiments, the method of any preceding claim, further comprising: [computing from the first and second post-treatment spectra, a predicted sample-representative post-treatment spectrum representing the predicted spectrum for the entire sample of hair after subjecting to the hair-color-modifying treatment.

In one example, the post-treatment spectrum may be computed so as to reduce a distance in color space between hair shafts of the first and second color type (e.g. natural white and natural-pigment-containing shafts) and also to minimize a distance in color space between hair-shafts of each type and a target color (e.g. LAB value).

In some embodiments, the method wherein (i) the predicted sample-representative post-treatment spectrum is further computed in accordance with a hair-shaft color-heterogeneity parameter of the hair-sample and/or (ii) multiple region-specific spectra are compared to each other, and the predicted sample-representative post-treatment spectrum is computed according to the results of the comparing of the region-specific spectra.

In some embodiments, the method wherein the hair-shaft color-heterogeneity parameter describes relative fractions of natural white shafts and natural-pigmented shafts within a sample of natural gray hair.

In some embodiments, a different predicted sample-representative post-treatment spectrum is respectively computed for each candidate hair-color-modifying treatment of a plurality of candidate hair-color-modifying treatments, and wherein a recommended hair-color-modifying treatment is obtained upon comparing predictions for each of the candidate hair-color-modifying treatments.

In some embodiments, the method further comprising computing a combination of ingredients for a hair-coloring composition in accordance with the sample-representative post-treatment spectrum, and dispensing the computed combination of ingredients.

In some embodiments, the method wherein step (b) is performed respectively for each candidate hair-color-modifying treatment of a plurality of candidate hair-color-modifying treatments, and wherein a recommended hair-color-modifying treatment is obtained upon comparing predictions for each of the candidate hair-color-modifying treatments.

In some embodiments, the method further comprising computing in a combination of ingredients for a hair-coloring composition in accordance with the predicted post-treatment spectra computed in step (b).

In some embodiments, the measured spectra are reflection spectra or transmission spectra or absorption spectra.

In some embodiments, the method wherein the measuring of the spectra is performed by a spectral imaging device (e.g. hyperspectral imaging)

In some embodiments, the method wherein the measuring of the spectra includes passing light reflected and/or deflected and/or transmitted by hair(s) of the sample through a prism or a grating.

In some embodiments, the method wherein each measured spectrum includes at least one reading in the [200 nm, 400 nm] range and/or at least one reading in the [400 nm, 600 nm] range and/or or at least one reading in the [600 nm, 800 nm] range.

In some embodiments, the method wherein each measured spectrum includes at least one reading in the [600+N*50 nm, 1000 (nm] range, wherein N is an integer having a value of at least 1 or at least 2 or at least 3 or at least 4 or at least 5.

In some embodiments, the method wherein each measurement spectrum includes at least one reading in all of the following ranges: {[400 nm, 500 nm], [500 nm, 600 nm], [600 nm, 700 nm], [700 nm, 800 nm]}.

In some embodiments, the method wherein each measurement spectrum includes at least one reading in all of the following ranges: {[400 nm, 500 nm], [500 nm, 600 nm], [600 nm, 700 nm], [800 nm, 1000 nm]}.

In some embodiments: i. each region-specific spectrum measurement is performed by a measurement device defining an object plane; ii. the sample hair is disposed so that the object plane passes through each of the regions; iii. the perpendicular projection of each region into the object plane yields a respective elongated area of the object-plane defining an elongate axis; iv. each elongated area defined by the projection of a respective region into the object plane has a respective aspect ratio equal to at least 5 or at least 10 and/or a respective width of each elongated area of the object plane is at most 100 microns or at most 50 microns or at most 25 microns or most 15 microns; and v. all of the elongated axes are aligned with each other.

In some embodiments, the method performed on a sample of hair-shafts that are aligned with each other to define an hair-alignment-axis, the hair-alignment axis being aligned with each of the elongate axes of the region-object-plane intersection areas.

In some embodiments, a method of predicting a result of a hair-color-modifying treatment on a sample of hair, the method comprising: a. for each given region of a plurality of distinct regions, respectively performing a region-specific colorimetric measurement of respective material of the hair-sample disposed within the given region to respectively acquire colorimetric measurement data specific to material respectively disposed in the given region; b. computing first and second predicted post-treatment colorimetric data respectively from first and second initial colorimetric data by respectively predicting a transformation of the first and second initial colorimetric data following subjecting the sample of hair to the hair-color-modifying treatment, the first and second initial colorimetric data being distinct and (i) derived from the plurality of region-specific colorimetric measurement data and/or (ii) corresponding to first and second of the region-specific colorimetric data.

In some embodiments, the method wherein: i. the hair-sample is a sample of natural-gray hair that is a mixture of natural white shafts and natural-pigment-containing shafts; ii. each colorimetric measurement of a first set of the colorimetric measurements is generated primarily by light scattered from natural white shaft(s); iii. each colorimetric measurement of a second set of the colorimetric measurements is generated primarily by light scattered from natural-pigment-containing shaft(s); iv. the first initial colorimetric data is representative of the colorimetric measurement data acquired by measurements of the first set of colorimetric measurements; and v. the second initial colorimetric data is representative of the colorimetric measurement data acquired by measurements of the second set of colorimetric measurements.

In some embodiments, i. the hair-sample is a sample of formerly natural-gray hair that: (A) was formerly a mixture of natural white shafts and natural-pigment-containing shafts; and (B) is presently a mixture of shafts of first and second color-types that are respectively derived from the natural white and the natural-pigmented-containing shafts; ii. each colorimetric measurement of a first set of the colorimetric measurements is generated primarily by light scattered from shaft(s) of the first color-type; iii. each colorimetric measurement of a second set of the colorimetric measurements is generated primarily by light scattered from shaft(s) of the second color-type, iv. the first initial colorimetric data is representative of the colorimetric measurement data acquired by measurements of the first set of colorimetric measurements; and v. the second initial colorimetric data is representative of the colorimetric measurement data acquired by measurements of the second set of colorimetric measurements:

In some embodiments: i. each region-specific colorimetric measurement is performed by a measurement device defining an object plane; ii. the sample hair is disposed so that the object plane passes through each of the regions: iii. the perpendicular projection of each region into the object plane yields a respective elongated area of the object-plane defining an elongate axis; iv. each elongated area defined by the projection of a respective region into the object plane has a respective aspect ratio equal to at least 5 or at least 10 and/or a respective width of each elongated area of the object plane is at most 100 microns or at most 50 microns or at most 25 microns or most 15 microns; and v. all of the elongated axes are aligned with each other.

In some embodiments, the method performed on a sample of hair-shafts that are aligned with each other to define an hair-alignment-axis, the hair-alignment axis being aligned with each of the elongate axes of the region-object-plane intersection areas.

In some embodiments, the method further comprising: computing from the first and second post-treatment colorimetric data, a predicted sample-representative post-treatment colorimetric data representing the predicted colorimetric data for the entire sample of hair after subjecting to the hair-color-modifying treatment.

In some embodiments, the method wherein (i) the predicted sample-representative post-treatment colorimetric data is further computed in accordance with a hair-shaft color-heterogeneity parameter of the hair-sample and/or (ii) multiple region-specific colorimetric data are compared to each other, and the predicted sample-representative post-treatment colorimetric data is computed according to the results of the comparing of the region-specific colorimetric data.

In some embodiments, the method wherein the hair-shaft color-heterogeneity parameter describes relative fractions of natural white shafts and natural-pigmented shafts within a sample of natural gray hair.

In some embodiments, the method wherein a different predicted sample-representative post-treatment colorimetric data is respectively computed for each candidate hair-color-modifying treatment of a plurality of candidate hair-color-modifying treatments, and wherein a recommended hair-color-modifying treatment is obtained upon comparing predictions for each of the candidate hair-color-modifying treatments.

In some embodiments, the method further comprising computing a combination of ingredients for a hair-coloring composition in accordance with the sample-representative post-treatment colorimetric data, and dispensing the computed combination of ingredients.

In some embodiments, the method wherein the region-specific colorimetric data is LAB data or RBG data.

In some embodiments, the method wherein: i. each of the region-specific spectrum measurements is performed by a measurement device defining object and image planes; ii. each of the region-specific spectra is generated by light which is optically processed so that: A. along each given line of a set of parallel lines in the image plane, only light from a corresponding line of a set of parallel lines in the object plane reaches the given line in the image plane; and/or B. for each given point along each given line of the set of parallel lines in the image plane, light of only a single wavelength from multiple locations along the corresponding line in the object plane reaches the given point of the given line; and/or C. along each given line of the set of parallel lines in the image plane, the wavelength of light received from the object plane monotonically increases.

In some embodiments, the method wherein, for each of the region-specific colorimetric measurements is based upon light processed by optics defining an object plane and an image plane such that i. along each given line of a set of parallel lines in the image plane, only light from a corresponding line of a set of parallel lines in the object plane reaches the given line in the image plane; and/or ii. for each given point along each given line of the set of parallel lines in the image plane, light of only a single wavelength from multiple locations along the corresponding line in the object plane reaches the given point of the given line; and/or iii. along each given line of the set of parallel lines in the image plane, the wavelength of light received from the object plane monotonically increases.

A method of optically acquiring data from a sample of hair by a measurement device defining object and image planes, the method comprising: a. disposing the hair sample so that the object plane passes through the sample of hair; and b. optically processing light reflected and/or deflected and/or transmitted by hair of the sample of that, upon reaching the image plane: i. along each given line of a set of parallel lines in the image plane, only light from a corresponding line of a set of parallel lines in the object plane reaches the given line in the image plane; ii. for each given point along each given line of the set of parallel lines in the image plane, light of only a single wavelength from multiple locations along the corresponding line in the object plane reaches the given point of the given line; and iii. along each given line of the set of parallel lines in the image plane, the wavelength of light received from the object plane monotonically increases.

In some embodiments, the processed light is received by an array of photodetectors to detect one or more spectrum(a) the sample of hair or of a portion thereof.

In some embodiments, performed to measure spectra as follows: for each given region of a plurality of regions, a respective region-specific spectrum of respective material of the hair-sample respectively disposed within the given region is measured.

In some embodiments, i. the sample hair is disposed so that the object plane passes through each of the regions; ii. the perpendicular projection of each region into the object plane yields a respective elongated area of the object-plane defining an elongate axis; iii. each elongated area defined by the projection of a respective region into the object plane has a respective aspect ratio equal to at least 5 or at least 10 and/or a respective width of each elongated area of the object plane is at most 100 microns or at most 50 microns or at most 25 microns or most 15 microns; and iv. all of the elongated axes are aligned with each other.

In some embodiments, performed on a sample of hair-shafts that are aligned with each other to define an hair-alignment-axis, the hair-alignment axis being aligned with each of the elongate axes of the elongated areas.

A method of optically acquiring data from a sample of hair by a measurement device defining object and image planes, the method comprising: for each given region of a plurality of regions, respectively measuring a region-specific spectrum of respective material of the hair-sample respectively disposed within the given region, wherein: i. the sample hair is disposed so that the object plane passes through each of the regions; ii. the perpendicular projection of each region into the object plane yields a respective elongated area of the object-plane defining an elongate axis; iii. each elongated area defined by the projection of a respective region into the object plane has a respective aspect ratio equal to at least 5 or at least 10 and/or a respective width of each elongated area of the object plane is at most 100 microns or at most 50 microns or at most 25 microns or most 15 microns; and iv. all of the elongated axes are aligned with each other.

In some embodiments, the method wherein the measurements are performed when hair shafts of the sample of hair are aligned with each other to define a hair-shaft alignment axis that is aligned with all of the elongate axes of the elongated area of the object planes.

In some embodiments, the method performed such that a thickness of each elongated area of the object plane is at most 100 microns or at most 50 microns.

In some embodiments, the method wherein the spectrum are generated by light which is (i) reflected and/or deflected and/or transmitted by hair of the sample and (ii) subsequently optically processed so that, upon reaching the image plane: i. along each given line of a set of parallel lines in the image plane, only light from a corresponding line of a set of parallel lines in the object plane reaches the given line in the image plane; and ii. for each given point along each given line of the set of parallel lines in the image plane, light of only a single wavelength from multiple locations along the corresponding line in the object plane reaches the given point of the given line; and iii. along each given line of the set of parallel lines in the image plane, the wavelength of light received from the object plane monotonically increases.

In some embodiments, the method wherein light for the measurement of the region-dependent spectra is processed by color-dispersion optics, and the spectrum is generated by the color-dispersion-optics-processed light.

In some embodiments, the method wherein, performed on a sample of gray hair, or on a sample of formerly gray hair.

In some embodiments, the method further comprising measuring, obtaining or computing a hair heterogeneity parameter and computing a hair-coloring treatment and/or dispensing ingredients for a hair-coloring composition according to the results of the hair heterogeneity parameter (e.g. the combination of the hair heterogeneity parameter and the optically acquired data and/or the measured region-specific spectra—for example, the results of analyzing the measured region-specific spectra).

In some embodiments, the method further comprising (i) directly or indirectly comparing first and second of the region-specific spectra and (ii) computing a hair-coloring treatment and/or dispensing ingredients for a hair-coloring composition according to the results of the comparing (e.g. the combination of the results of the comparing and the optically acquired data and/or the measured region-specific spectra—for example, the results of analyzing the measured region-specific spectra).

In some embodiments, the method further comprising (i) detecting locations of hair-shaft boundaries and (ii) computing a hair-coloring treatment and/or dispensing ingredients for a hair-coloring composition according to the results of the detecting of the hair-shaft boundaries. (e.g. the combination of the results of the detecting the hair-shaft boundaries and the optically acquired data and/or the measured region-specific spectra—for example, the results of analyzing the measured region-specific spectra).

In some embodiments, a method of computing a spectral data related to a plurality of keratinous fiber(s), the method comprising: a. illuminating keratinous fiber(s) on a user's head; b. detecting light from the illuminated fibers to one acquire user spectral measurement-data; c. computing a scalp-spectrum-similarity-parameter by measuring an extent of a correlation between (i) the user-spectral-measurement-data and (ii) one or more portions of a scalp spectrum; and d. contingent upon a similarity exceeding a threshold, generating an alert signal.

In some embodiments, a method of computing a reflection spectrum related to a plurality of keratinous fiber(s), the method comprising: a. subjecting keratinous fiber(s) on a user's head to one or more spectral measurements to acquire user-spectral-data; b. analyzing the user-spectral-data to determine a presence or an extent of a presence of one or more scalp-spectrum recognition feature(s) within the user-spectral-data; and c. contingent upon the results of the determining, generating an alert signal.

In some embodiments, a method of computing a reflection spectrum related to a plurality of keratinous fiber(s), the method comprising: a. subjecting keratinous fiber(s) on a user's head to one or more spectral measurements to acquire user-spectral-data; b. analyzing the user-spectral-data to determine a compute a likelihood that the user-spectral data is indicative of scalp-spectrum(a) rather than hair-spectrum (a); and c. contingent upon the results of the determining, generating an alert signal.

In some embodiments, a method comprising: a. subjecting keratinous fiber(s) on a subject's head to one or more spectral measurements to acquire subject-spectral-data; b. subtracting a function of a scalp spectral data from the user-spectral data to obtain scalp-noise-reduced spectral data of keratinous fiber(s) on the user's head; and c. computing a hair-coloring recipe or dispensing hair-coloring agents in accordance with the scalp-noise-reduced spectral data.

In some embodiments, the method wherein the scalp-spectral data is acquired from a person other than the user.

In some embodiments, the method wherein the scalp-spectral data is acquired by subjecting a different section of the subject's head to a spectral measurement.

In some embodiments, a method of reducing scalp-related noise in keratinous fiber spectroscopic data, the method comprising: a. disposing keratinous fibers of a subject so that a different portion of the fiber(s) is respectively located in a different sub-region of a region of space divided into a plurality of sub-regions; b. for each sub-region of the plurality, respectively acquiring spectroscopic data specific to the respective material disposed within the sub-region; and c. computing, from output of the photodetectors from the incident light, a plurality of sub-region-specific reflection spectra that each reflection spectrum of the plurality respectively corresponds to different of the sub-regions; d. analyzing each respective spectrum to determine a respective scalp-spectrum-similarity parameter; e. for a first and a second of the sub-region-specific reflection spectra, each having a different respective non-zero scalp-spectrum-similarity parameter, computing a function of the first and second sub-region-specific reflection spectra to generate a third spectrum having a scalp-spectra-similarity parameter that is less than both that of the first and second sub-region-specific spectra.

In some embodiments, a method of acquiring optical data from keratinous fiber(s), the method comprising: a. disposing keratinous fibers of a subject so that a different portion of the fiber(s) is respectively located in a different sub-region of a region of space divided into a plurality of sub-regions; b. for each sub-region of the plurality, respectively acquiring spectroscopic data specific to the respective material disposed within the sub-region; and c. computing, from output of the photodetectors from the incident light, a plurality of sub-region-specific reflection spectra that each reflection spectrum of the plurality respectively corresponds to different of the sub-regions; d. analyzing each respective spectrum to determine a respective scalp-spectrum-similarity parameter; e. for a first and a second of the sub-region-specific reflection spectra, each having a different respective non-zero scalp-spectrum-similarity parameter, computing a function of the first and second sub-region-specific reflection spectra to generate a third spectrum having a scalp-spectra-similarity parameter that is less than both that of the first and second sub-region-specific spectra.

In some embodiments, a method of acquiring optical data from keratinous fiber(s), the method comprising: a. disposing keratinous fibers of a subject so that a different portion of the fiber(s) is respectively located in a different sub-region of a region of space divided into a plurality of sub-regions; b. for each sub-region of the plurality, respectively acquiring spectroscopic data specific to the respective material disposed within the sub-region; and c. computing, from output of the photodetectors from the incident light, a plurality of sub-region-specific reflection spectra that each reflection spectrum of the plurality respectively corresponds to different of the sub-regions; d. analyzing each respective spectrum to determine a respective scalp-spectrum-similarity parameter, e. in accordance with the results of the analysis, ranking the sub-region-specific reflection spectra; and f. estimating an initial color of the keratinous fiber(s) by assigning a greater weight to the sub-region-specific-reflection ranked to have a lower scalp-spectrum-similarity parameter; and g. in accordance with the estimated initial color and a target color, computing a hair-coloring recipe and/or dispensing ingredients of hair-coloring recipe.

In some embodiments, no region of the plurality is contained within any other region of the plurality.

In some embodiments, all regions of the plurality have the same volume, or wherein for every given region-pair of the set of region-pairs defined by the plurality of regions, a respective volume ratio characterizing the given region-pair is at most 2 or at most 1.5.

In some embodiments, there is no overlap between any two regions of the plurality, or wherein for every given region-pair of the set of region-pairs defined by the plurality of regions, a respective overlap-fraction characterizing the region pair is at most 50%, or at most 30%, of at most 20% or at most 10%.

In some embodiments, the method wherein: i. the measurements are performed by a measurement device defining an object plane: ii. the measurements are performed when the sample of hair is disposed so that the object plane passes through the hair sample to define, for each given region of the plurality of regions, a respective region:object-plane intersection-area, thereby defining a plurality of region-object-plane intersection areas.

In some embodiments, the method wherein no region: object-plane intersection area of the plurality of region-object-plane intersection areas is contained within any other region:object-plane intersection-area of the plurality.

In some embodiments, the method wherein all region: object-plane intersection-areas of the plurality of region: object-plane intersection-areas have the same size, or wherein for every given intersection-area-pair of the set of intersection-area-pairs defined by the plurality of region-object-plane intersection areas, a respective size ratio characterizing the given intersection-area-pair is at most 2 or at most 1.5.

In some embodiments, the method wherein there is no overlap between any two intersection-areas of the plurality of region-object-plane intersection areas. or wherein for every given intersection-area-pair of the set of pairs of intersection-areas defined by the plurality of region-object-plane intersection areas, a respective overlap-fraction characterizing the given intersection-area-pair is at most 50%, or at most 30%, of at most 20% or at most 10%.

Apparatus for predicting a result of a hair-color-modifying treatment on a sample of hair, the apparatus comprising: a. a spectrum-measuring device configured to measure a plurality of spectra as follows: for each given region of a plurality of distinct regions, respectively measuring a region-specific spectrum of respective material of the hair-sample respectively disposed within the given region; and b. electronic circuitry configured to compute first and second predicted post-treatment spectra respectively from first and second initial spectra by respectively predicting a transformation of the first and second initial spectra following subjecting the sample of hair to the hair-color-modifying treatment, the first and second initial spectra being distinct and (i) derived from the plurality of measured region-specific spectra and/or (ii) corresponding to first and second of the measured region-specific spectra.

In some embodiments, the spectrum measuring device includes by color-dispersion optics and/or a hyperspectral device.

Apparatus for predicting a result of a hair-color-modifying treatment on a sample of hair comprises: a. colorimetric-data measuring device configured to measure a colorimetric data as follows: for each given region of a plurality of distinct regions, respectively performing a region-specific colorimetric measurement of respective material of the hair-sample disposed within the given region to respectively acquire colorimetric measurement data specific to material respectively disposed in the given region; b. electronic circuitry configured to compute first and second predicted post-treatment colorimetric data respectively from first and second initial colorimetric data by respectively predicting a transformation of the first and second initial colorimetric data following subjecting the sample of hair to the hair-color-modifying treatment, the first and second initial colorimetric data being distinct and (i) derived from the plurality of region-specific colorimetric measurement data and/or (ii) corresponding to first and second of the region-specific colorimetric data.

In some embodiments, the electronic circuitry includes any combination of software, hardware and firmware.

Apparatus for optically acquiring data from a sample of hair comprising: a. a measurement device comprising optics and a planar array of photodetectors, the optics and the planar array defining object and image planes, the optics configured, when the sample of hair is disposed so the object plane passes through the sample of hair, to optically process light reflected and/or deflected and/or transmitted by hair of the sample of that, upon reaching the image plane: i. along each given line of a set of parallel lines in the image plane, only light from a corresponding line of a set of parallel lines in the object plane reaches the given line in the image plane; ii. for each given point along each given line of the set of parallel lines in the image plane, light of only a single wavelength from multiple locations along the corresponding line in the object plane reaches the given point of the given line; and iii. along each given line of the set of parallel lines in the image plane. the wavelength of light received from the object plane monotonically increases.

In some embodiments, the apparatus is configured to compute from the optically acquired data a hair-coloring treatment and/or configured to dispense ingredients for a hair-coloring composition according to the results of the hair heterogeneity parameter.

In some embodiments, the apparatus is configured to compute the treatment and/or dispense the ingredient according to results of comparing of region-specific spectra and/or according to detected hair-shaft boundaries.

In some embodiments, the apparatus is i. configured to receive, measure, detect, compute and/or obtain a hair heterogeneity parameter; and ii. configured to compute a hair-coloring treatment and/or configured to dispense ingredients for a hair-coloring composition in accordance with both (A) the optically acquired data and/or the measured spectrum(a) and/or the measured colorimetric data and (B) the hair heterogeneity parameter.

In some embodiments, the apparatus is i. configured to detect hair-shaft boundaries: and ii. configured to compute a hair-coloring treatment and/or configured to dispense ingredients for a hair-coloring composition in accordance with both (A) the optically acquired data and/or the measured spectrum(a) and/or the measured colorimetric data and (B) the hair shaft boundaries.

In some embodiments, the apparatus is i. configured to directly or indirectly compare measured spectra; ii. configured to compute a hair-coloring treatment and/or configured to dispense ingredients for a hair-coloring composition in accordance with the results of the comparing.

DETAILED DESCRIPTION OF EMBODIMENTS

Figure 1:
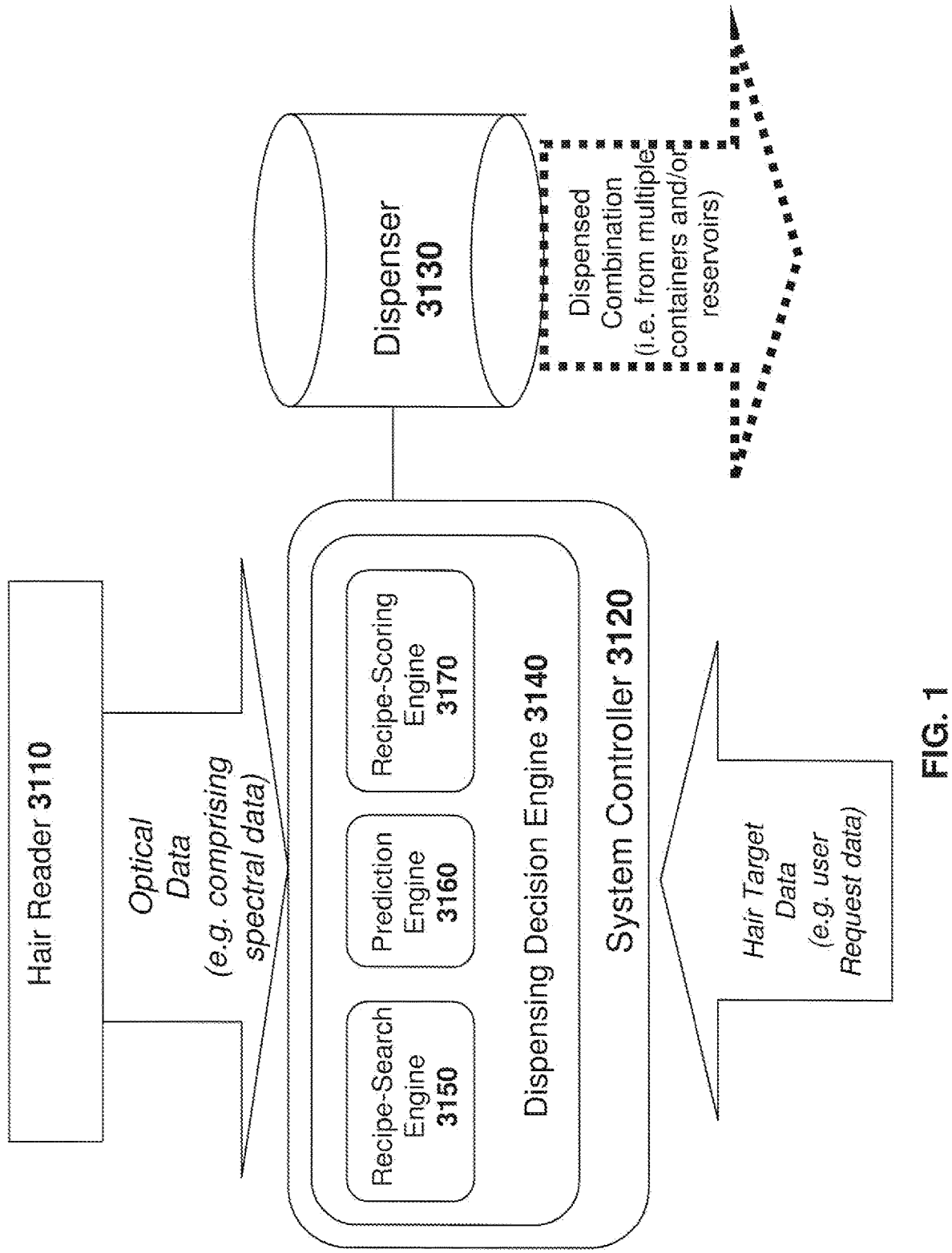
FIG. 1 is a block diagram of a system for preparing a customized hair-coloring composition in accordance with measured optical properties of the user's hair.

The claims below will be better understood by referring to the present detailed description of example embodiments with reference to the figures. The description, embodiments and figures are not to be taken as limiting the scope of the claims. It should be understood that not every feature of the presently disclosed methods and apparatuses is necessary in every implementation. It should also be understood that throughout this disclosure, where a process or method is shown or described, the steps of the method may be performed in any order or simultaneously, unless it is clear from the context that one step depends on another being performed first. As used throughout this application, the word "may" is used in a permissive sense (i.e., meaning "having the potential to"), rather than the mandatory sense (i.e. meaning "must").

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

DEFINITIONS

For convenience, in the context of the description herein, various terms are presented here. To the extent that definitions are provided, explicitly or implicitly, here or elsewhere in this application, such definitions are understood to be consistent with the usage of the defined terms by those of skill in the pertinent art(s). Furthermore, such definitions are to be construed in the broadest possible sense consistent with such usage.

For the present disclosure, an "image" refers to one or more of (i) an image that is focused in both dimensions of an image plane (hereinafter a '2D-focused image') and (ii) an 'only-1D-focused-image' that is focused in only a first dimension of the image plane and blurred in the second dimension of the image plane that is orthogonal to the first dimension. In the context of images, 1D refers to a single dimension (one-dimension) within the image plane and 2D refers to two dimensions within the image plane. The only-1D-focused-image image may be generated using any optics known in the art including but not limited to a toric lens—the skilled artisan will appreciate that other lenses or other optical components other than lenses (e.g. mirrors) may be used. The terms 'partial image' and a 'only-1D-focused-image' are used interchangeably.

An 'at least 1D-focused image' refers to either an 'only-1D-focused-image' or to a 2D-focused image. 'Thus any reference to 'an at least 1D-focused image' means that (i) in some embodiments, the image may be an "only-1D-focused-image" and (ii) in other embodiments, the image may be a '2D-focused image.'

Any reference to an 'image' without specifying the number of dimensions in which the image is focused may relate either to an 'only-1D-focused-image' (in some embodiments) or to a '2D-focused image' (in other embodiments).

When an image is formed at an 'intermediate location' this means that either (i) a 2D-focused image is formed at the intermediate location (e.g. at a single intermediate location); (ii) only one only-1D-focused-image is formed at a single intermediate location or (iii) first and second only-1D-focused-images (i.e. respectively focused in first and second directions (for example, the first and second directions are orthogonal to each other) and respectively blurred in orthogonals to the first and second directions) are formed in first and second intermediate locations. Thus, an 'intermediate location' refers to one or more intermediate locations.

For the present disclosure, 'color-dispersion optics' refers to optical components which breaks light into spectral components. Examples of color-dispersion optics include but are not limited to a prism and a grating.

A "light detector" or a "detector" refers to one or more photodetectors—e.g. configured as an image sensor and/or in a 1D or 2D array of photodetectors. In another example, a scanning detector apparatus equivalent to a 1 D or 2D 'starting' array of photodetectors is used. When light is focused in an image plane at the light detector, the photodetector of the light detector is within the image plane.

A 'slit' is a particular type of aperture having a relatively high aspect ratio (e.g. at least 5 or at least 7.5 or at least 10 or at least 15)—i.e. a length significantly exceeds a width thereof. For the present disclosure, for any embodiment requiring or reciting a 'slit,' an aperture may be substituted.

The term "color-imparting agent" refers to a hair-coloring agent (e.g. for example, for permanent hair-coloring) or to an ingredient thereof.

Unless specified otherwise, when a region is "projected" into a plane, every point of the region is subjected to a perpendicular projection into the plane.

A "substantial majority" means at least 75%. In some embodiments, a 'substantial majority' is at least 90% or at least 95% or at least 99%. Unless specified otherwise, a 'majority' means 'at least a majority.' Unless specified otherwise. 'at least a majority' means that, in some embodiments, the 'majority' is at least a substantial majority—i.e. at least 75% or at least 90% or at least 95% or at least 99%.

Electronic circuitry may include may include any executable code module (i.e. stored on a computer-readable medium) and/or firmware and/or hardware element(s) including but not limited to field programmable logic array (FPLA) element(s), hard-wired logic element(s), field programmable gate array (FPGA) element(s), and application-specific integrated circuit (ASIC) element(s). Any instruction set architecture may be used including but not limited to reduced instruction set computer (RISC) architecture and/or complex instruction set computer (CISC) architecture. Electronic circuitry may be located in a single location or distributed among a plurality of locations where various circuitry elements may be in wired or wireless electronic communication with each other.

A 'hair-coloring treatment' is any treatment which modifies the color of hair shafts. Examples of hair-coloring treatments include hair-dying treatments (e.g. based upon artificial colorants) and bleaching. Examples of hair-dying treatments are temporary, demi-permanent, semi-permanent or permanent hair-dying (e.g. oxidative hair-dying).

A 'spectrum' of material (e.g. hair) may be a reflection spectrum, a transmission spectrum, or an absorption spectrum—i.e. light may be scattered from the material in any modes. A "spectrum" includes readings (i.e. actual measurements) for at least 5 distinct wavelengths—measurements are performed for every wavelength of a set of wavelengths SET=$\{\lambda_1, \lambda_2, \lambda_N\}$ where $\lambda_j > \lambda_i$ if $j > i$, where $N >= 5$.

When a measurement (e.g. a spectra or a measurement of colorometric data) 'corresponds to' a region of space (or of a plane), the measurement is specific to hair-material within that region.

A "set" refers to "one or more." By way of example, a "set of spectrum(a)" is one or more spectrum(a).

Unless other specified, a plurality of regions refers to a plurality of distinct regions.

A 'representative' data-object (e.g. representative colorimetric data, or a representative spectrum) of a set of data objects may be computed by comparing the data objects for common feature (i.e. where the representative is selected on the basis of a common feature), or by computing a central tendency value (e.g. an average, or a median value or any other representative value (e.g., a first statistical moment), or according to any other technique appropriate for the art of hair-analysis.

When second data (e.g. a spectrum or a portion thereof, or colorimetric data) is "derived from" first data, the first data may be obtained by subjecting the first data to analysis and to obtain the second data according to the results of the analysis. For example, the second data may be a mathematical transformation—i.e. second_data=f(first_data). In another example, it is possible to analyze the first data with respect to a database, and to obtain the second data from the first data according to the results of the analysis. By way of example, it is possible (i) to store a library of one of more spectrum(a), (ii) to compare a measured region-specific spectrum(a) to the library-stored spectrum, and to (iii) retrieve one or more spectrum(a) from the library according to the results of the comparing.

One particular example relates to computing a 'representative spectrum' that represents a plurality of measured region-specific spectra. In this particular example, it is possible to store a library of spectra where each spectrum characterizes a different respective hair shade—each of the measured region-specific spectra is compared to the spectra of the libraries to determine common features. According to this particular example, the library-residing spectra having the most common features is designated as the 'representative spectrum' that is representative of the plurality of measured region-specific spectra.

When first and second data-objects (e.g. spectra or colorimetric data) are 'compared' to each other, they are either directly compared, or indirectly compared (e.g. the first and second data-objects may both be directly compared to a third data-object).

An 'initial spectrum' relates to a spectrum before a hair-treatment.

An 'inter-shaft heterogeneity hair parameter,' also referred to as a 'hair heterogeneity parameter, relates to color-property variations (or lack thereof) between individual hair shafts. One example of a 'hair heterogeneity parameter' is the information that a hair sample is 'natural gray hair' or formerly natural gray hair 'or' neither gray hair nor formerly natural gray hair. Another example of a hair heterogeneity parameter is the fact that a particular hair-sample is a mixture of 25% black hair (i.e. a particular shade of black) and 75% white hair.

In different embodiments, a device (e.g. a 'measurement device' for optically acquiring data—for example, to detect one or more spectra and/or to detect colorimetric data) may be said to "define an object plane" and/or to "define an image plane."

When a device 'defines' an 'image plane,' the image plane location is, definition, a location of the planar array of photodetectors When a device 'defines an object plane,' by definition, all of the following features are provided: A. the device comprises 'optics' and a planar array of photodetectors; B. light is received by the planar array of photodetectors and converted into electrical signals—e.g. the colorimetric data and/or spectra(um) may be read, or derived, from the electrical signals C. before reaching the photodetectors, the light is processed by optics en route to the photodetectors. The optics define a relationship between an object plane and an image plane.

By definition, the image plane is co-planar with the photodetectors of the planar array of photodetectors. Since the planar array of photodetectors specifies the location of the image plane, and since the optics specifies the relationship between the image plane and the object plane, a device is said to "define an object plane."

Figure 2:
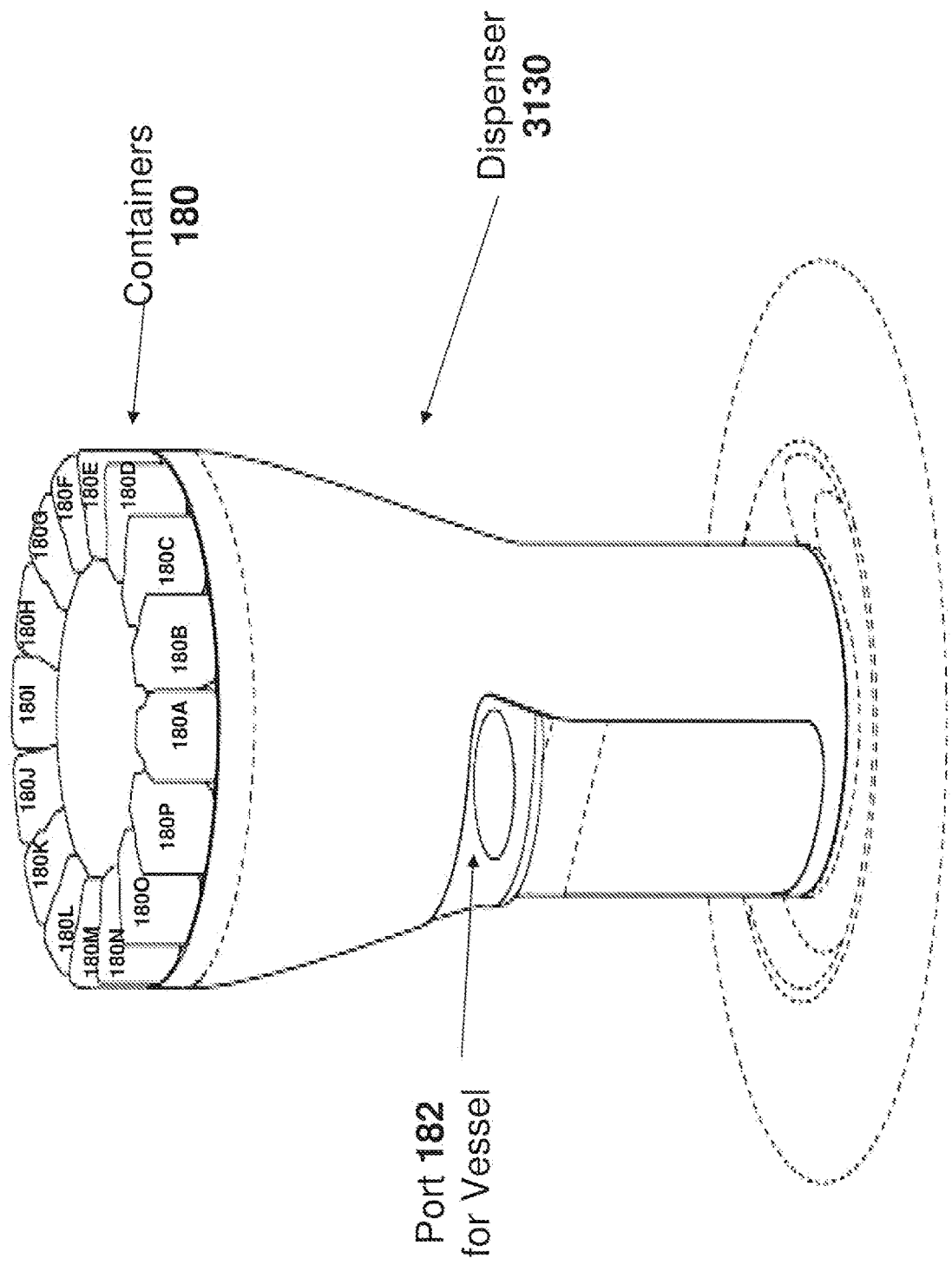
FIGS. 2 and 3A-3B respectively illustrate example dispenser and hair-reader devices.

FIG. 1 is a block diagram of a system for preparing a customized hair-coloring composition in accordance with measured optical properties of the user's hair. FIGS. 2 and 3 respectively illustrate example dispenser and hair-reader devices—e.g. useful in the system of FIG. 1. FIG. 4 is a flow-chart of a routine for preparing a hair-coloring composition—for example, using the system of FIG. 1.

FIGS. 5-27 relate to methods and apparatus for optically acquiring data (e.g. spectral data) from keratinous fiber(s). For example, a plurality of spectra of the keratinous fiber(s) may be detected such that each spectrum corresponds to (i) a different respective portion of the keratinous fiber(s) and/or (ii) material within a different sub-region of space within which at least a portion of the keratinous fiber(s) are disposed.

A Discussion of FIGS. 1-4

FIG. 1 is a block diagram of a system for (i) optically measuring one or properties (e.g. spectra or colorimetric data) of hair and, (ii) in accordance with the optically-measured properties, dispensing material from containers to provide a customized hair-coloring composition. For example, a user desires to color his/her hair to a target shade. An optical measurement of the user's "initial hair" is performed, and a hair-coloring composition, customized according to the initial state of the user's hair as well as the hair-coloring target is prepared.

Illustrated in FIG. 1 are hair reader 3110, system controller 3120, and dispenser device 3130. In the non-limiting example of FIG. 1, system controller 3120 includes dispensing decision engine 3140 which includes recipe-search engine 3150, prediction engine 3160 and recipe-scoring engine 3170.

Hair reader 3110 optically acquires optical data from hair—for example by illuminating the hair and detecting light reflected by and/or transmitted by and/or deflected by the hair. System controller 3120 (e.g. comprising a digital computer) receives both the optical data and hair target data (e.g. describing a target shade desired the user). In accordance with the received data, the system controller 3120 computes (e.g. dispensing decision engine 3140) using a customized recipe for the hair-coloring composition—e.g. including respective quantities of a plurality of different materials stored in dispenser 3110.

The dispenser proceeds to dispense the materials (e.g. into a mixing vessel—NOT SHOWN in FIG. 1) for the hair-coloring composition. These materials may be automatically or manually mixed to form a customized hair-coloring composition, which is applied to the user's hair.

In various examples, the hair-reader 3110 may be or include any one or more (i.e. any combination) of the following: a camera or any other imaging device, a spectrometer (e.g. including 'color-dispersion optics'), a spectrograph, a hyperspectral imaging device. In different examples, a reflection and/or absorption and/or transmission spectrum may be measured.

One non-limiting example of a dispenser 3130 of hair-coloring agents is illustrated in FIG. 2. In this non-limiting example, a plurality of containers 180A-180Q are engaged to dispenser 3130, such that each container contains therein different respective material related to hair-coloring. Dispenser 3130 dispenses a combination of these material into a mixing vessel (NOT SHOWN)—e.g. located in port 182.

In the example of FIG. 1, system controller 3120 includes dispensing decision engine 3140 which computes (a) preferred recipe(s) for dispensing material for the hair-coloring composition. Towards this end, a number of candidate recipes may be considered, selected from a relatively 'large' number of possibilities by receipt-search engine 3150 (For each candidate recipe, the predicted outcome of treating the user's hair according to the candidate recipe may be computed by prediction engine 3160 and scored by scoring engine 3170. For example, scoring engine 3170 may compare the predicted outcome with the hair-target data describing the shade desired by the user.

In one example, one or more of 3140, 3150, 3160, and/or 3170 is implemented as software stored in volatile or non-volatile memory).

Figure 3A:
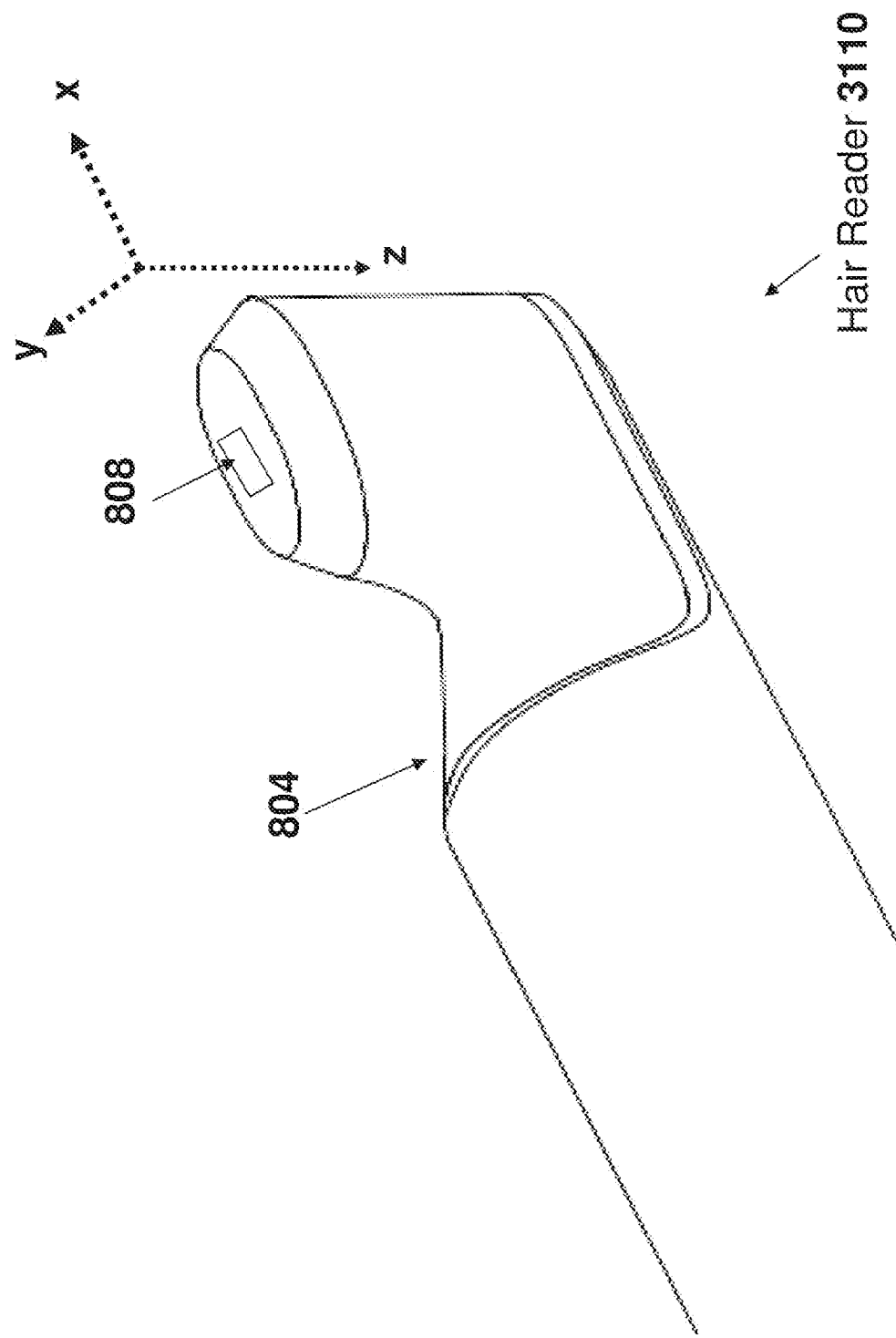
Figure 3B:
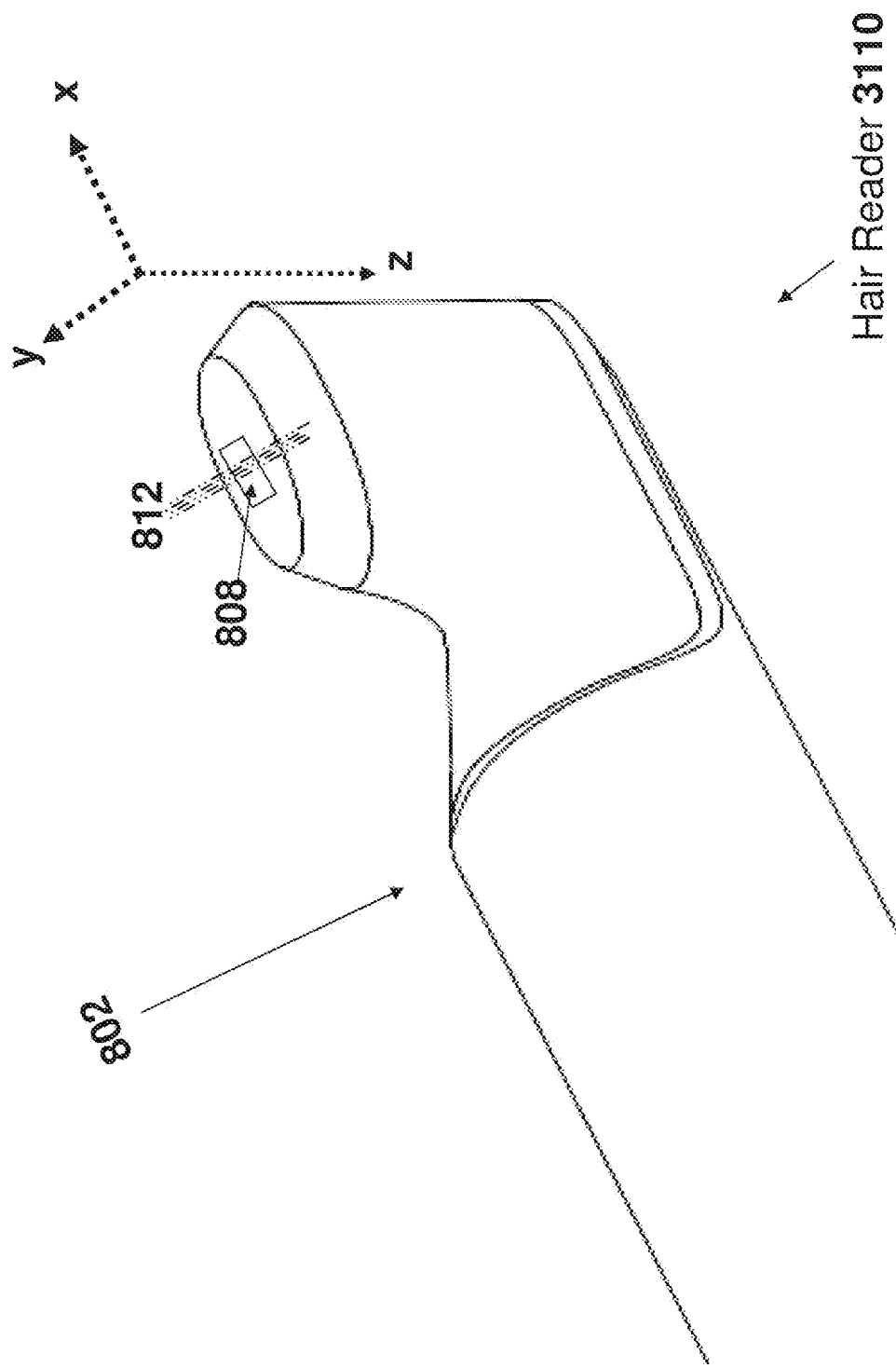
Figure 4:
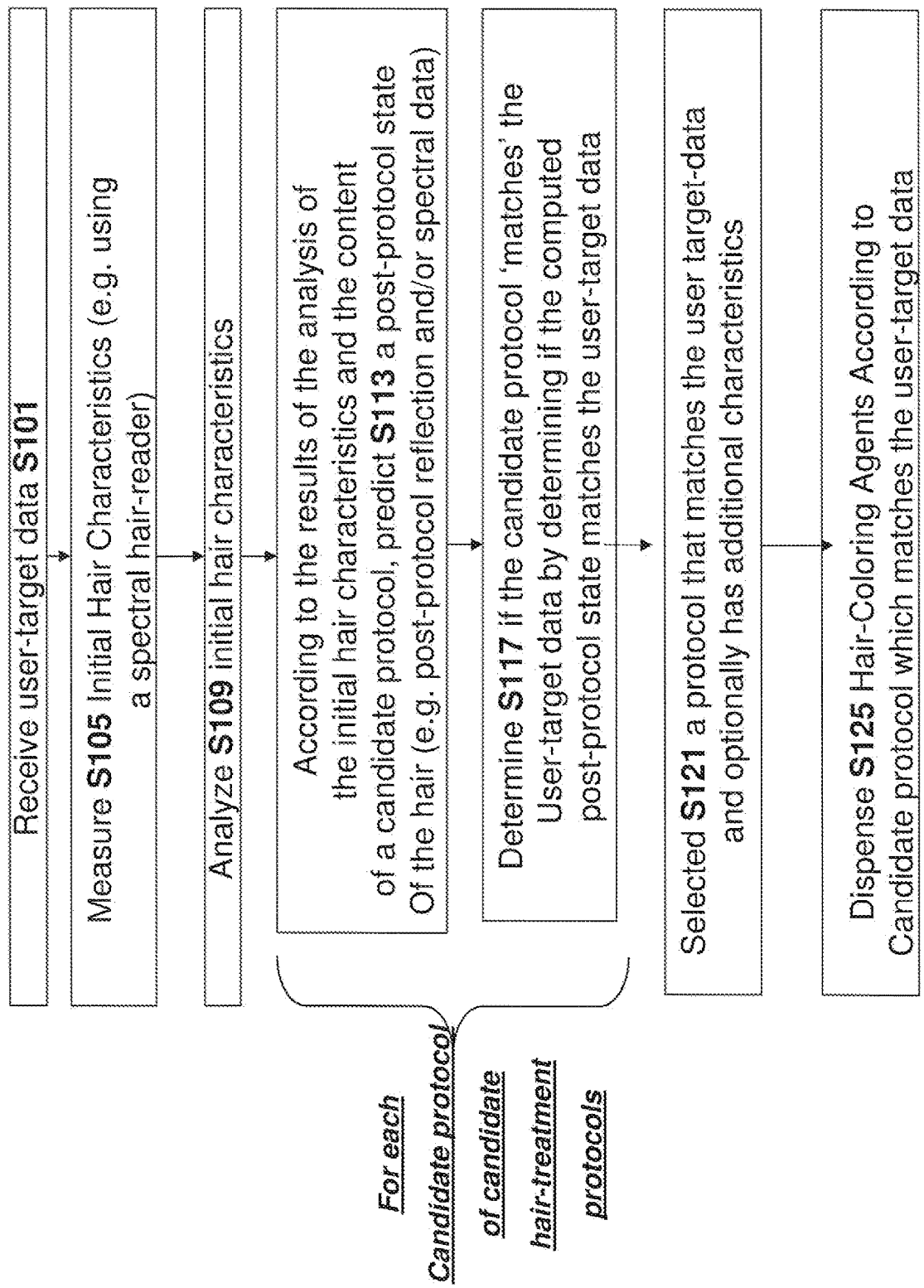
FIG. 4 is a flow-chart of a method for preparing a customized hair-coloring composition.

FIGS. 3A-3B illustrate a non-limiting example of a hair-reader 3110 in accordance with some embodiments. Hair-reader 3110 includes a housing 804 (e.g. opaque) and a window 808. In FIG. 3B, a plurality of keratinous fibers 812 are substantially aligned along an alignment axis which corresponds to the 'y' axis.

FIG. 4 is a flow-chart of a non-limiting example of a technique for hair-coloring for example, using the system of FIG. 1. In step S101, user-target data is received and stored (e.g. in volatile and/or non-volatile computer-readable storage). Typically, the user-target data relates to a selected shade or color—e.g. a user desires to color his/her hair to the selected shade or color. In step S105, characteristic of a user's hair are measured—e.g. using at least a hair-reader device (e.g. for measuring at least one hair-reflection value or for measuring a hair-reflection-spectrum(a)) such as that illustrated in FIG. 2 or 4 or that disclosed in PCT/IB2012/051351 or any related hair-reader device, as discussed below. These characteristics may be electronically analyzed in step S109. According to the technique of FIG. 4, it is possible to compute a 'customized' hair-treatment that is specific to (i) an initial pre-treatment state of the user's hair (e.g. as measured in step S105 and analyzed in step S109) and (ii) the user-target data.

The term 'user-target' typically includes to a target color shade—e.g. expressible as a value in color-space such as Hunter Lab color space or any other color space. In addition to a target color shade, user-target data may also include some other desired characteristic of any proposed hair-treatment—e.g. a treatment of 'roots-only' as opposed to 'entire-hair-shaft,' a maximum treatment time, etc.

A plurality of hypothetical or 'candidate' hair-treatment protocols may be analyzed and considered. A 'hair-treatment' may refer to any one of: (A) content of a hair-coloring composition (or more than one hair-coloring composition which may be applied sequentially or simultaneously—for example, a dye-containing composition and a bleaching composition) to be applied to the hair and/or (B) other treatment parameters—e.g. treatment durations, treatment temperature. Computing or specifying a 'hair-treatment' may include specifying at least absolute or relative quantities or 'loads' (i.e. expressed in molar terms, or as weights, or a volumes, or in any other manner known in the art) of one or more hair-coloring agents of a hair-coloring composition (e.g. a 'multi-agent' composition). The term 'hair-coloring agent' may include an artificial colorant/dye, an oxidizer, an alkalizer or an other substance used in the art for temporary, semi-permanent, demi-permanent or permanent hair-coloring. A hair-coloring agent may be in any phase or form, including but not limited to liquid, gel, mouse, cream, solid, powder, tablet, or any other form known in the art. Optionally, a 'hair-treatment' also includes data relating to treatment time, treatment temperature, multi-stage treatments or any other parameter of treatment. For example, a hair-treatment may entail production of multiple distinct combinations of hair-coloring agents—e.g. a coloring mixture and a bleaching mixture which are applied in different stages.

For the present disclosure, the term 'hypothetical' and 'candidate' are used interchangeably and refer to possible treatments that may or may not be actualized.

Typically, the specific characteristics of each user's hair is quite individual (e.g. based upon his/her genotype, age, environmental effects etc.) and the number of potential target shades or colors may also be relatively large. Because of the myriad possible combinations of initial and target hair characteristics, the number of possible candidate/hypothetical hair-treatment protocols may be extremely large, and it is not always known a priori which hair-treatment protocols are predicted to be effective (or most effective) to transform hair from its initial state to a state matching the target data received in step S101.

As such, it may be necessary to electronically analyze multiple hypothetical hair treatments to identify a treatment (or set of more than one hypothetical hair-treatments) which successfully transforms the initial hair to a target color.

This is done in steps S113 and S117. Thus, in step S113, a post-protocol state for the hair is predicted for the hair-characteristics measured in step S105 and a specific candidate hair-treatment. In step S117, it is electronically determined if this post-protocol state matches the specifications of the user target-data.

The term 'hair-color treatment' is not restricted to introducing colorants (e.g. artificial colorants) into the hair (i.e. 'coloring') but may also include hair-bleaching.

In one non-limiting example, (i) in step S105 one or more initial reflection spectrum(a) are measured, (ii) in step S113 a hypothetical post-treatment reflection spectrum is computed from the initial reflection spectrum and specifics of a candidate hair-treatment protocol, and a color value (e.g. an LAB value) is computed from the hypothetical post-treatment reflection spectrum; and (iii) in step S117 this initial-hair-specific and candidate-protocol-specific LAB value is compared to an LAB value associated with the user-target data received in step S101.

In different embodiments, it is possible to measure a reflection spectrum, a transmission spectrum, a spectrum of deflected light, and an absorption spectrum.

In step S121, a protocol that matches the user target-data is selected. Optionally, for example, if more than one candidate protocol matches the user target-data, these candidate protocols may be analyzed and/or scored, and a more preferred matching hair-coloring protocol may be selected accordingly.

In step S125, according to the selected hair-coloring protocol, respective quantities of hair-coloring agent, for a plurality of hair-coloring agents, are each dispensed according to a specifics of the hair-coloring protocol selected in step S121.

One non-limiting example of a dispenser of hair-coloring agents is illustrated in FIG. 2. In this non-limiting example, different respective hair-coloring agents are disposed in each container of a plurality of containers 180A-180Q. In response to the results of step S121, for at least 2 or at least 3 or at least 4 or at least 5 or at least any number of hair-coloring agents, respective quantities of each hair-coloring agent are dispensed into a vessel (not shown) located in port 192.

In some embodiments, the dispenser is automatic and includes electronic circuitry for regulating quantities of hair-coloring agents that are dispensed.

For the present disclosure, a dispensing a plurality of hair-coloring agents according to the results of some sort of computational and/or electronic operation(s) (e.g. a predicting of a post-hypothetical-hypothetical-hair-treatment spectrum (e.g. reflection spectrum) or a color value derived therefrom) refers to one or more of two situations: (i) a situation whereby electronic circuitry automatically controls a dispensing device (the skilled-artisan is directed to PCT/IB2012/051351 incorporated herein by reference) and/or (ii) a situation whereby hair-coloring instructions computed from an electronic predicting is communicated to a human user (e.g. visually via a computer screen or in any other manner). The hair-coloring instructions may relate to relative quantities of hair-coloring agents and the human user follows the instruction to, for example, dispense hair-coloring agent(s) according to the quantities specified by the computer-provided instructions. The container for a chemical agent may have any form factor (e.g. rigid container, tube, etc) and may either may mounted to a dispenser device as illustrated in FIG. 2 or may be a 'free' or unmounted container.

Once these agents are dispensed into the vessel, one or more steps may, optionally, be performed to transform the contents of the vessel (not shown) into a hair-coloring mixture, which may then be applied to the user's hair to color the hair.

For the present disclosures, the terms ' input keratinous fiber(s)' and 'initial hair' are used interchangeably—both refers to keratinous fibers(s) (e.g. hair) which is subjected to one or measurements (e.g. optical measurements and/or reflection measurements—for example, to measure a hair-reflection spectrum(a)) for the purpose of predicting a final state of one or more hypothetical hair-treatments.

The skilled artisan will appreciate that not every step of FIG. 4 is required in every embodiment, the order of steps of FIG. 4 is not limiting—the steps may be performed a different order, additional steps may be performed, and one or more steps may be modified.

A Discussion of FIGS. 5-8

Figure 5:
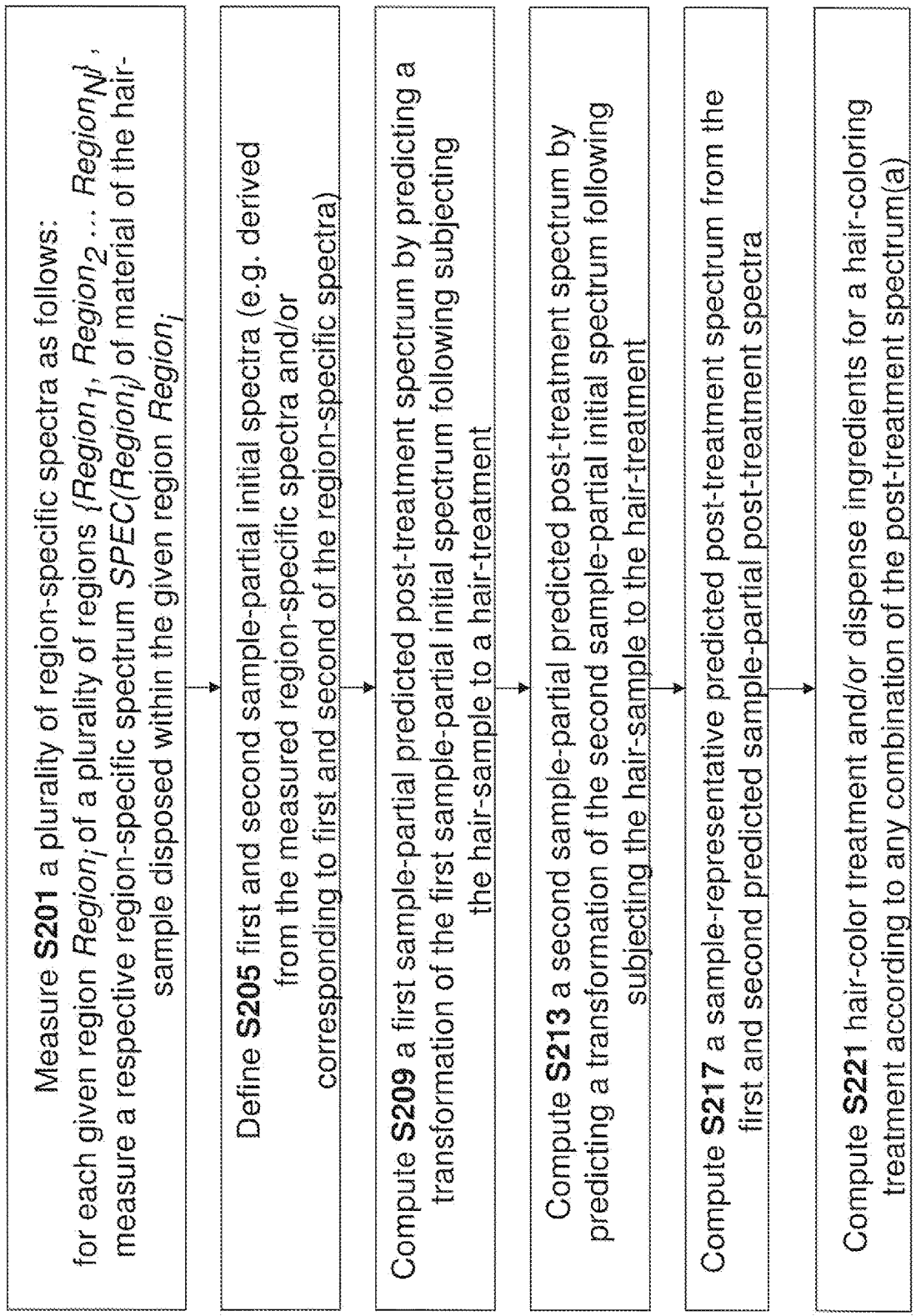
FIG. 5 is a flow-chart of method for predicting post-treatment spectra according to measured region-specific spectra.

FIG. 5 is a flow-chart of method for predicting post-treatment spectra according to measured region-specific spectra. FIG. 5 is explained with reference to FIGS. 6-7.

In step S201, a plurality of region-specific spectra are measured as follows—for each given region $Region_i$ of a plurality of regions $\{Region_1, Region_2, \ldots Region_N\}$ (N is a positive integer having a value of a least 2; i is a positive integer having a value between 1 and N), a region-specific spectrum $SPEC(Region_i)$ for hair-material disposed within the given region $Region_i$ is measured.

Figure 6A:
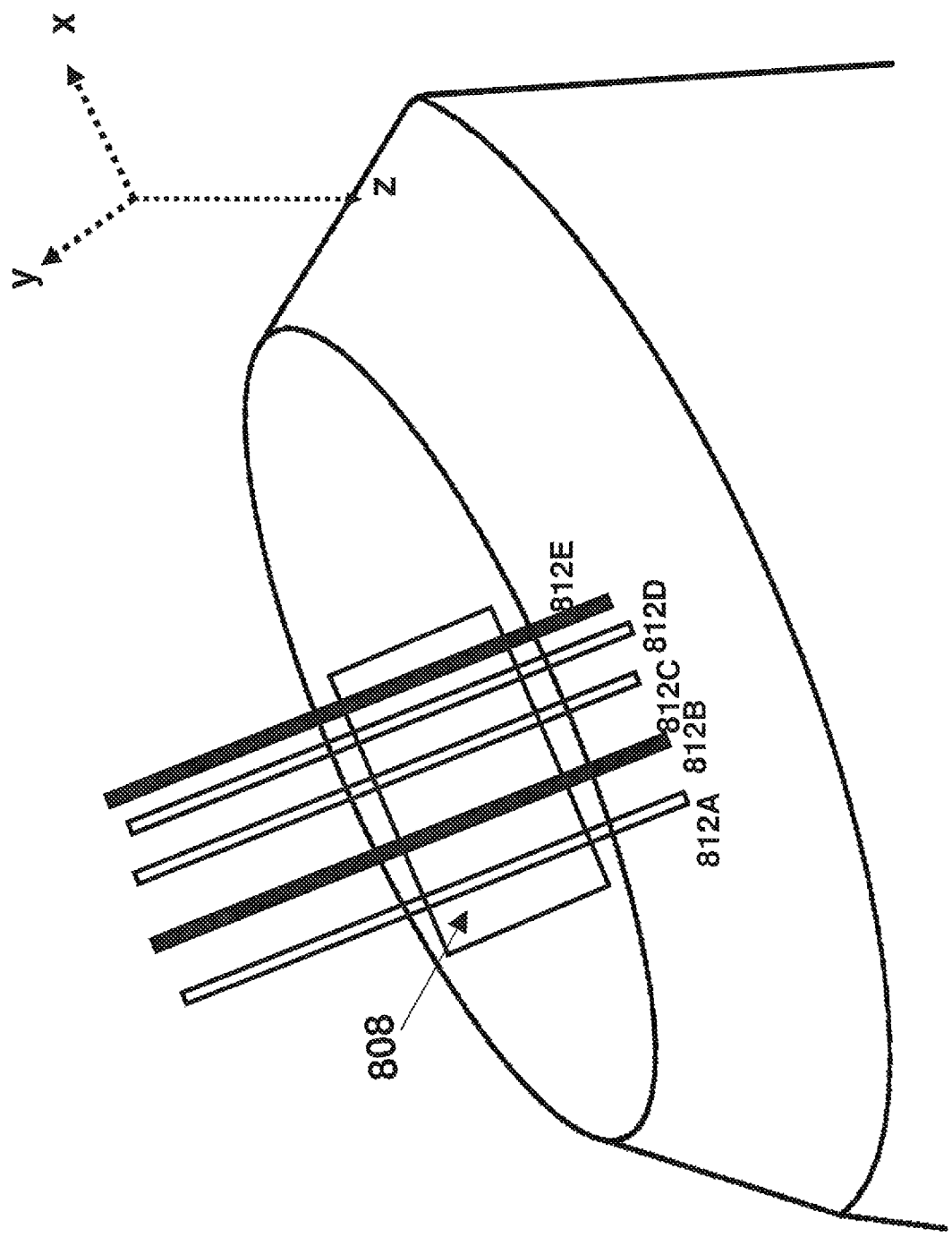
FIG. 6A illustrates hair-shafts on a window of a hair-reader device.

FIG. 6A is a close-up of the portion of FIG. 3B where the hair-shafts are disposed. FIG. 6A relates to one type of natural-gray hair. In the example of FIG. 6A, five hair-shafts 812A-812E are illustrated—shafts 812B and 812E are natural-black hair shafts (i.e. by virtue of a presence of natural hair pigments therein) and shafts 812A, 812C and 812D are natural-white hair shafts substantially free of melanin.

Figure 6B:
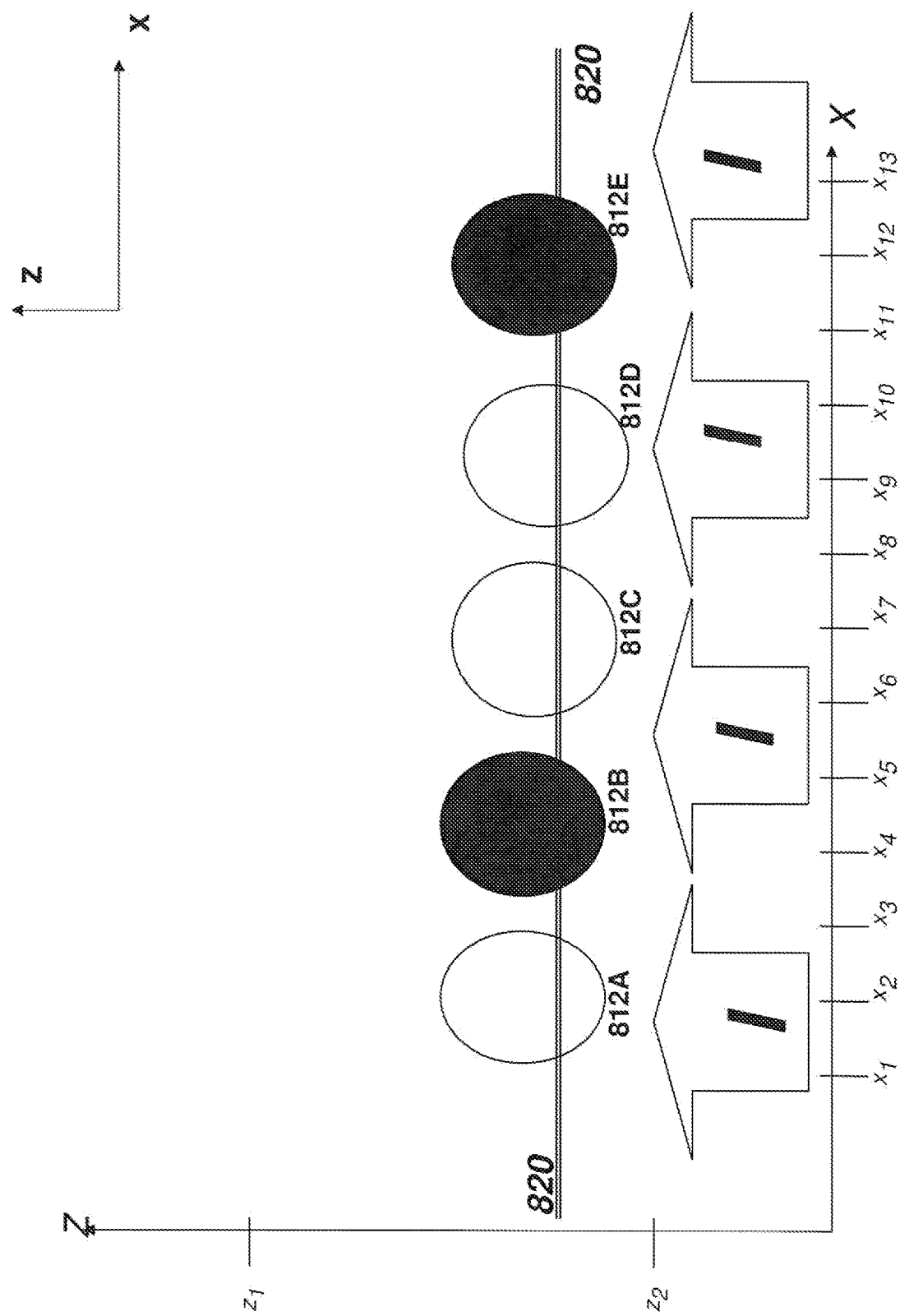
FIGS. 6B and 8 illustrate cross-sections of illuminated hair-shafts.

FIG. 6B is a cross-section view of the same five hair-shafts. In the example of FIG. 6B, illumination is "from below"—the block-arrows of FIG. 6B that are labeled with an I illustrate this illumination. Light reflected back "down" from the hair shaft is collected by a detector. In this example, the region-dependent spectra are generated on the basis of the reflected light. Also illustrated in FIG. 6B is object plane 820, defined by optics of the detector (NOT SHOWN). As shown in FIG. 6B, object plane 820 passes through the hair-shafts.

Figure 6C:
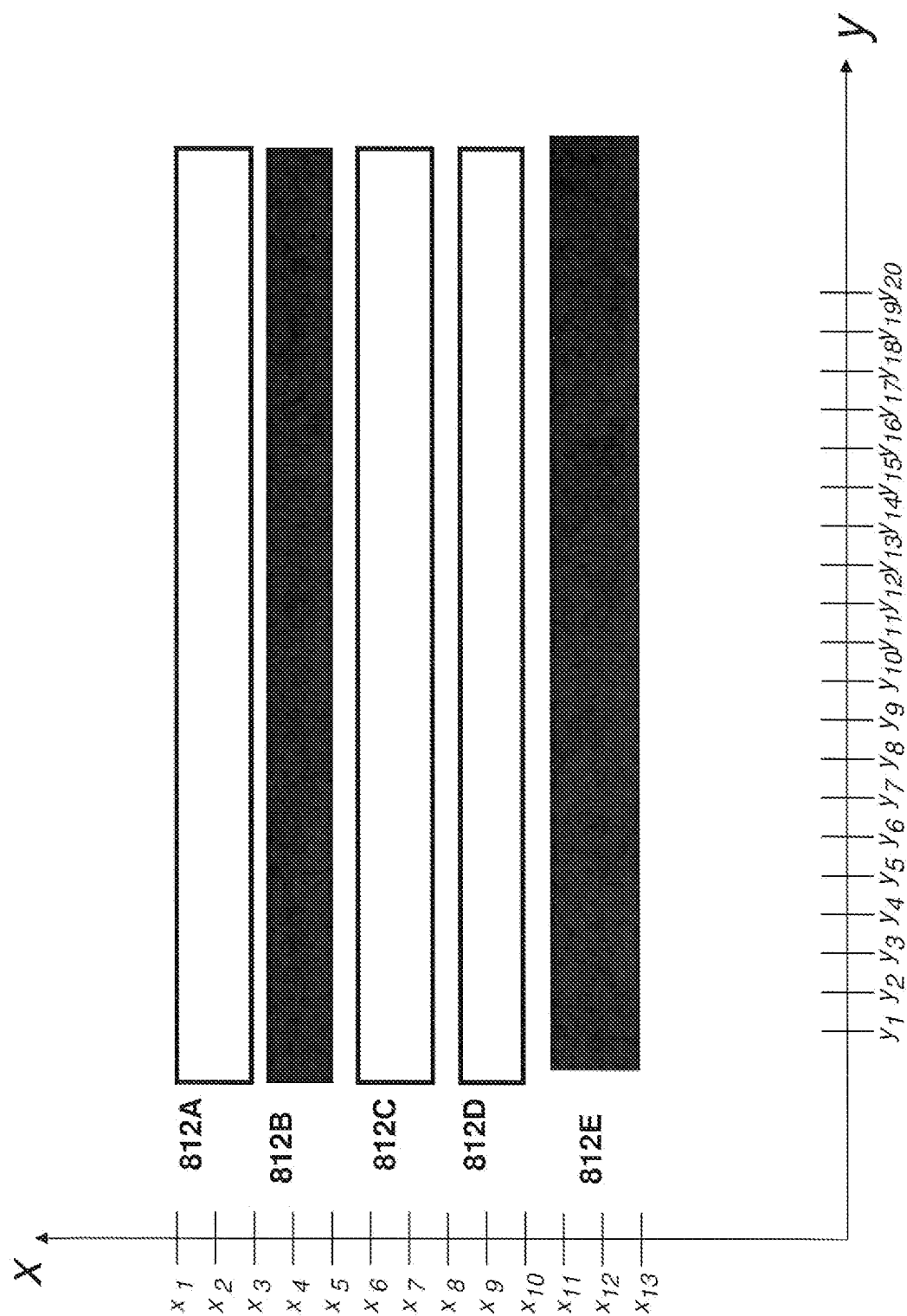
FIGS. 6C and 7A are top-down views of illuminated hair-shafts.

FIG. 6C illustrates a cross section of the same five hair-shafts 812A-812E in the x-y plane—e.g. in object plane 820.

The intersection between a 'region of space' (i.e. in 3-dimensions, having finite dimensions) and object plane is a portion or 'area of the plane.' By wave of example, when an infinite plane passes through a solid sphere, the intersection is the locus of points within a spectrum. Thus, the intersection between a 'region of space' and a plane (e.g. an object plane) is referred to either as a 'slice of the object plane' or a "region-object-plane intersection-area".

The term "region:object-plane intersection-area" refers to the area of object plane 820 contained given region. When an object plane 'passes through' a plurality of regions, the object plane and the regions define a plurality of 'region: object-plane intersection areas."

As will be discussed below (see FIG. 16), the intersection between a region of space and an area may also be obtained by subjecting the region of space to a perpendicular projection. Thus, in some embodiments, a 'region:object-plane intersection of a region is synonymous with a perpendicular projection of the region.

Figure 7A:
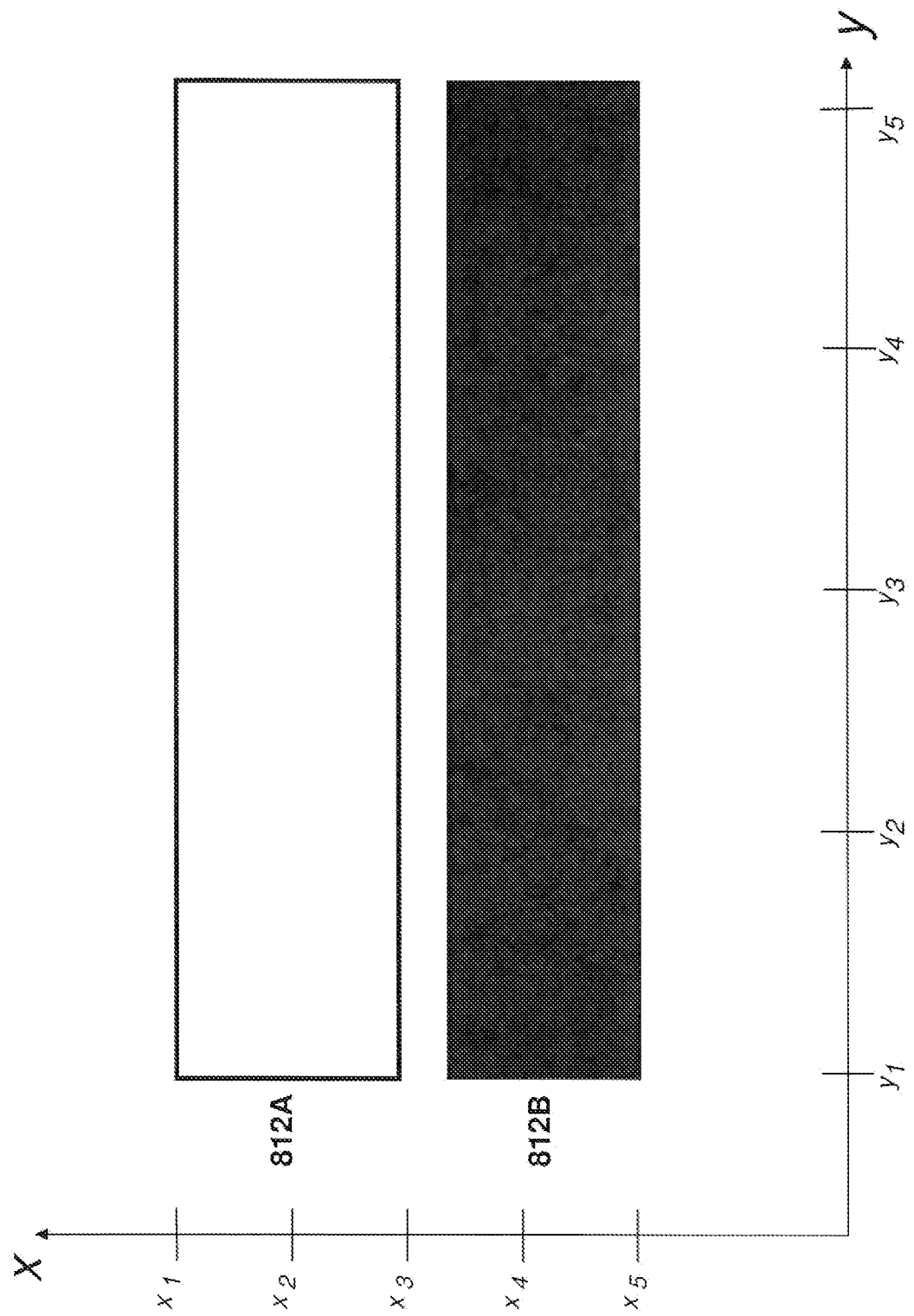

FIG. 7A illustrated a portion of the planar-region of FIG. 6A—in the x-direction. FIG. 7A is restricted to the portion of the x-axis between $x_1$ and $x_5$ and is restricted to the portion of the y-axis between $y_1$ and $y_5$.

In one example related to FIGS. 6A-6B, it is possible to define 228 regions of space (all shaped as rectangular prisms) as follows: (A) all regions are bound in the z-direction by $z_1$ and $z_2$; (B) $Region_1$ of space is bound by $x_1$ and $x_2$ (i.e. in the x-direction) and bound by $y_1$ and $y_2$ (i.e. in the y-direction); $Region_2$ of space is bound by $x_2$ and $x_3$ (i.e. in the x-direction) and bound by $y_1$ and $y_2$ (i.e. in the y-direction); .... $Region_{12}$ of space is bound by $x_{12}$ and $x_{13}$ (i.e. in the x-direction) and bound by $y_1$ and $y_2$ (i.e. in the y-direction); $Region_{13}$, of space is bound by $x_1$ and $x_2$ (i.e. in the x-direction) and bound by $y_2$ and $y_3$ (i.e. in the y-direction); .... $Region_{228}$ of space is bound by $x_{12}$ and $x_{13}$ (i.e. in the x-direction) and bound by $y_{19}$ and $y_{20}$ (i.e. in the y-direction).

Figure 7B:
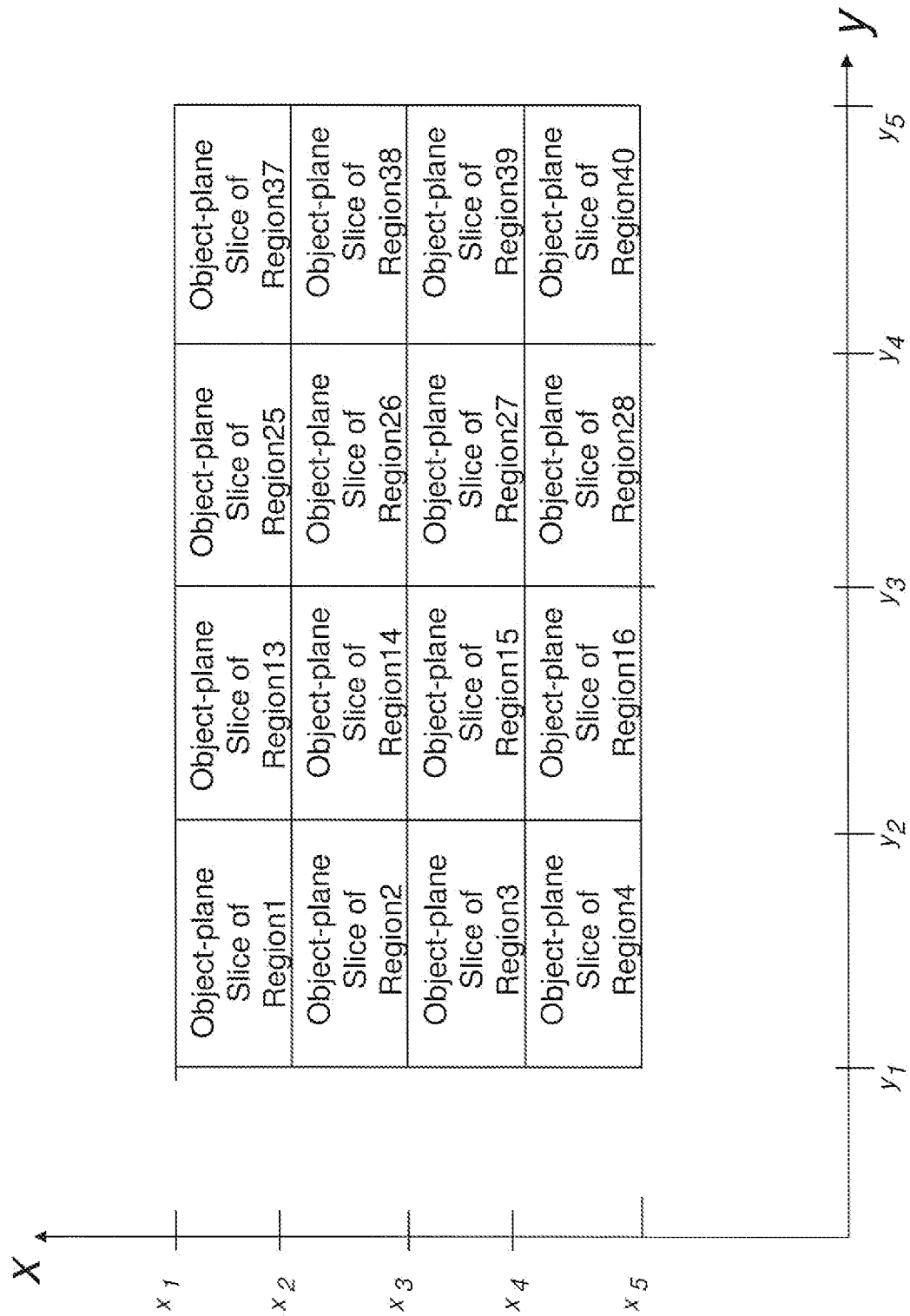
FIG. 7B illustrates an intersection between a plurality of regions and an object plane.

Due to space constraints, these regions are not explicitly labeled as such in FIG. 6C. As noted above, FIG. 7A illustrates a portion of the planar-region of FIG. 6C. In FIG. 7B, an intersection between object-plane 820 and some of the 228 regions are labeled.

The locations in FIG. 7B correspond to those of FIG. 7A. In particular, FIG. 7B relates to the following regions-of-space $Region_1$, $Region_{13}$, $Region_{25}$, $Region_{37}$; $Region_2$, $Region_{14}$, $Region_{26}$, $Region_{38}$; $Region_3$, $Region_{15}$, $Region_{27}$, $Region_{39}$; $Region_{41}$, $Region_{16}$, $Region_{28}$, $Region_{407}$;

Because these regions-of-space are three-dimensional, and because FIG. 7B is a two-dimensional figure, what is illustrated in FIG. 7B is not, in fact, each entire region, but rather a 'slice' of each region—i.e. an intersection between each region and a plane passing (e.g. object-plane 820) through all of the regions. These regions are labelled "object-plane slice' of the region—in this context, the term 'slice' is synonymous with 'region:object-plane intersection areas.'—thus, what is illustrated in FIG. 7B are 16 such 'intersection-areas' describing a respective intersection between each of 16 regions and a plane (e.g. object-plane 820) passing through all of the regions.

The "object-plane-slice of region' illustrates in FIG. 7B are all, in fact, perpendicular projections of the region into the object-plane 820.

The regions of the object plane, illustrated in FIG. 7B (i.e. actually, two-dimensional 'slices' or 'intersection areas' are illustrated), are all 'single-shaft' with respect to white shaft 812A—$Region_1$. $Region_{13}$, $Region_{25}$ and $Region_{37}$—for all of these regions, their respective spectra $Spec(Region_1)$, $Spec(Region_3)$, $Spec(Region_{25})$, and $Spec(Region_{37})$ are generated primarily from light reflected from one of the natural-white hair shafts (i.e. shaft 812A). Similarly, the intersection of all of the regions with the object plane includes only locations where white-shaft-material is located.

The following regions of the object plane, illustrated in FIG. 7B, are all of which are 'single-shaft' with respect to black shaft 812B—$Region_4$, $Region_{16}$, $Region_{28}$ and $Region_{40}$,—for all of these regions, their respective spectra $Spec(Region_4)$, $Spec(Region_{16})$, $Spec(Region_{28})$, and $Spec(Region_{40})$ are generated primarily from light reflected from one of the natural-black hair shafts (i.e. shaft 812B). Similarly, the intersection of all of the regions with the object plane includes only locations where black-shaft-material is located.

Reference is made, once again, to FIG. 5. In step 201, a set of region-specific spectra $\{Spec(Region_1), Spec(Region_2), \ldots, Spec(Region_N)\}$ are generated.

Based upon these region-specific spectra, it is possible to designate and/or compute "initial spectra" in step S205. The term 'sample partial' in step S205 relates to the fact that the spectra is representative of only a portion of the sample, and not of the sample as a whole. Steps S205-S13 are now explained in terms of two non-limiting examples.

First Example Related to Step S205-S213

It may be decided that since the intersection of $Region_1$ and the object-plane 820 only includes locations within a white shaft 812A, that $Spec(Region_1)$ is representative of white-hair-shaft spectra. Alternatively or additionally, it may be decided that since $Spec(Region_1)$ is generated primarily from light scattered by white hair-shaft (i.e. shaft 812A), that $Spec(Region_1)$ is representative of white-hair-shaft spectra.

It may be decided that since the intersection of $Region_4$ and the object-plane 820 only includes locations within a white shaft, that $Spec(Region_4)$ is representative of black-hair-shaft spectra 812B. Alternatively or additionally, it may be decided that since $Spec(Region_4)$ is generated primarily from light scatted by a black hair-shaft (i.e. shaft 812B), that $Spec(Region_4)$ is representative of black-hair-shaft spectra.

In this "first" example, in step S209 a transformation of $Spec(Region_1)$ after subjecting the hair-sample to a hair-coloring treatment is predicted—the result is TREAT-MENT_TRANSFORMED($Spec(Region_1)$). This may be performed using any method known in the art, including but not limited to techniques disclosed in U.S. Pat. No. 7,110,117 and PCT/IB2012/051351, both of which are incorporated by reference in their entirety. For example, (i) initial concentration(s) of one or more natural pigments within the hair-shaft may be computed from $Spec(Region_1)$, (ii) an influence a bleaching upon natural pigments (i.e. having the computed initial concentration(s)) and/or a final concentration of artificial colorants may be computed according to the particulars of the hair-coloring process and (iii) TREATMENT_TRANSFORMED($Spec(Region_1)$) may be computed according to the final predicted concentration of natural and artificial colorants within hair shafts that are initially natural-white (i.e. as represented by $Spec(Region_1)$)).

In this "first" example, $Spec(Region_4)$ is representative of the natural-black hair shaft spectrum. Thus, in this first example, in step S213 a transformation of $Spec(Region_4)$ after subjecting the hair-sample to a hair-coloring treatment is predicted—the result is TREATMENT_TRANSFORMED($Spec(Region_4)$).

Thus, the 'first example' relates to the case where the first and second initial spectra correspond to first and second region-specific spectra.

Second Example Related to Step S205-S213

In this example, an initial spectra representative the 'white hair shafts' (i.e. which is subsequently transformed in step S209) is defined in step S205 according to the average of the following region-specific spectra (all of which are generated primarily by light scattered from natural-white hair shafts and/or generated from matter within a region of space whose intersection with the object plane 820 only includes locations within a white shaft)—$Spec(Region_1)$, $Spec(Region_{13})$, $Spec(Region_{25})$, and $Spec(Region_{37})$. Thus, the first initial spectrum, according to this second example, is AVG ($Spec(Region_1)$, $Spec(Region_{13})$, $Spec(Region_{25})$, $Spec(Region_{37})$).

Thus, in this "second" example, the first spectrum is 'derived from' a plurality of region-specific spectra—i.e. to be representative of white shafts.

In this example, an initial spectra representative the 'black hair shafts' (i.e. which is subsequently transformed in step S213) is defined in step S205 according to the average of the following region-specific spectra (all of which are generated primarily by light scattered from natural-black hair shafts and/or generated from matter within a region of space whose intersection with the object plane 820 only includes locations within a black shaft)—$Spec(Region_4)$, $Spec(Region_{16})$, $Spec(Region_{28})$, and $Spec(Region_{40})$. Thus, the first initial spectrum, according to this second example, is AVG ($Spec(Region_4)$, $Spec(Region_{16})$, $Spec(Region_{28})$, $Spec(Region_{40})$).

The sample-representative predicted spectra (i.e. computed in step S217) may be used in any manner and for any purpose. In some embodiments, the method includes step S221 where the predicted spectra is used to compute a hair-coloring treatment and/or dispense ingredients therefor.

Figure 8:
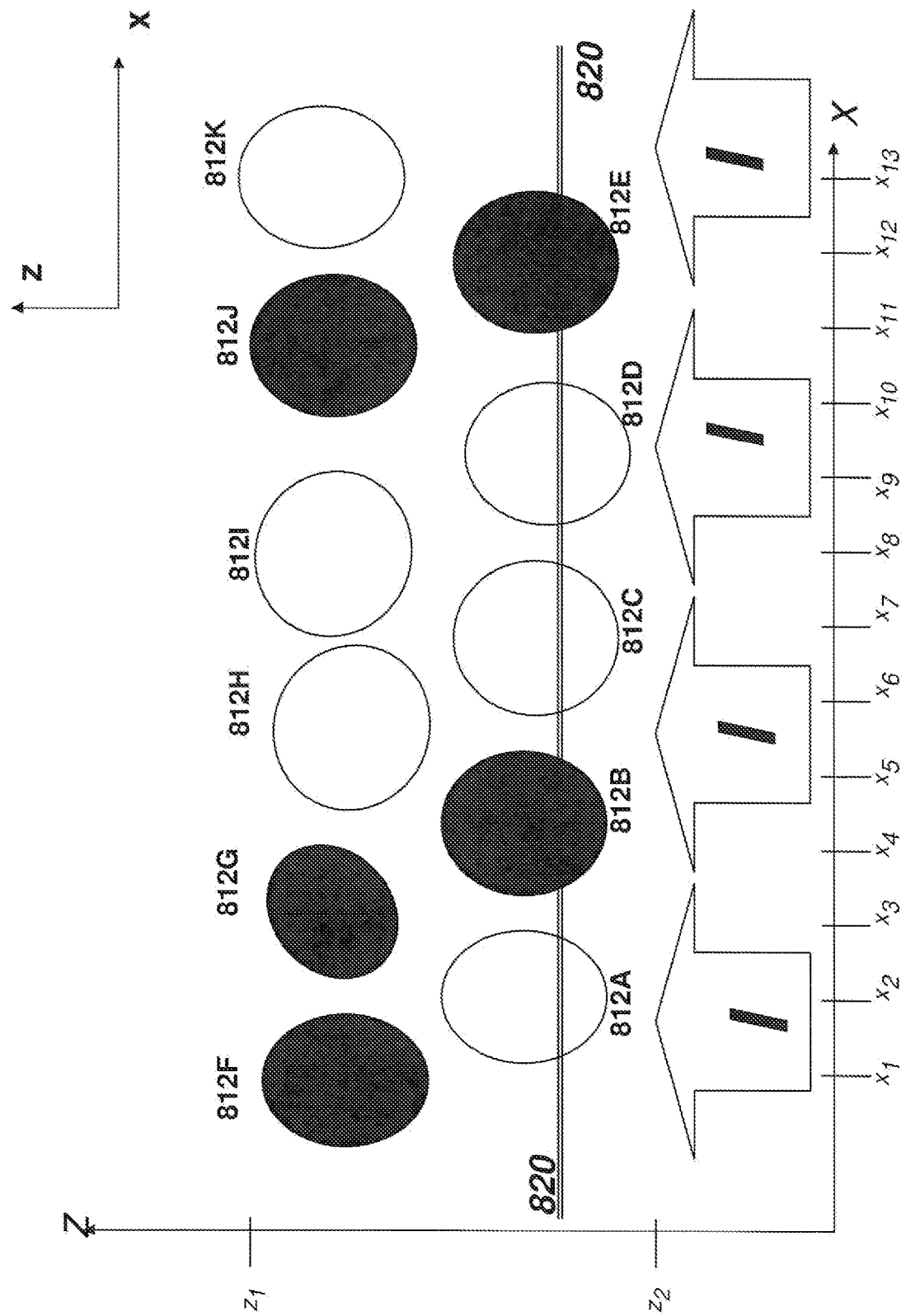

Reference is now made to FIG. 8 which may be compared to FIG. 6B. In the example of FIG. 6B, a single row of hair-shafts is illustrated. In the example of FIG. 8, an upper row of hair-shafts 812F-812K is shown in addition to the lower row of hair-shafts 812A-812E. When illuminated from below, scattering (in this reflection) is performed primarily but not exclusively by the lower row 812A-812E of hair-shafts which are the 'front row' relative to the illumination.

Figure 9:
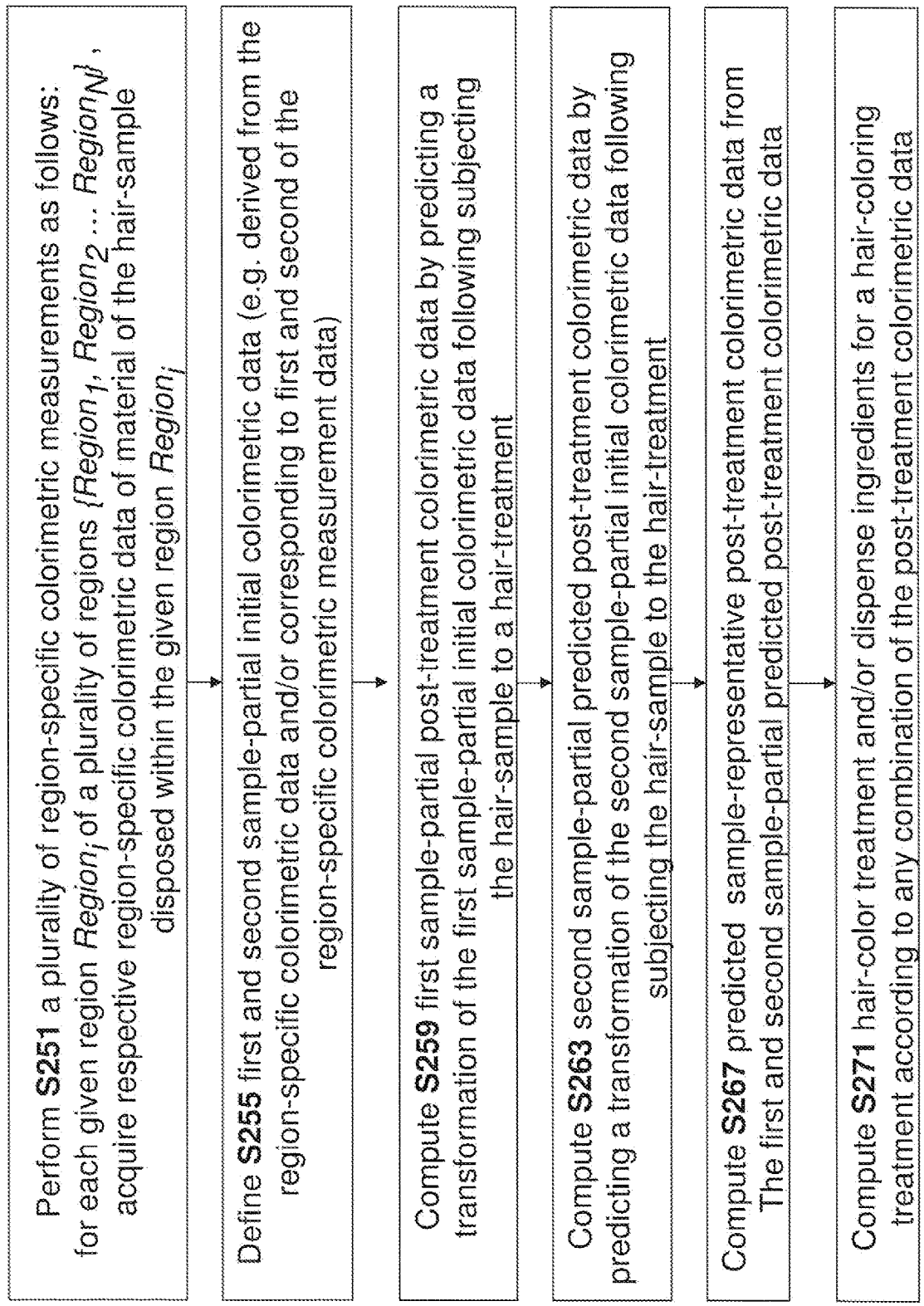
FIG. 9 is a flow-chart of method for predicting post-treatment colorimetric data according to measured region-specific colorimetric data.

Before discussing FIG. 9, an additional group of terms are now defined.

A plurality of regions {Region$_1$, Region$_2$, ... Region$_N$} defines a set of "region-pairs" as the set of all pairs (Region$_j$, Region$_k$) where j,k both positive integers between 1 and N and j≠k.]

A "volume ratio" between two regions Region$_j$, Region$_k$ is (i) 1 if they have the same volume or (ii) otherwise, is the ratio between the volume of the larger region to the volume of the smaller region.

For two overlapping regions Region$_j$, Region$_k$ (i.e. a 'pair' of regions that overlap) where j,k both positive integers between 1 and N and j≠k, the combined region is the union Region$_j$∪Region$_k$. The overlap fraction is the overlapping regions is the ratio between: (i) a volume of the overlapping portion of the region of the region-pair—i.e. a volume of Region$_j$∩Region$_k$ and (ii) a volume of the combined region Region$_j$∪Region$_k$ For an object plane OP and a plurality of regions Region the region:object-plane intersection area of region Region$_i$ is the portion of the object plane OP contained within Region$_i$. Unless specified otherwise, the term 'intersection area' Intersection_Area refers to a region:object-plane intersection area. FIG. 7B relates to the intersection of 16 regions with an object-plane and illustrates 16 portions of the object-plane—all of these portions (referred to as 'slices of the region') of the intersection plane are region:object-plane intersection areas or 'intersection areas.'

For an object plane OP and a plurality of regions {Region$_1$, Region$_2$, ... Region$_N$}, the plurality of regions defines a plurality of region-object-plane intersection areas as follows: for a region:object-plane intersection-area, the 'size' is the 'area' and is given in dimension of length$^2$—e.g. mm$^2$, or microns$^2$ A "size ratio" between two region:object-plane intersection-areas (i.e. a pair of the intersection-areas) is (i) 1 if the each of the intersection-areas has the same size; or (ii) the ratio between the larger of the intersection-areas and the smaller of the intersection-areas.

For two overlapping regions Intersection_area$_j$, Intersection_Area$_k$ defining where j,k both positive integers between 1 and N and j≠k, the combined area is the union Intersection_Area$_j$∪Intersection_Area$_k$. The overlap fraction is the overlapping intersection-areas (i.e. of a 'pair of intersection-areas') is the ratio between: (i) a size of the overlapping portion the intersection-area-pair—i.e. a size of Intersection_Area$_j$∩Region$_k$ and (ii) a size of the combined region Intersection_Area$_j$∪Intersection_Area$_k$ Discussion of FIG. 9

Reference is now made to FIG. 9. In step S251, a plurality of region-specific colorimetric measurements are performed—e.g. to acquire, for each region, LAB data or RGB data or any other colorimetric data in the art. In step S255, first and second sample-partial colorimetric data are defined. The 'sample partial' colorimetric data is representative of only a portion of the sample, and not of the sample as a whole.

The first and second colorimetric data are respectively transformed in step S259 and S263. In step S267, sample-representative colorimetric data is computed from the first and second sample-partial predicted post-treatment colorimetric data.

The sample-representative predicted colorimetric data (i.e. computed in step S217) may be used in any manner and for any purpose. In some embodiments, the method includes step S261 where the predicted spectra is used to compute a hair-coloring treatment and/or dispense ingredients therefore.

Figure 10A:
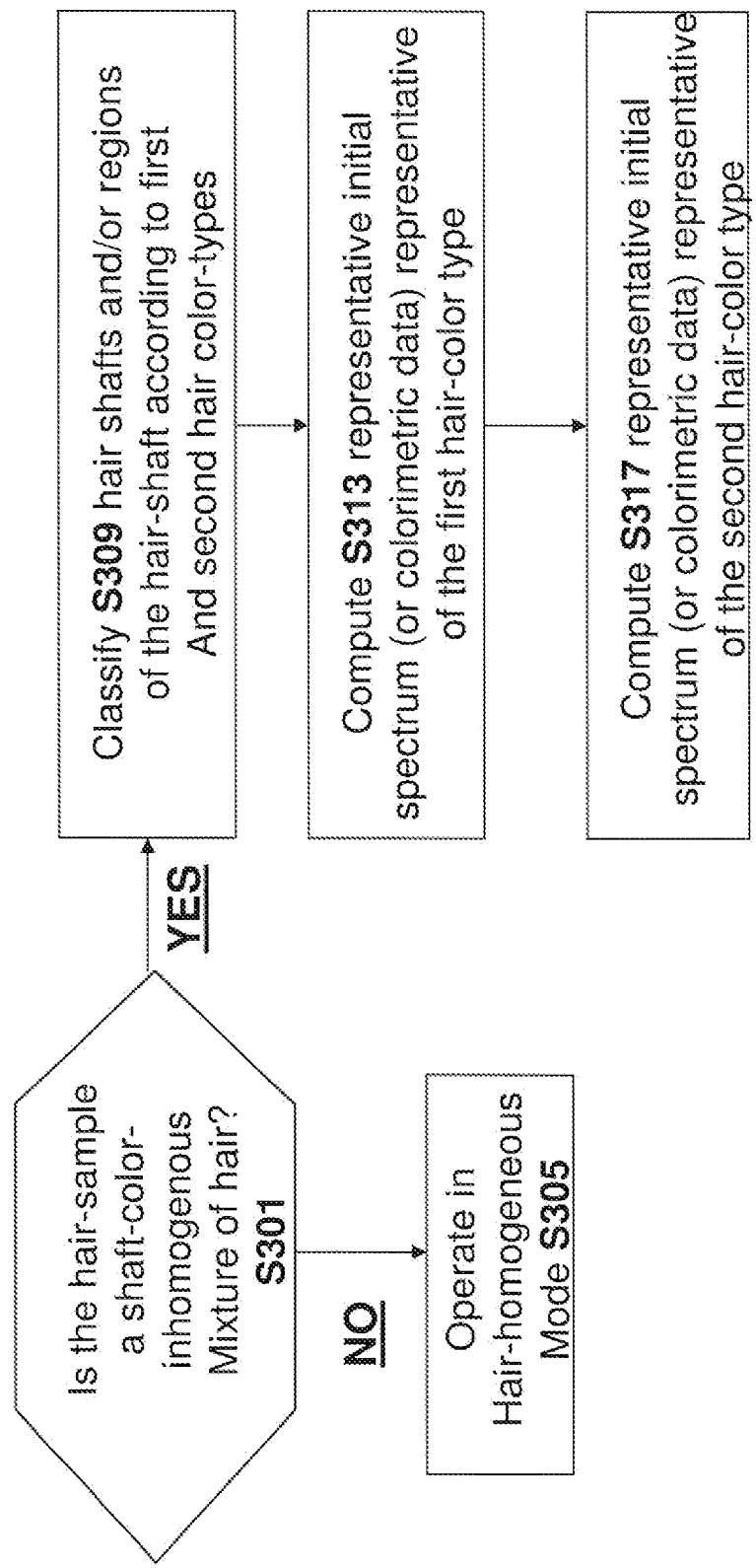
FIG. 10A is a flow chart is a technique for predicting a result of a hair-color-modifying treatment, according to some embodiments.
Figure 10B:
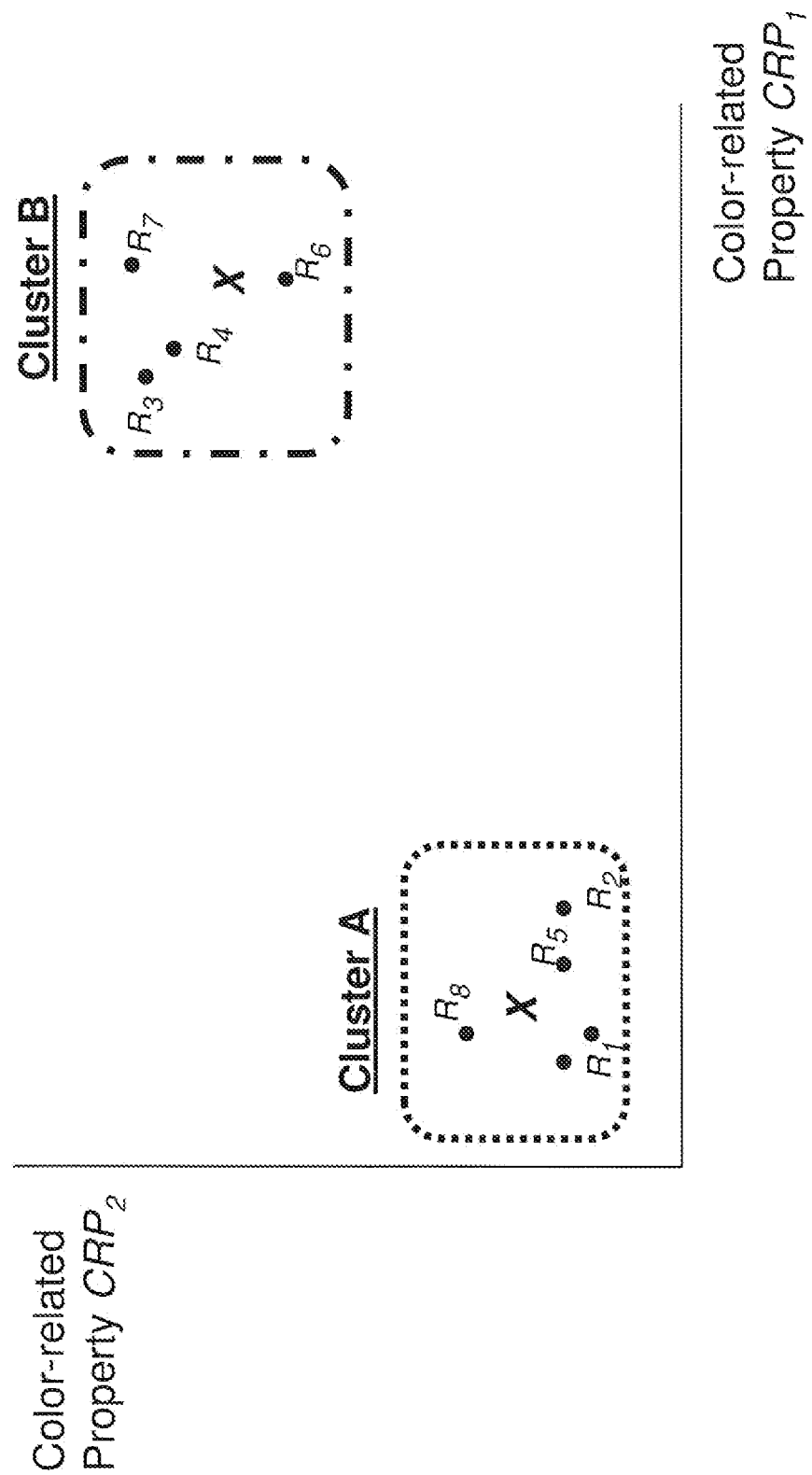
FIG. 10B illustrates clusters according to shaft color-properties.

A Discussion of FIGS. 10A-10B

FIG. 10A is a flow chart is a technique for predicting a result of a hair-color-modifying treatment, according to some embodiments.

In step S301, a determination is made if the hair-sample is a shaft-color-inhomogeneous mixture of hair (e.g. natural-gray hair) or not. If not, then in step S305, it is possible to operate in a hair-homogeneous mode 305. This determination may be made in any manner—in one example, a hair-stylist or other expert user may manually input data. Alternatively or additionally, optically-acquired data of a sample of hair may be analyzed to make the determination. For example, pixel data of a camera-acquired image of the hair may be compared to each other. In another example and as discussed below, sub-region-specific data for multiple sub-regions may be compared to each other.

In step S309, hair-shafts and/or regions thereof are classified according to hair shaft color-type. For example, natural-gray hair comprising white shafts and black shafts may be treated with a red dye to create formerly natural-gray hair comprising (i) light-red hair shafts (i.e. first color type) and (ii) dark-red hair shafts (i.e. second color type).

In one non-limiting example related to automatically detecting of hair type, it is possible to form clusters (see FIG. 10B)—e.g. in LAB space or according to any other color-related property. In the non-limiting example of FIG. 10B, each shaft is represented by a different point. In the example of FIG. 10B, it may be concluded that regions R1, R2, R5 and R8 are associated with a first cluster (e.g. natural-white hair) and R3, R4, R7 and R6 are associated with a second cluster (e.g. natural black hair).

Figure 11:
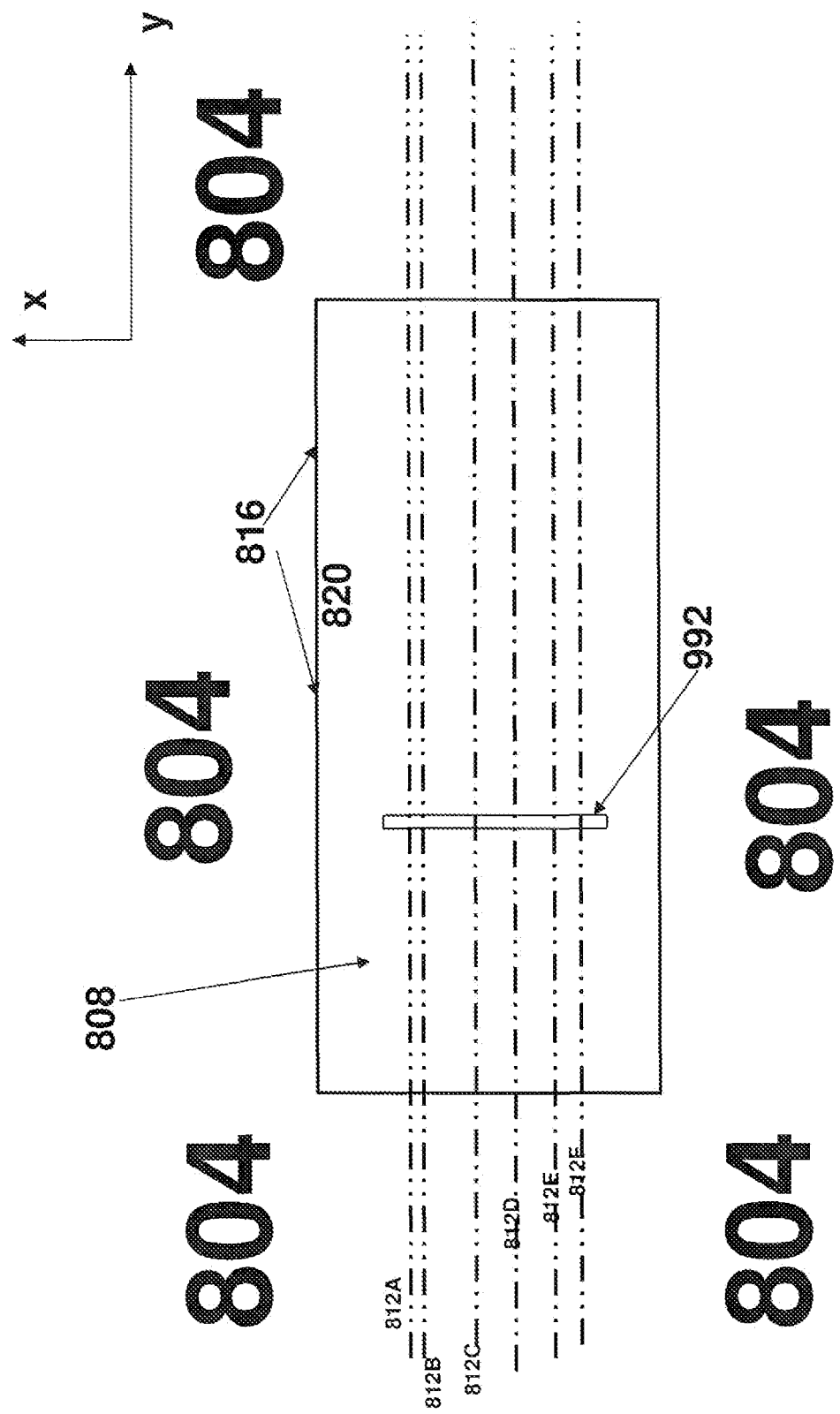
FIG. 11 is a close-up of substantially-aligned hair shafts on a window of hair-reading device.

Discussion of FIGS. 11-12

FIG. 11 a close-up of substantially-aligned hair shafts on window 808 of hair-reading device—window 808 includes a transparent surface 820 (e.g. of glass or plastic) and a support frame 816 for supporting transparent surface 820 on housing 804.

Figure 12A:
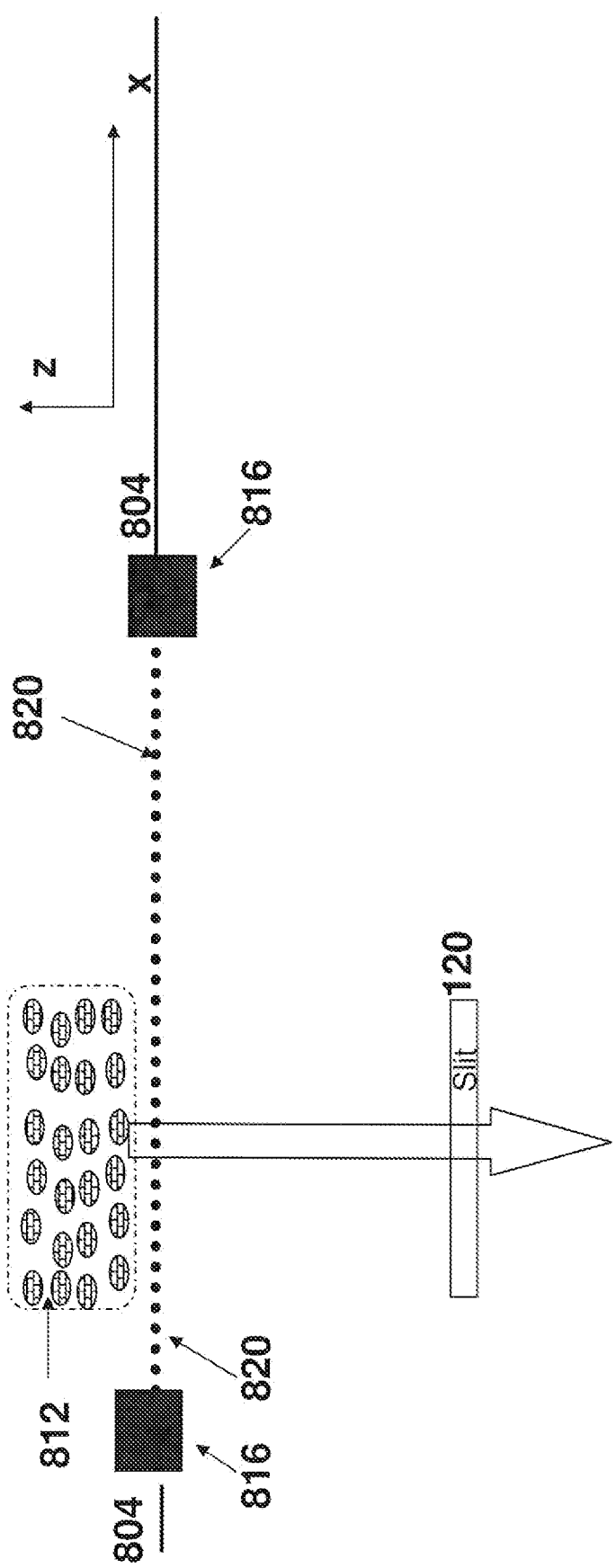
FIG. 12A-12B illustrate a plurality of keratinous fibers on a window of a spectral hair-reader.
Figure 12B:
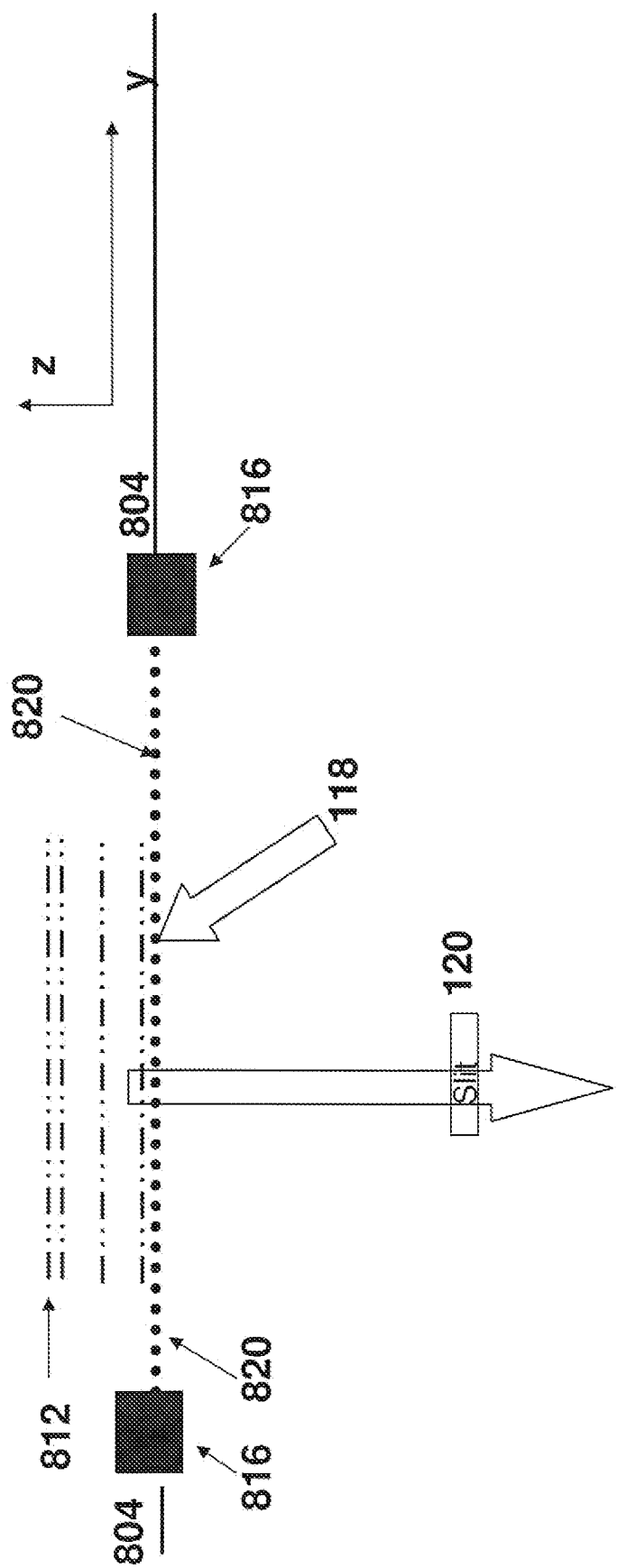

FIG. 12A-12B illustrate a plurality of keratinous fibers on a window of a spectral hair-reader 3110. FIG. 12A is a cross-section view while FIG. 12B is a side view. An illumination source 118 illustrates keratinous fibers, and light (e.g. primarily light of diffusive reflections) therefrom passes through slit or aperture 120. Additional components of the system of FIG. 12A are illustrated in FIGS. 13A-13B, discussed below.

Figure 13A:
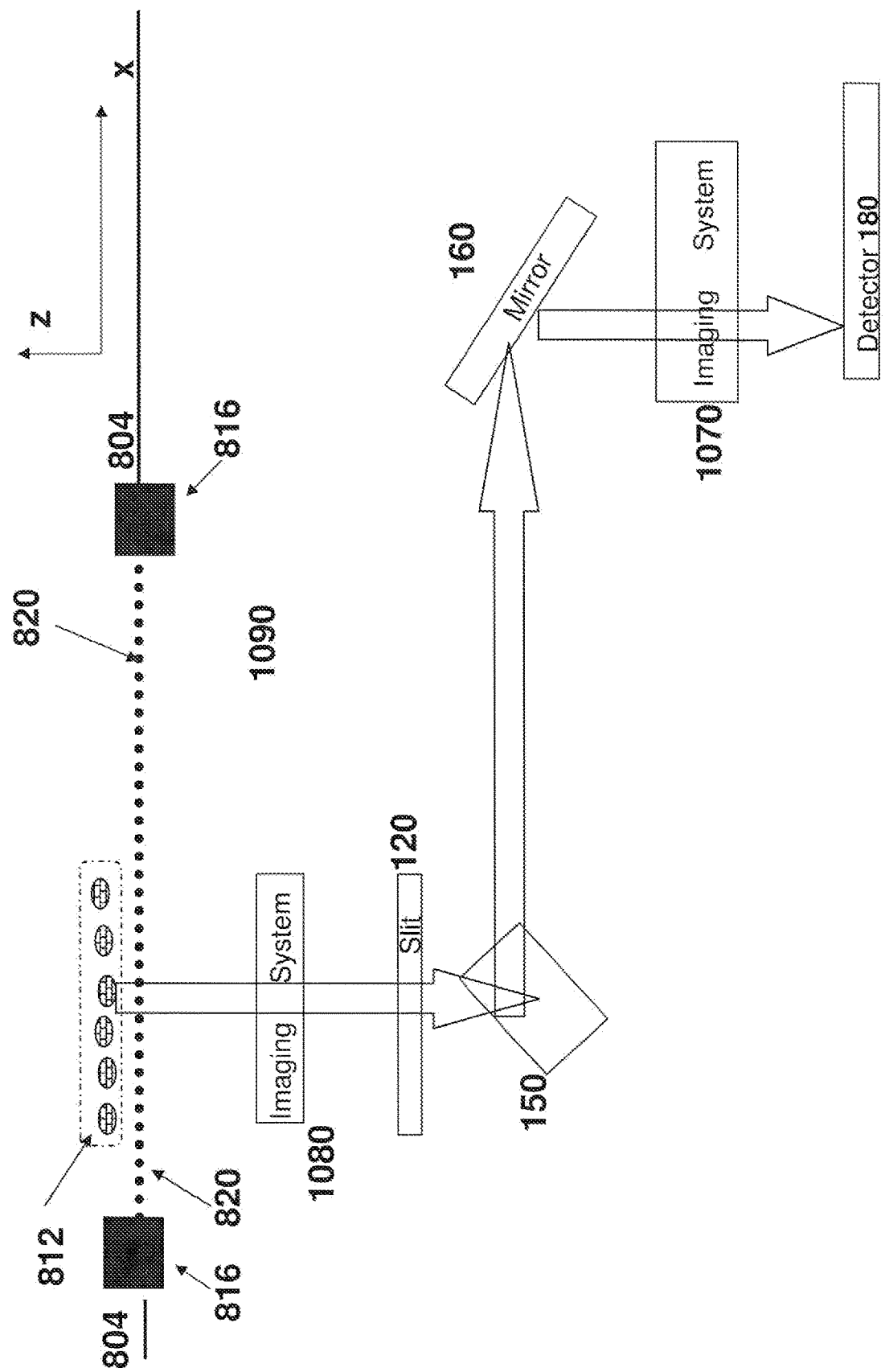
FIG. 13A illustrates an apparatus for measuring region-specific spectra of hair.

FIG. 13A is an non-limiting example of an apparatus for measuring a plurality of spectra of hair-shafts, each spectrum corresponding to a different respective sub-region in which a different respective set of hair-shafts (or portions thereof) are disposed. One salient feature of FIG. 13A is the presence of two imaging system 1080 and 1070, each of which comprises a different respective set of optical component(s).

Figure 13B:
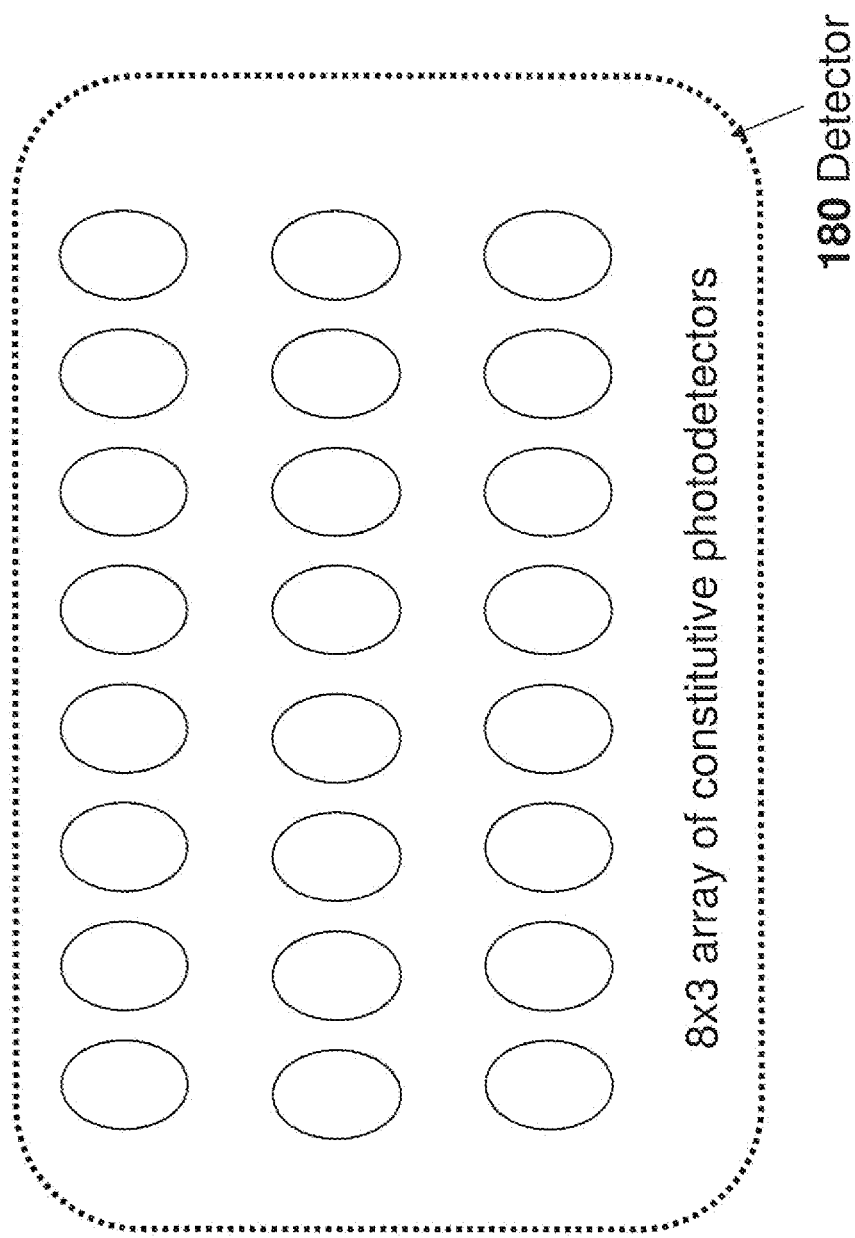
FIG. 13B illustrates a two-dimensional array of photodetectors.

In one non-limiting example, illustrated in FIG. 13B, detector 180 comprises an array (e.g. two-dimensional—for example, planar array) of photodetector—in the example of FIG. 12, this is an 8×3 array, though any other section of dimensions (e.g. comprising at least 2 rows and at least 2 columns) may be used. For example, a CCD or CMOS array may be employed.

In some embodiments, imaging system 1080 is operative to focus light reflected and/or deflected and/or transmitted from hair-shafts 812 before this reflected and/or deflected and/or transmitted light passes through slit or aperture 120 so that (i) the hair-shafts 812 are located in an object-plane and (ii) slit or aperture 120 is located in an image plane. In this non-limiting embodiment, the image located at 'image' plane is an 'intermediate image.' The 'intermediate image'

(e.g. at slit or aperture 120) may be an only-1D-focused-image—for example, a focused in a dimension perpendicular to hair-alignment axis 812—for example, along the x-axis (see 992 of FIG. 6).

In some embodiments, imaging system 1070 is operative to focus light reflected and/or deflected and/or transmitted from the hair-shafts after passing through slit 120 so that the hair slit 120 (or another 'intermediate' location where the intermediate image) is in an object plane and photodetectors 180 (e.g. a planar two-dimensional array thereof—e.g. a CCD or CMOS array) are in an image plane 180—thus, photodetectors 180 receive an image of slit 120 on which an image of hair-shafts 812 is present—an 'image of an' 'image.'

Alternatively, instead of a two-dimensional array of photodetectors (i.e. a 'starting' system), a scanning system may be employed—e.g. to achieve the effect of detecting a two-dimensional image at a focal plane of imaging system 1070.

The image is not required to be located exactly on slit or aperture 120. In and may be located on any location another intermediate location along the optical path between Also illustrated in FIG. 13A is grating 150. Alternatively, a prism may be used.

In another example, it is possible to detect reflection spectrum(a) and/or absorption spectrum(a) and/or transmission spectrum(a) using photodetector that have wavelength and/or 'color' (i.e. in the visible range or any other spectrum) sensitivity.

Similarly, there is no requirement of a slit or elongated aperture—other optical component(s) (e.g. lens(es)) may be configured to provide this functionality.

Thus, some embodiments relate to any device (e.g. monochromator device) configured to measure spectral data (e.g. a reflection, absorption or transmission spectrum) of the keratinous fiber(s).

As illustrated in the non-limiting example of FIG. 13B, (i) Row A of the 2D-array of photodetectors 180 is used to detect spectral data of keratinous fiber(s) within sub-region 840A; (ii) Row B of the 2D-array of photodetectors 180 is used to detect spectral data of keratinous fiber(s) within sub-region 840B; (iii) Row C of the 2D-array of photodetectors 180 is used to detect spectral data of keratinous fiber(s) within sub-region 840C. Examples of such spectrum are illustrated in the right-hand column of FIG. 13B.

A Discussions of FIGS. 14-16

When light is processed by optics of FIGS. 13A-13B, one or more (i.e. any combination of) Feature A and/or Feature B and/or Feature C may be provided.

Figure 14A:
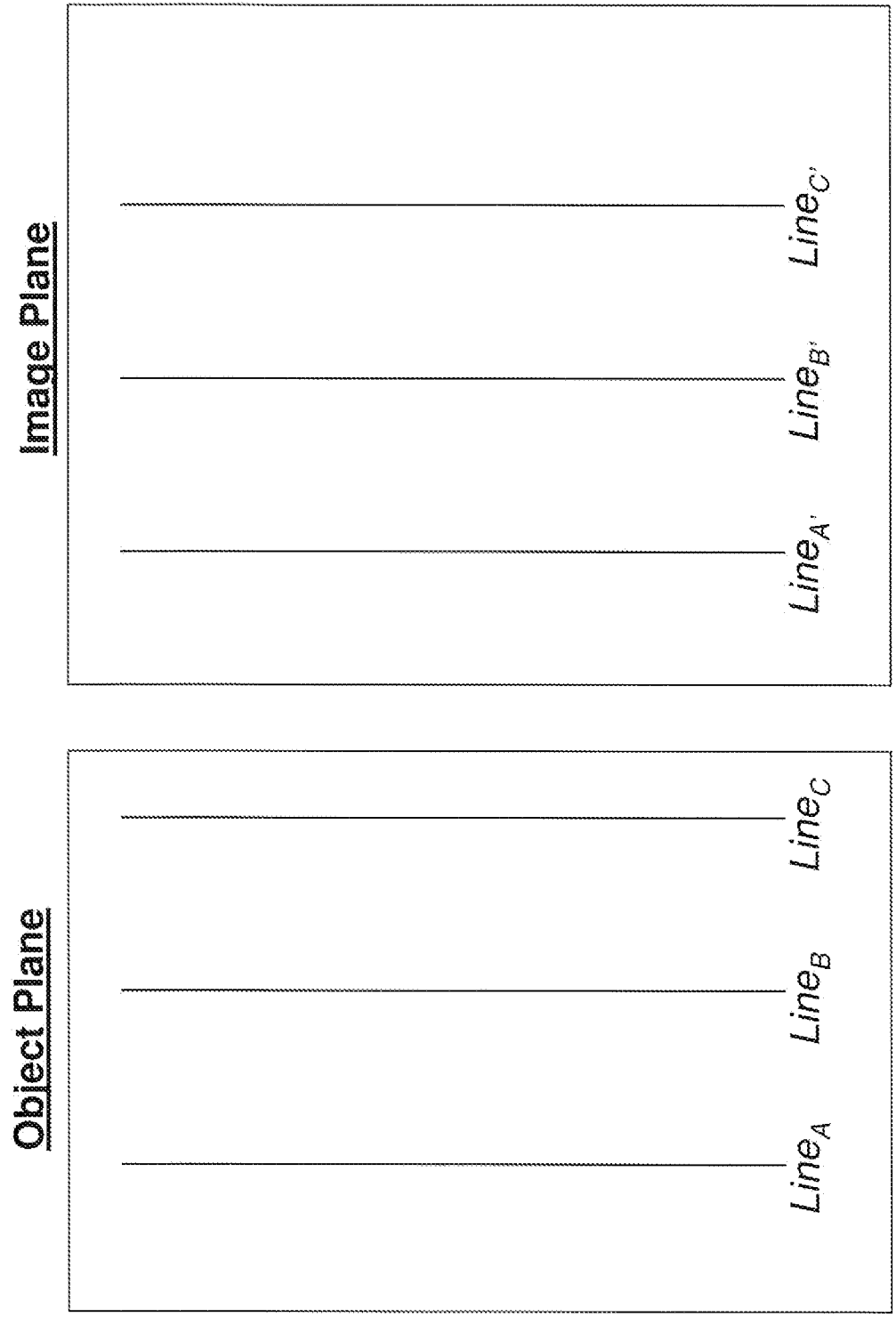
FIGS. 14A-14B, 15A-15B, 16-16B illustrate corresponding parallel lines in the object plane and the image plane.

Reference is now made to FIG. 14A. FIG. 14A illustrates 3 parallel lines in the object plane $Line_A$, $Line_B$ and $Line_C$, and 3 object lines in the image plane $Line_{A'}$, $Line_{B'}$ and $Line_{C'}$, $Line_{A'}$ is a 'corresponding line' relative to $Line_A$, $Line_{B'}$ is a 'corresponding line' relative to $Line_B$, and so on (i.e. the A line and the A' line are corresponding, the B line and the B' line are corresponding, and so on).

Feature A—along each given line of a set of parallel lines in the image plane, only light from a corresponding line of a set of parallel lines in the object plane reaches the given line in the image plane.

In the example of FIG. 14A, the light is processed (e.g. by the system of FIGS. 13A-13B) so that only light from $Line_A$ reaches $Line_{A'}$, only light from Lines reaches $Line_{B'}$, and so on. Thus, no light from $Line_B$ reaches $Line_{A'}$.

Figure 14B:
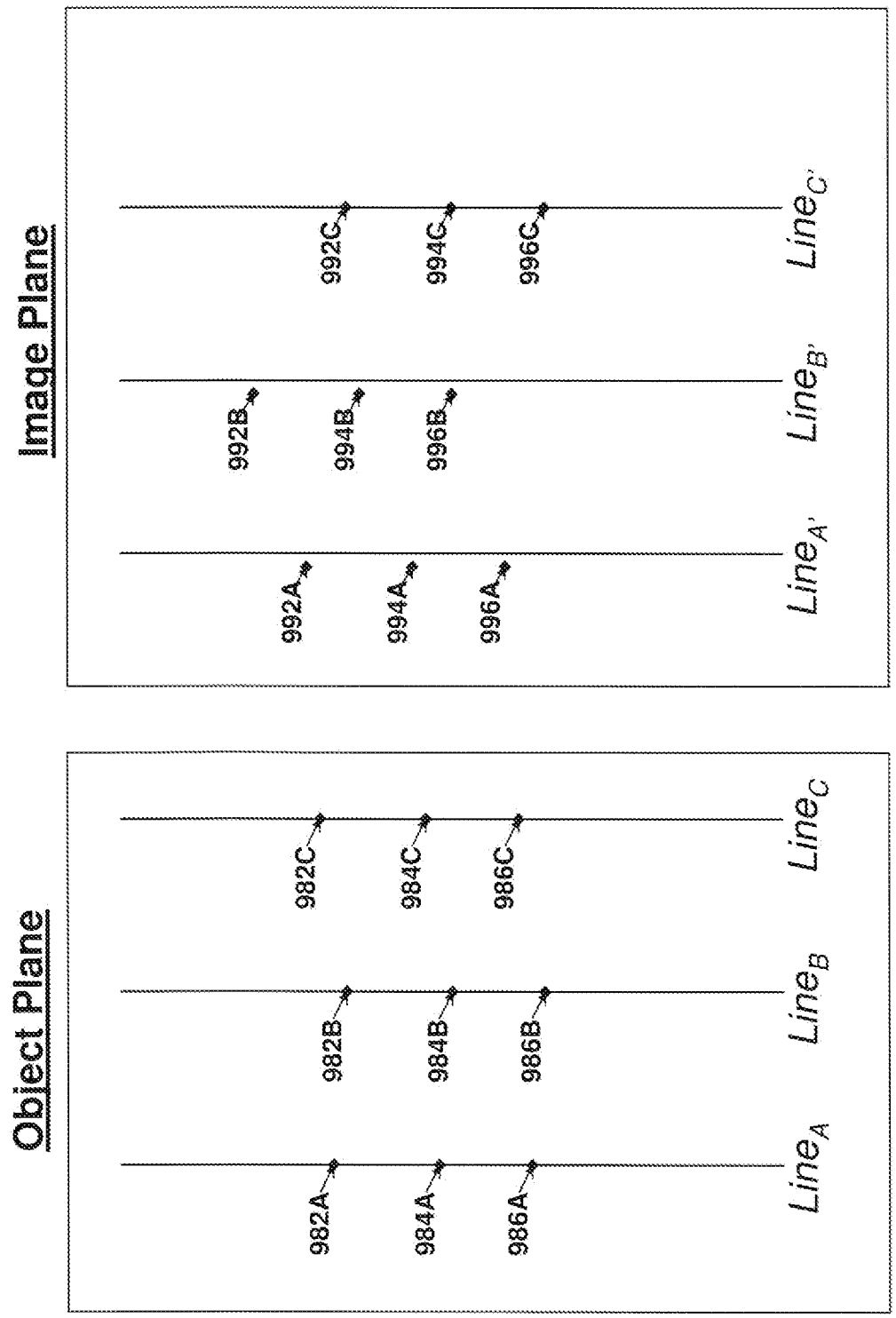

However, it is noted the light from multiple points along a line in the object-plane may reach a since point in the image-plane. Referring to FIG. 14B, it is noted that light from all of points 982A, 984A and 986A may reach point 992A. Light from all of points 982A, 984A and 986A may reach point 992B. Light from all of points 982B, 984B and 986B may reach point 992B.

Feature B—for each given point along each given line of the set of parallel lines in the image plane, light of only a single wavelength from multiple locations along the corresponding line in the object plane reaches the given point of the given line.

Figure 15A:
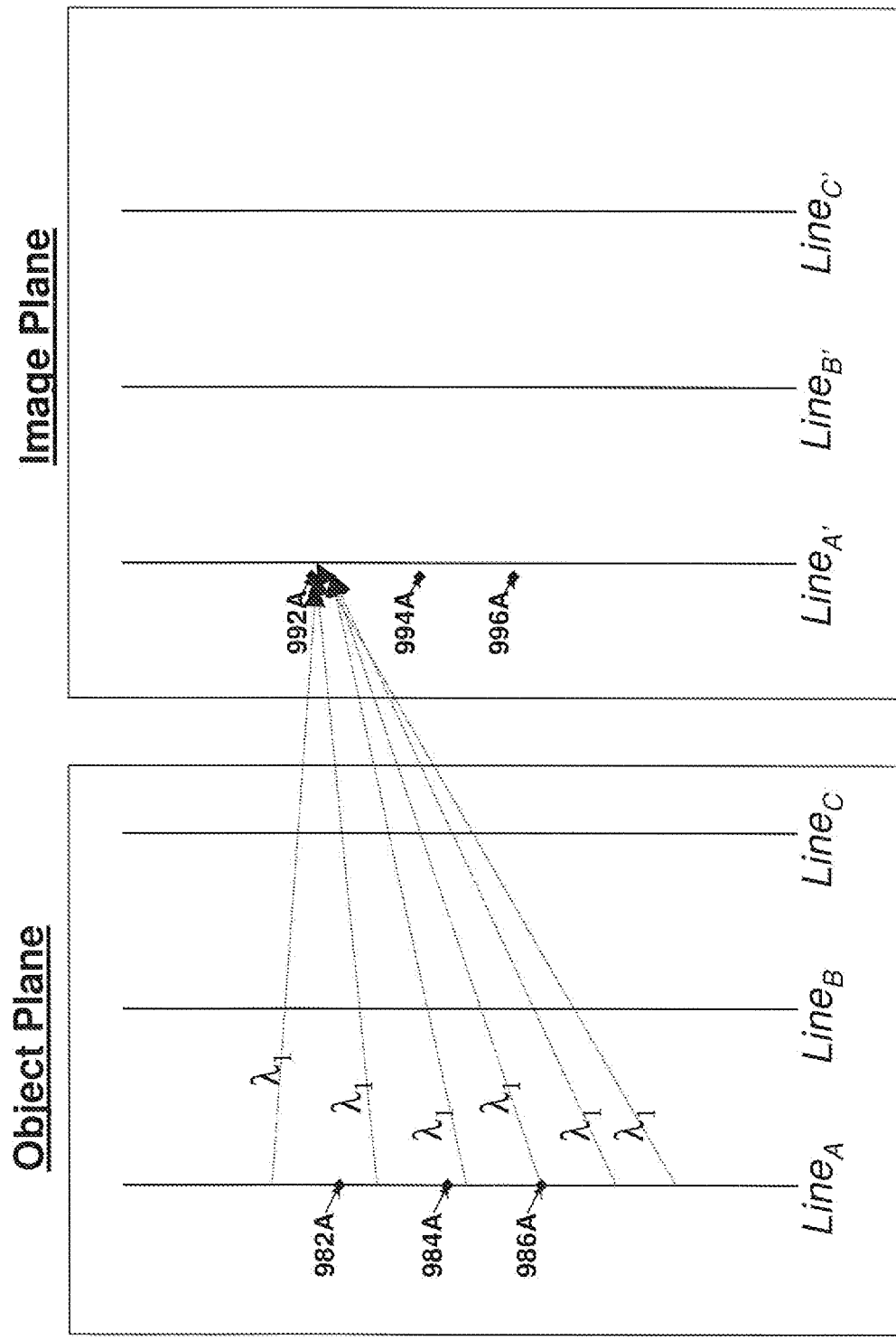

Thus, referring to FIG. 15A, light of wavelength $\lambda_1$ from a variety of locations along line A reaches the single point 992A—only light of a single wavelength $\lambda_1$ reaches point 992A.

Figure 15B:
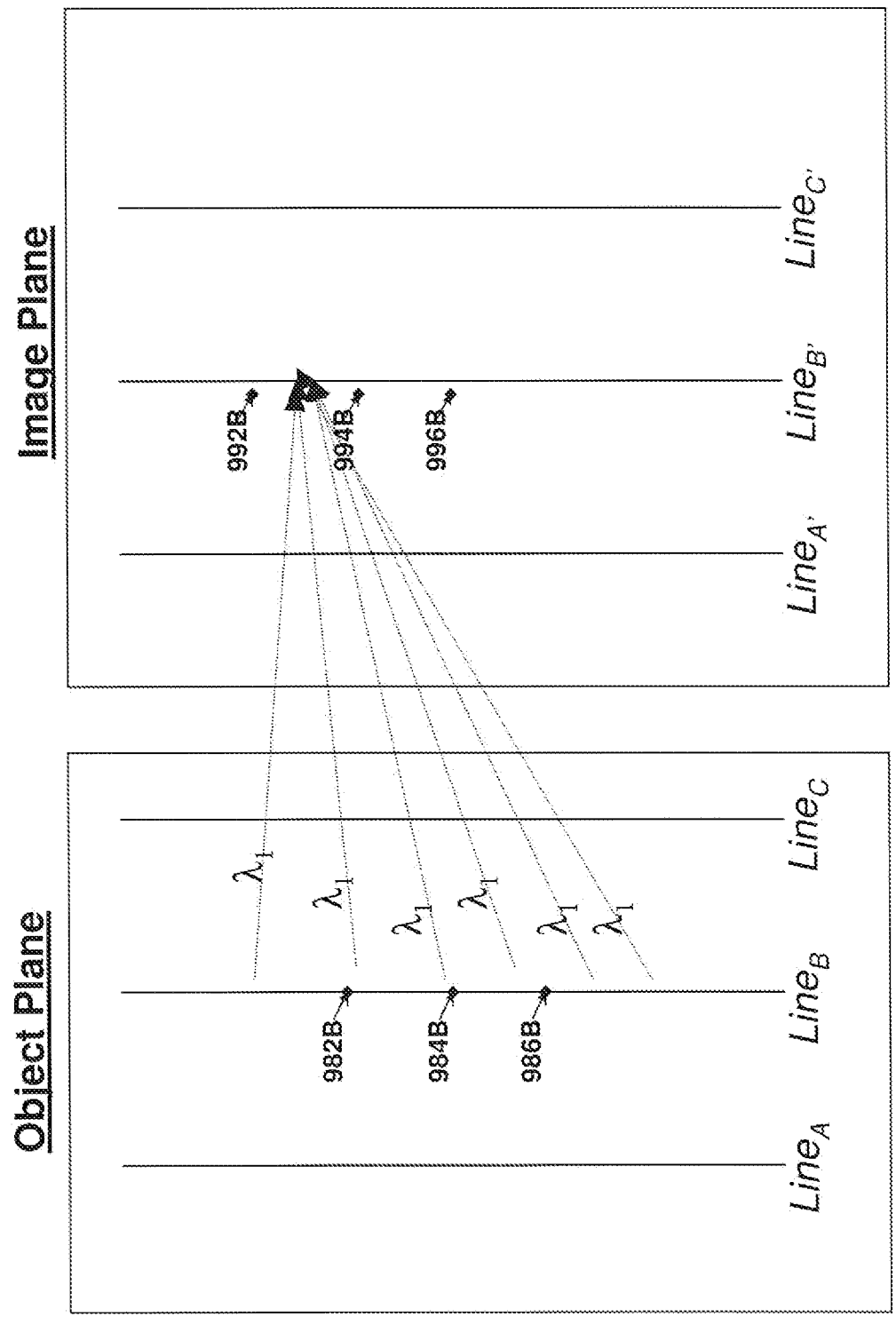

Referring to FIG. 15B, light of wavelength $\lambda_2$ from a variety of locations along line A reaches the single point 994A—only light of a single wavelength $\lambda_2$ reaches point 992A.

Figure 16A:
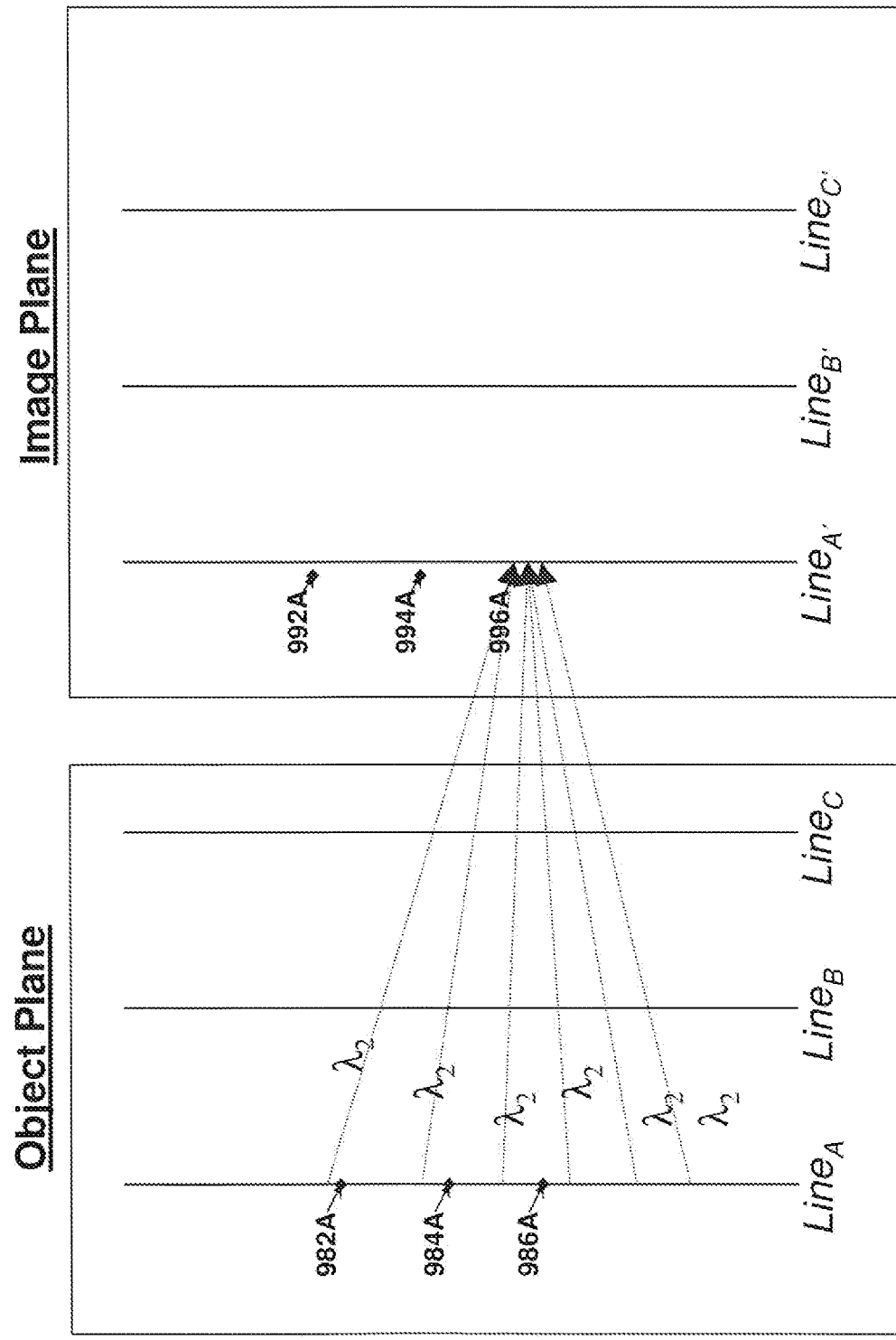
FIG. 16C illustrates object-plane-projected regions (e.g. elongated areas of the object-plane) formed by projecting regions of space into the object plane.
Figure 16B:
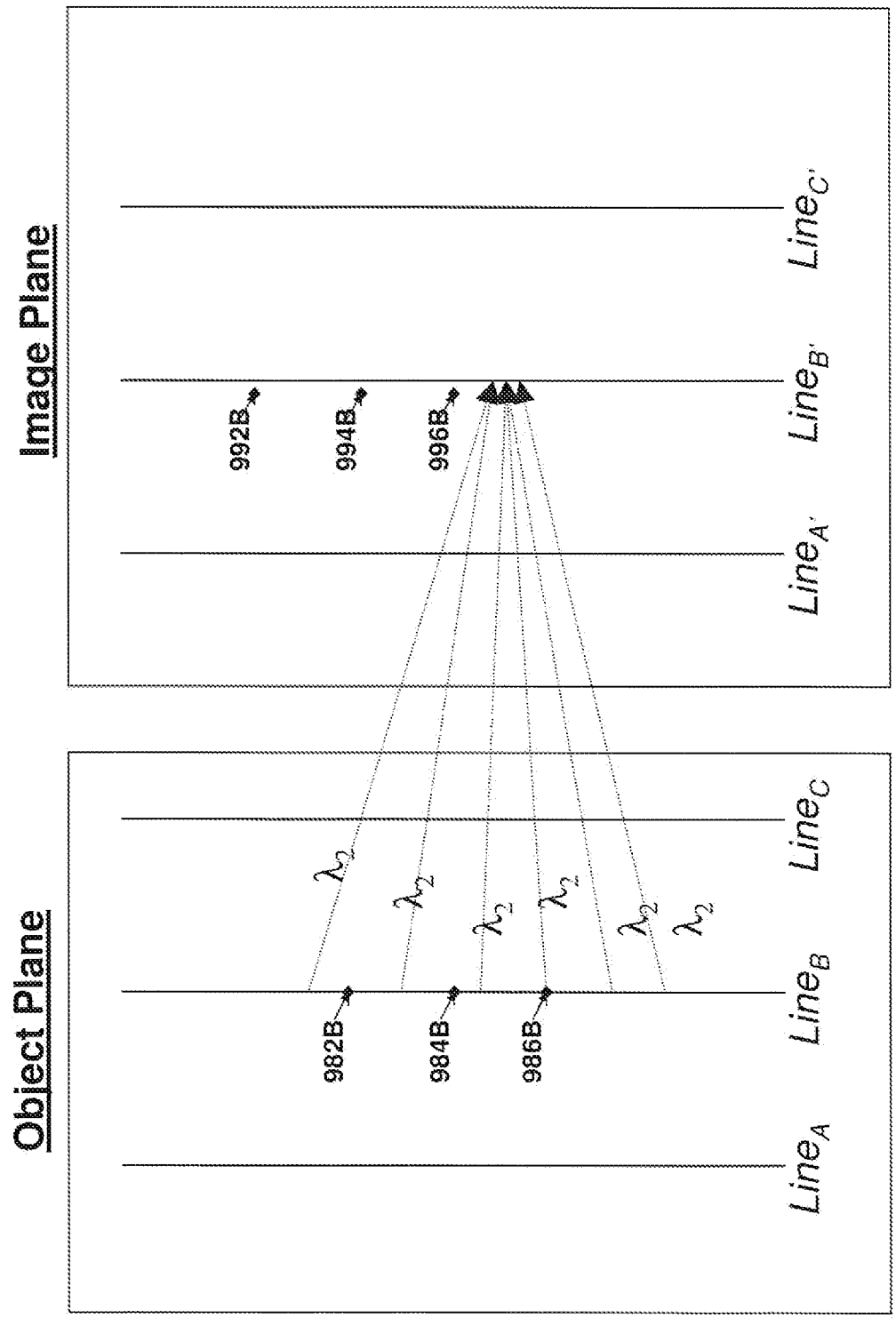

Similarly, FIGS. 16A-16B relate to lines B and B'.

Feature C—

In some embodiments, along a line of the image plane, the wavelength of light from the object plane monotonically increases—thus, a wavelength of light received at point 994B would exceed the wavelength of light received at point 992A, a wavelength of light received at point 994C would exceed the wavelength of light received at point 992B, and so on—in moving in a single direction (i.e. down) the light wavelength monotonically increases.

Figure 16C:
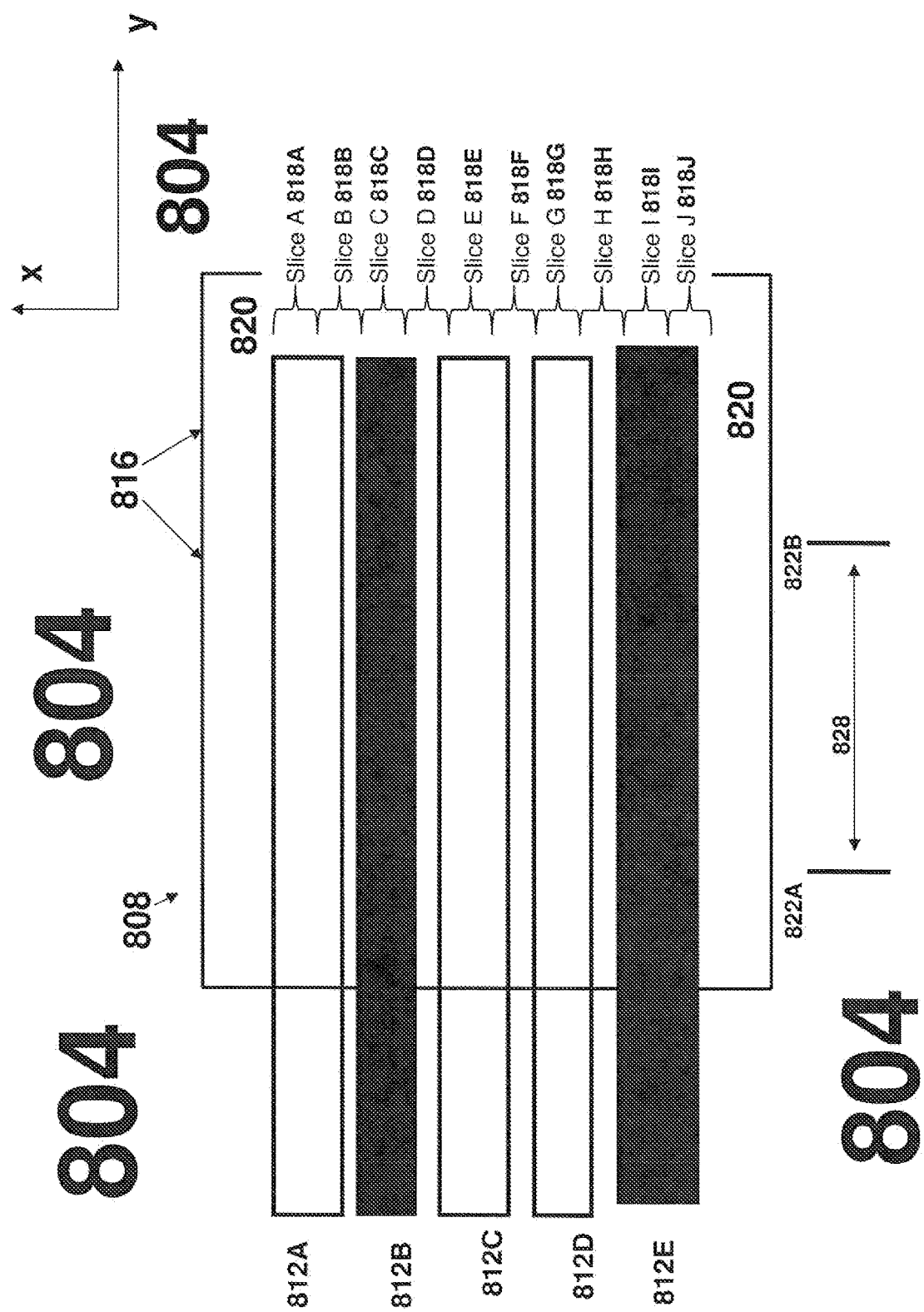

Discussion of FIG. 16C

As a result of the optics, the of each 'region' may be relatively long and thin, Thus, when each region of space is projected into the object plane, a respective 'projected region' is form. As shown in FIG. 16C, these object-plane-projected regions may be long and thin—e.g. having an aspect ratio of at least 5, and defining elongate axes (i.e. along the length of each object-plane-projected-region) that are all aligned with each other.

In FIG. 16, the object-plane-projected regions are informally referred to as 'slices' of the object plane. The length of each slice is shown by 828 and the width is shown by the widths of 818A-818J—the object aspect ratio is the length the length 828 and the widths, and the elongate axis is along the y axis.

Thus, the elongate axis of slice A 818A is along the y axis, the elongate axis of slice B 818B is along the y axis, and so on.

Thus, in FIG. 16C, the area which along the y axis are between locations 822A and 822B and along the x axis within the 'slice A' 818A' is a first elongated area of the object-plane—the 'elongate axis' of this first elongated area is along the y axis, and an aspect ratio of this elongated area is clearly at least 5 or at least 10. This first elongated area is entirely within white shaft 812A. This first elongated area is formed by the perpendicular projection of a three-dimensional region (e.g. for which a spectrum is measured) into the object-plane.

Similarly, a second elongate area is formed by Slice B 818B, a third elongate region is formed by Slice C 818C. All of these elongated areas are formed by respectively projecting a respective region of space into the object-plane. All of these elongated areas have an 'elongate axis' (i.e. along the longer length) that is along the y axis.

Figure 17A:
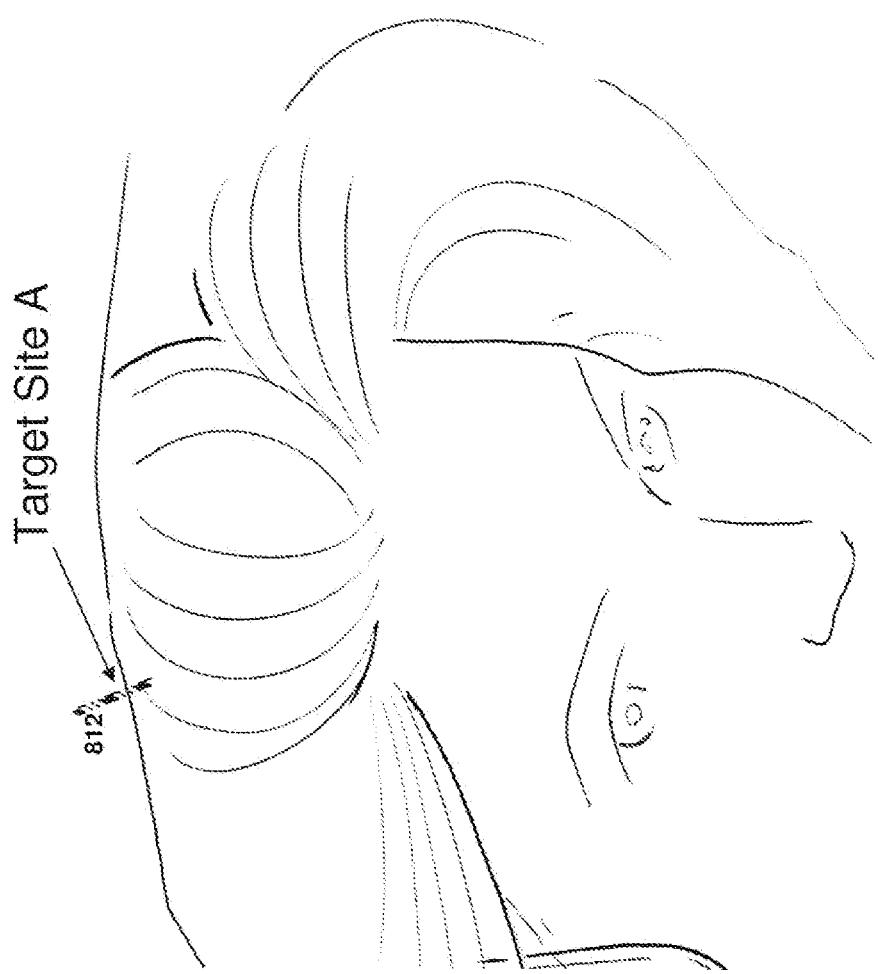
FIGS. 17-27 illustrate additional embodiments.

Discussion of FIGS. 17A-17B

In some embodiments, hair may be optically probed (e.g. to acquire spectral and/or reflection data thereof) in-situ. In this case, the hair-reader may be oriented in a generally 'downward' orientation where the user's hair is 'below' (i.e.

in terms of height/altitude') window 808. This is illustrated in FIGS. 17B-17B where hair at 'target site A' is optically probed.

Discussion of FIGS. 18-27

Figure 18:
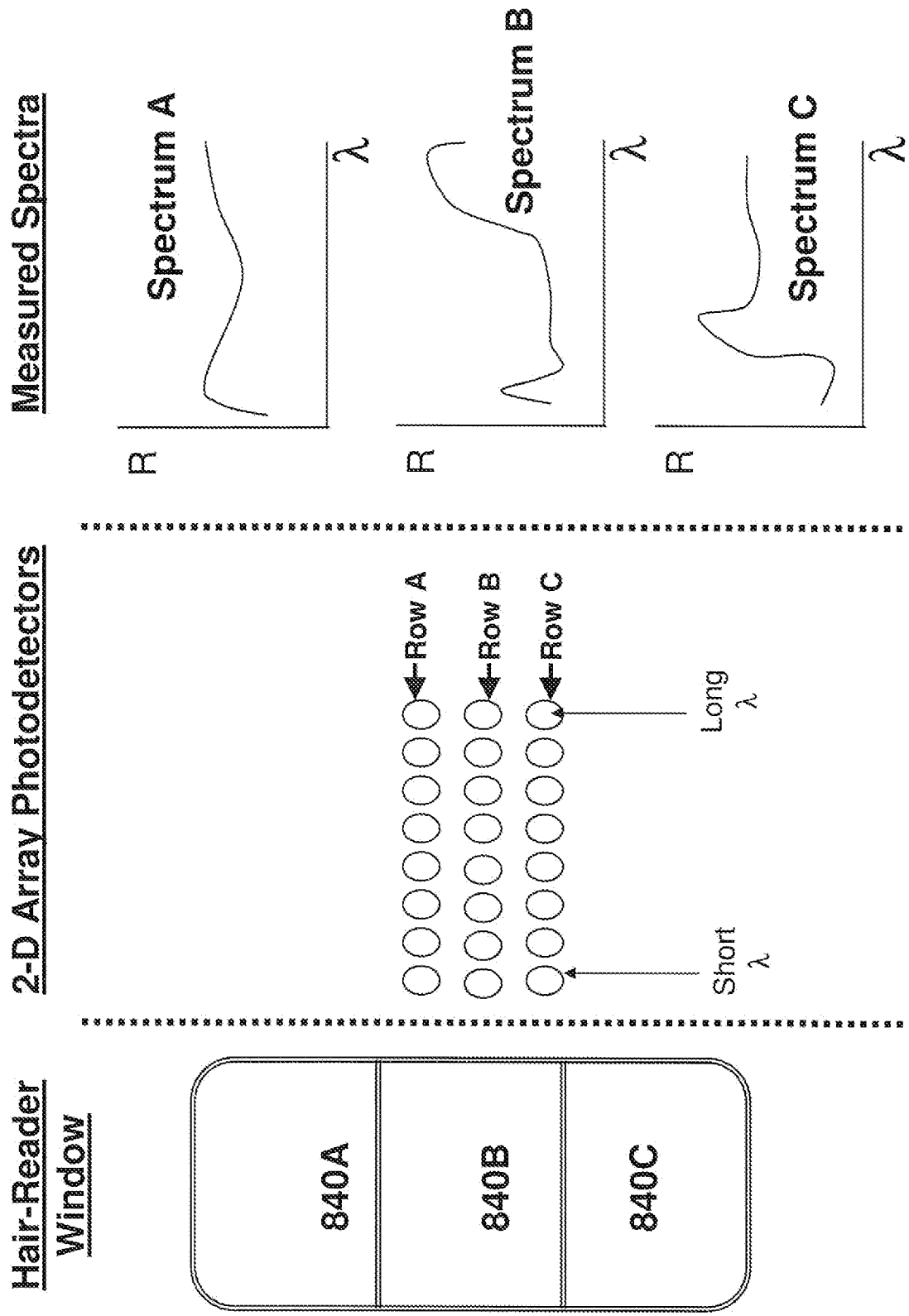

As illustrated in FIG. 18, (i) Row A of the 2D-array of photodetectors 180 is used to record spectroscopic data of keratinous fiber(s) within slice 840A; (ii) Row B of the 2D-array of photodetectors 180 is used to record spectroscopic data of keratinous fiber(s) within slice 840B; (iii) Row C of the 2D-array of photodetectors 180 is used to record spectroscopic data of keratinous fiber(s) within slice 840C. Examples of such spectrum are illustrated in the right-hand column of FIG. 12.

Figure 19:
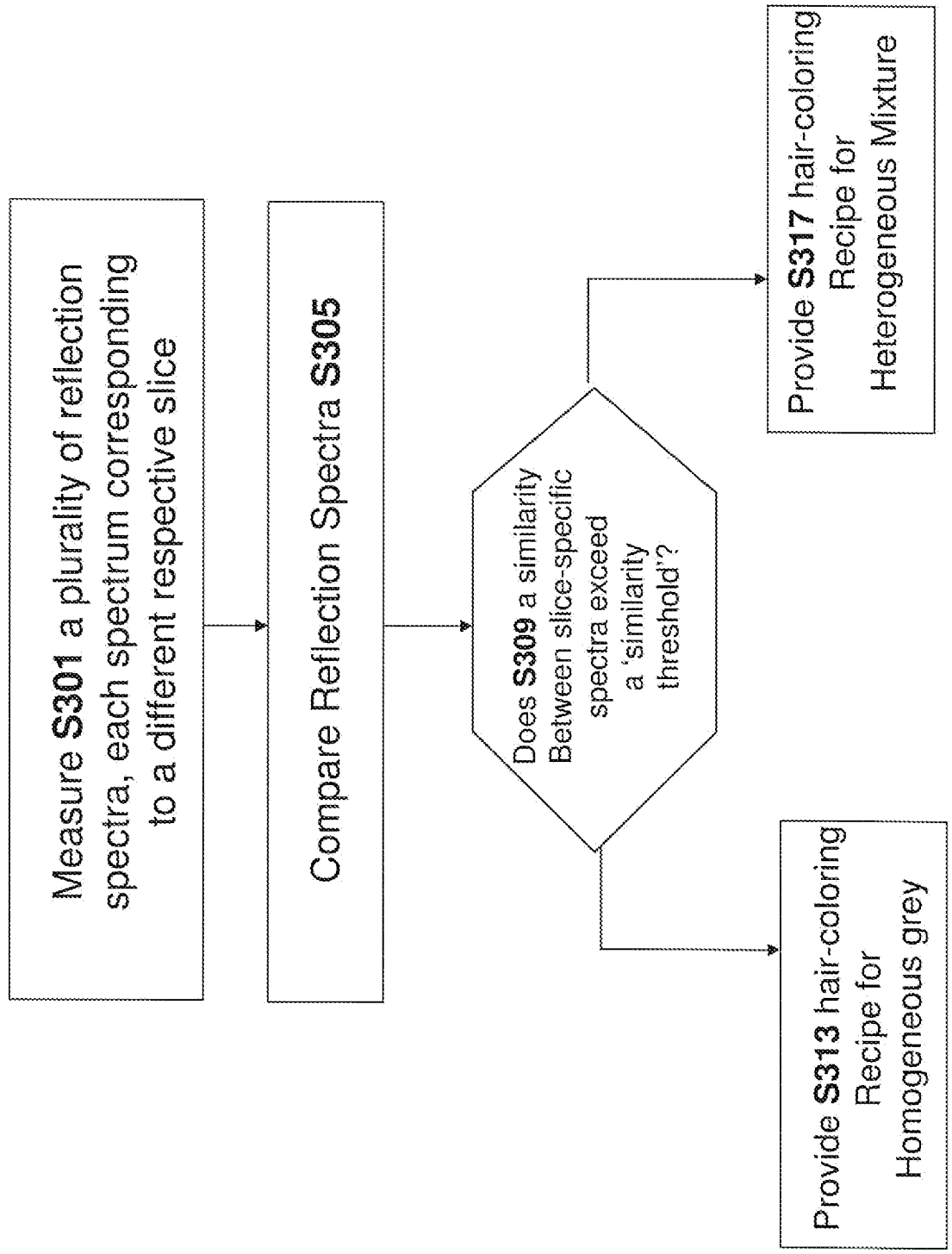

FIG. 19 is a flow chart of a technique for computing a hair-coloring recipe and/or for dispensing hair-coloring agents. In step S301, a plurality of reflection spectra are measured, each spectrum corresponding to a different respective slice—e.g. a first spectrum that is specific to hair shaft(s) within slice 840A, a second spectrum that is specific to hair shaft(s) within slice 840B, and a third spectrum that is specific to hair shaft(s) within slice 840C.

In step S309, the slice-specific spectra are compared with each other, and a parameter descriptive of similarity of multiple spectra may be computed. For example, if the spectra are relatively similar to each other, a recipe S313 may be provided for 'homogenous grey'. Alternatively, if the spectra are less similar to each other, a recipe specific to a heterogeneous mixture of hair may be provided. Hair-coloring agents may be dispensed according to the computed hair-coloring recipes.

Figure 20A:
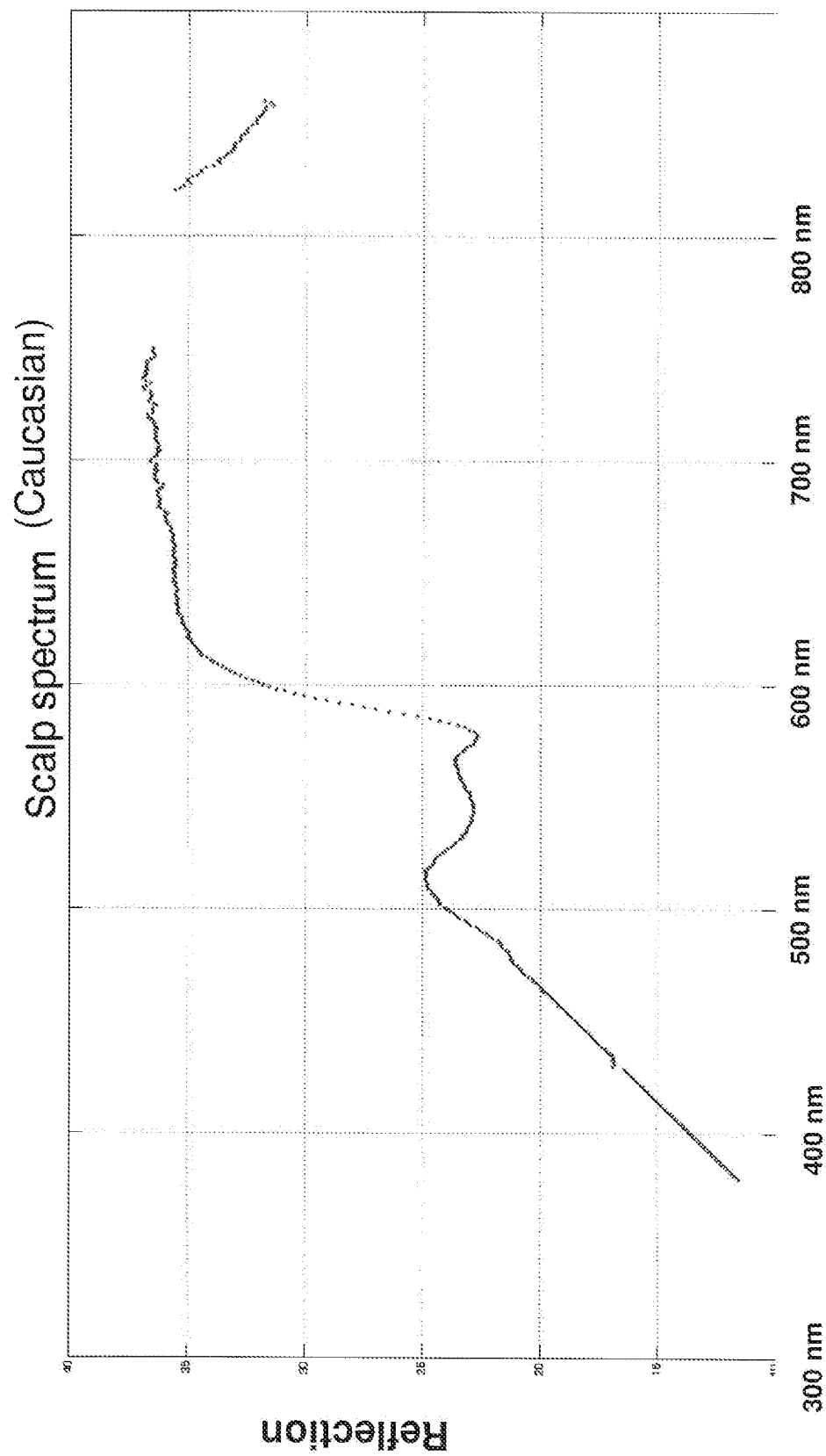
Figure 20B:
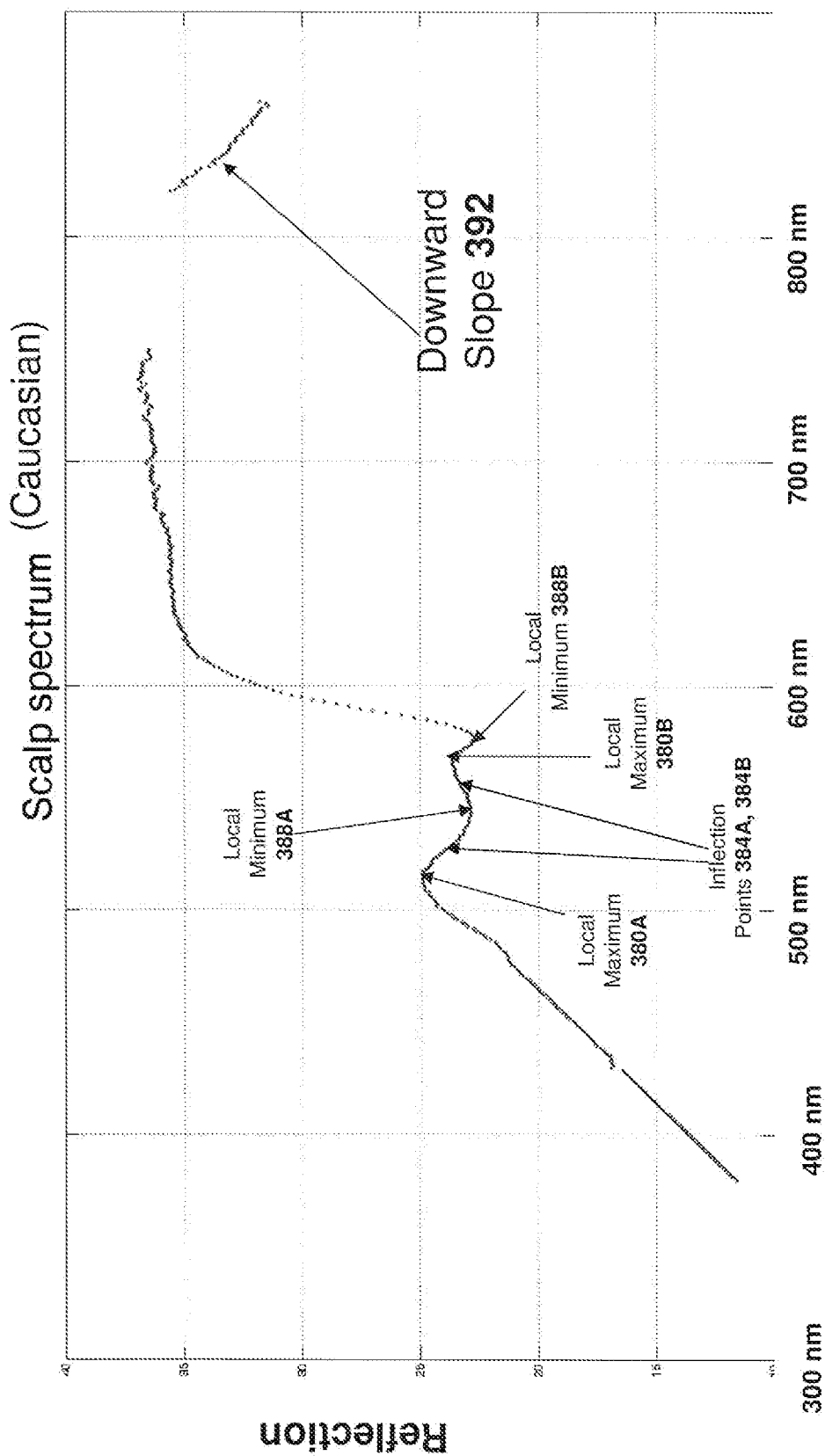

FIG. 20A illustrates a scalp reflection—e.g. a reflection spectra of skin on a user's scalp. FIG. 20BB illustrates the 'identifying features' of a scalp reflection spectrum including points where an Nth derivative (N is positive integer) are zero in the [500 nm, 580 nm] portion of the spectrum. Thus, in the example of FIG. 20B, local maxima 380, local minima 388, and inflection points 384 are illustrated.

In some embodiments, it is possible to analyze a spectrum (a) (e.g. reflection spectrum) of a user's hair (e.g. measured in step S105) to determine, in fact, the data thereof is entirely due to a user's hair, or if, in fact, there is any scalp-related contribution (and a magnitude thereof).

In some embodiments, it is possible to focus in on 'recognition features' that provide distinguishing power between hair-spectrum(a) and scalp spectrum(a). FIG. 20B relates to some 'recognition features.'

In some embodiments, when analyzing a measurement spectrum(a) to determine a relative magnitude of a contribution due to scalp, it is possible to assign extra weight and/or predictive power for one or more 'recognition features' including but not limited to: (i) a presence or absence of critical points and/or inflection points and/or points where higher-order derivatives are zero (or any other value): (ii) a number of such points in a portion of the spectrum (iii) a distance between such points; (iv) a value of a slope (or higher-order derivative) in a portion of the spectrum [e.g. a downward slope 392—e.g. monotonically downward between about 820 nm and about 860 nm or other features or combinations thereof.

Figure 21:
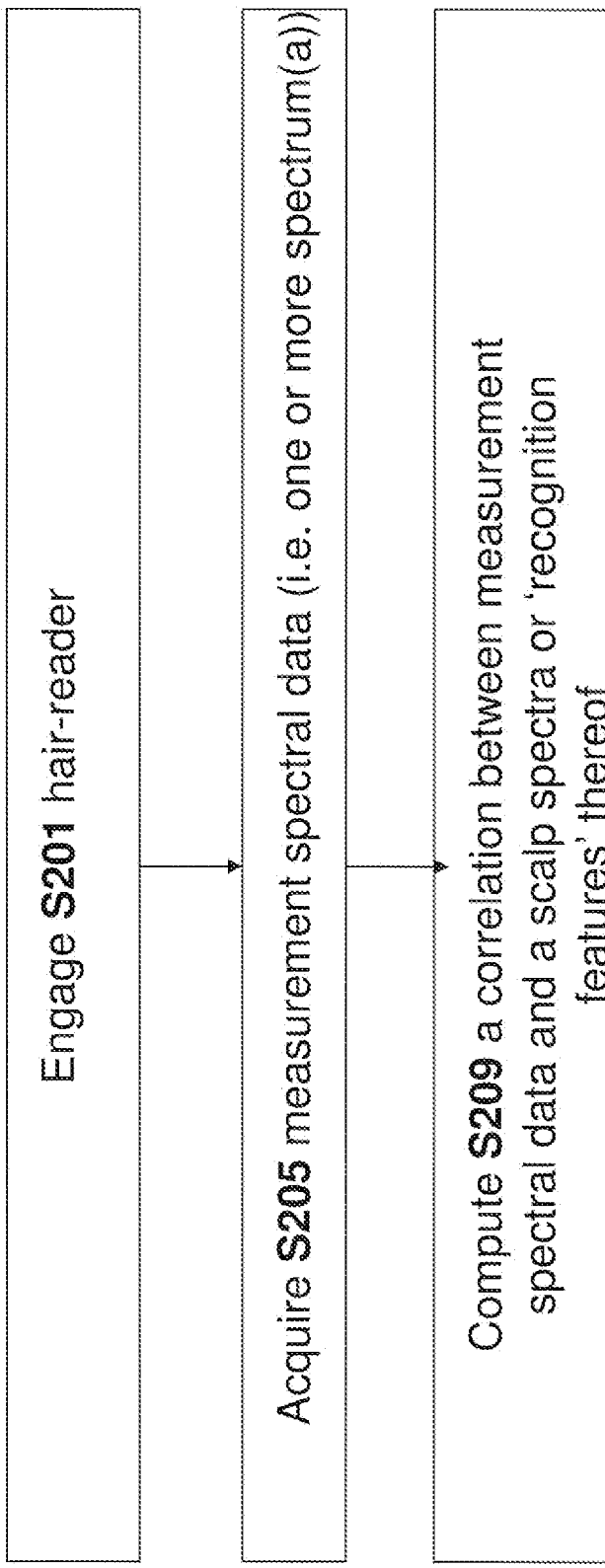
Figure 22:
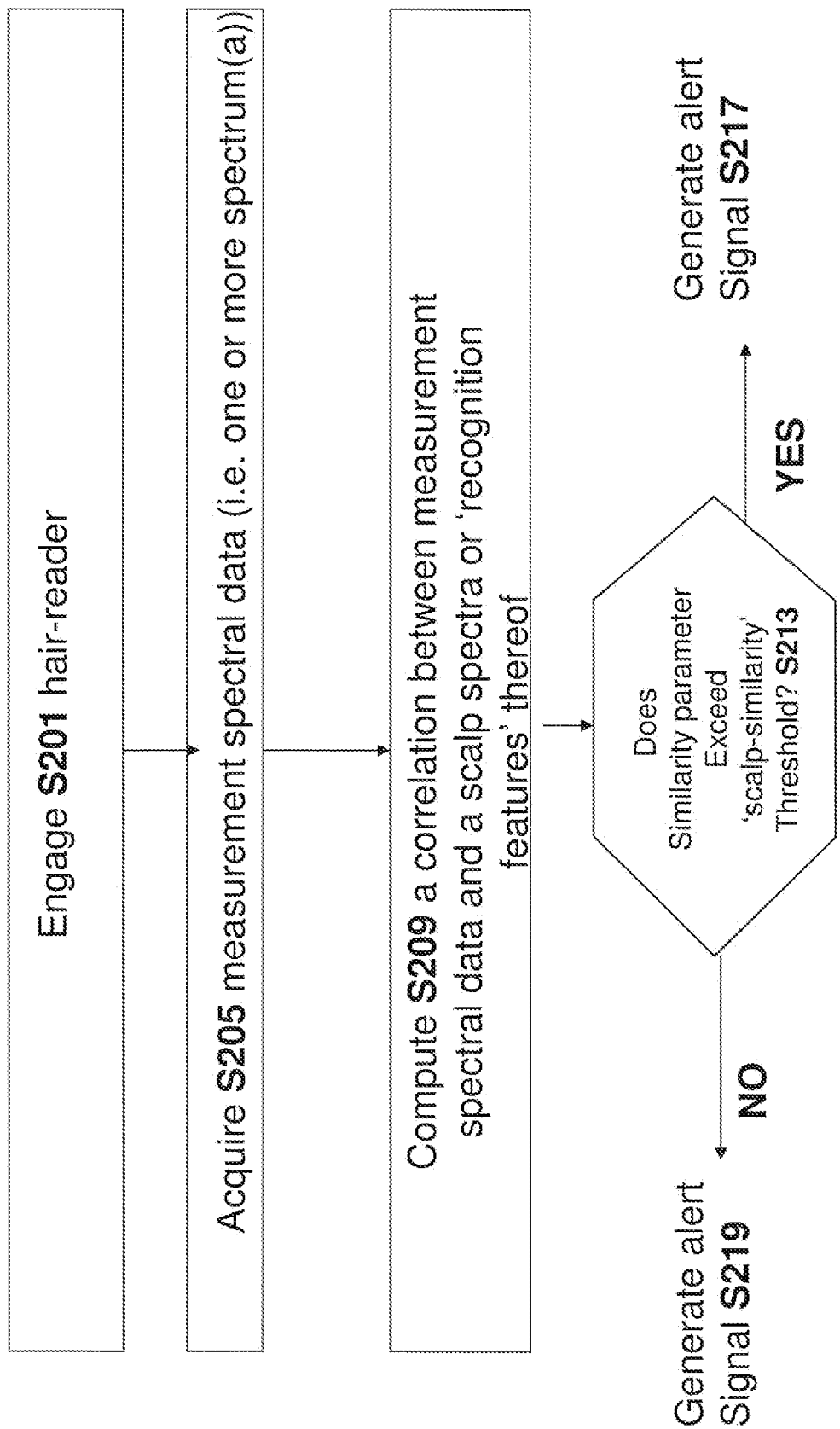
Figure 23:
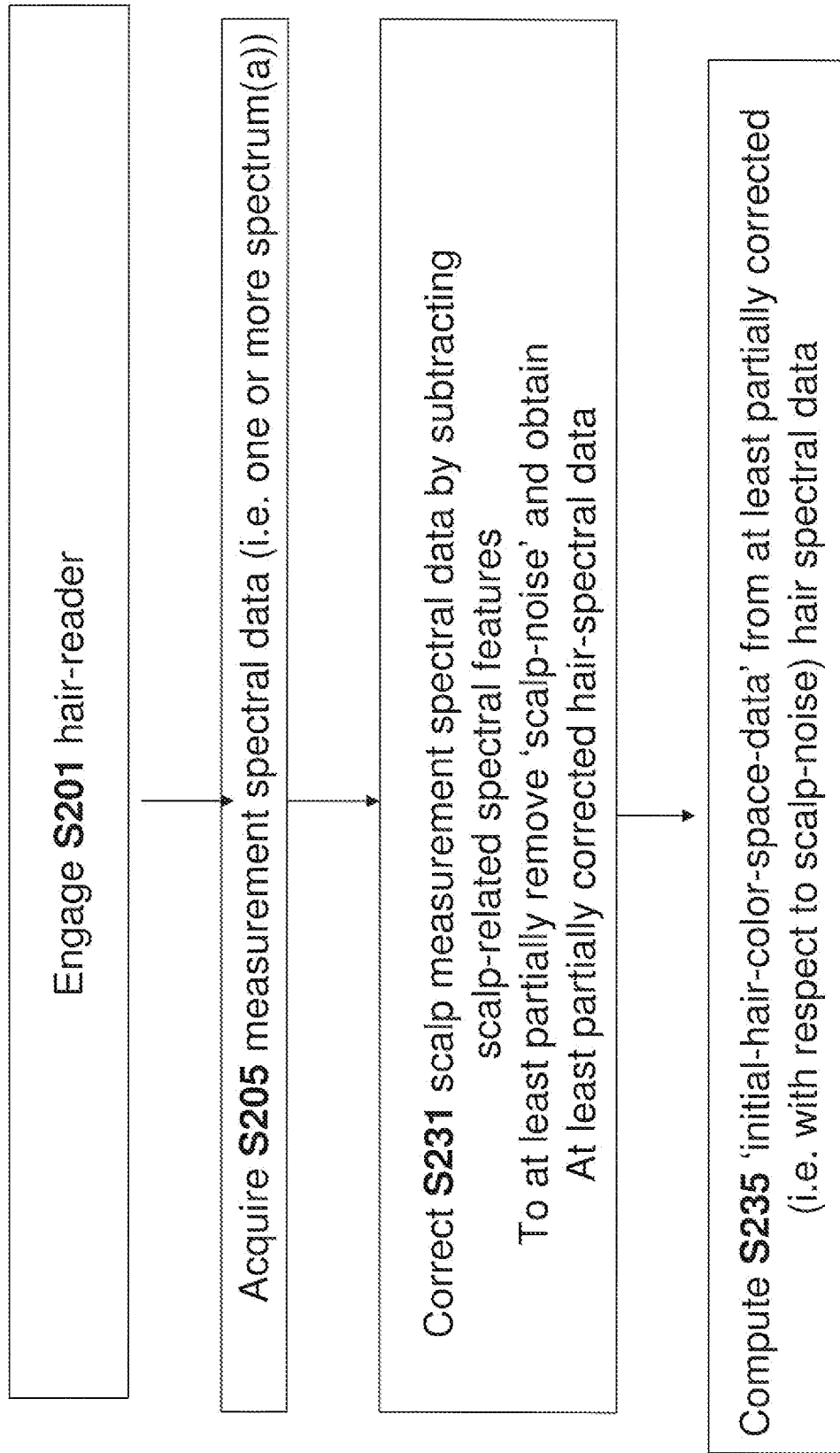

Thus, in FIG. 21, it is possible to measure a correlation between measurement spectral data and one or more scalp 'recognition features.' (step 209).

Scalp-spectrum data may be pre-stored in computer storage (e.g. volatile and/or volatile storage). The scalp-spectrum data may be universal, population-specific (e.g. race-specific), and/or user-specific—e.g. in FIG. 26 it is possible (target site C) to explicitly measure spectral data of a user's scalps.

There are a number of possible responses to the scalp-spectrum correlation measurement of step S209. In one example (FIG. 22), it is possible to generate an alert signal (e.g. audio alert, visual alert, email alert, etc) contingent upon a measurement spectrum(a) exhibiting similarity beyond a threshold value. Alternatively or additionally (FIG. 19), the similarity between a measurement spectra and one or more features of a scalp may be used to correct measurement data to remove scalp-related noise.

Figure 24:
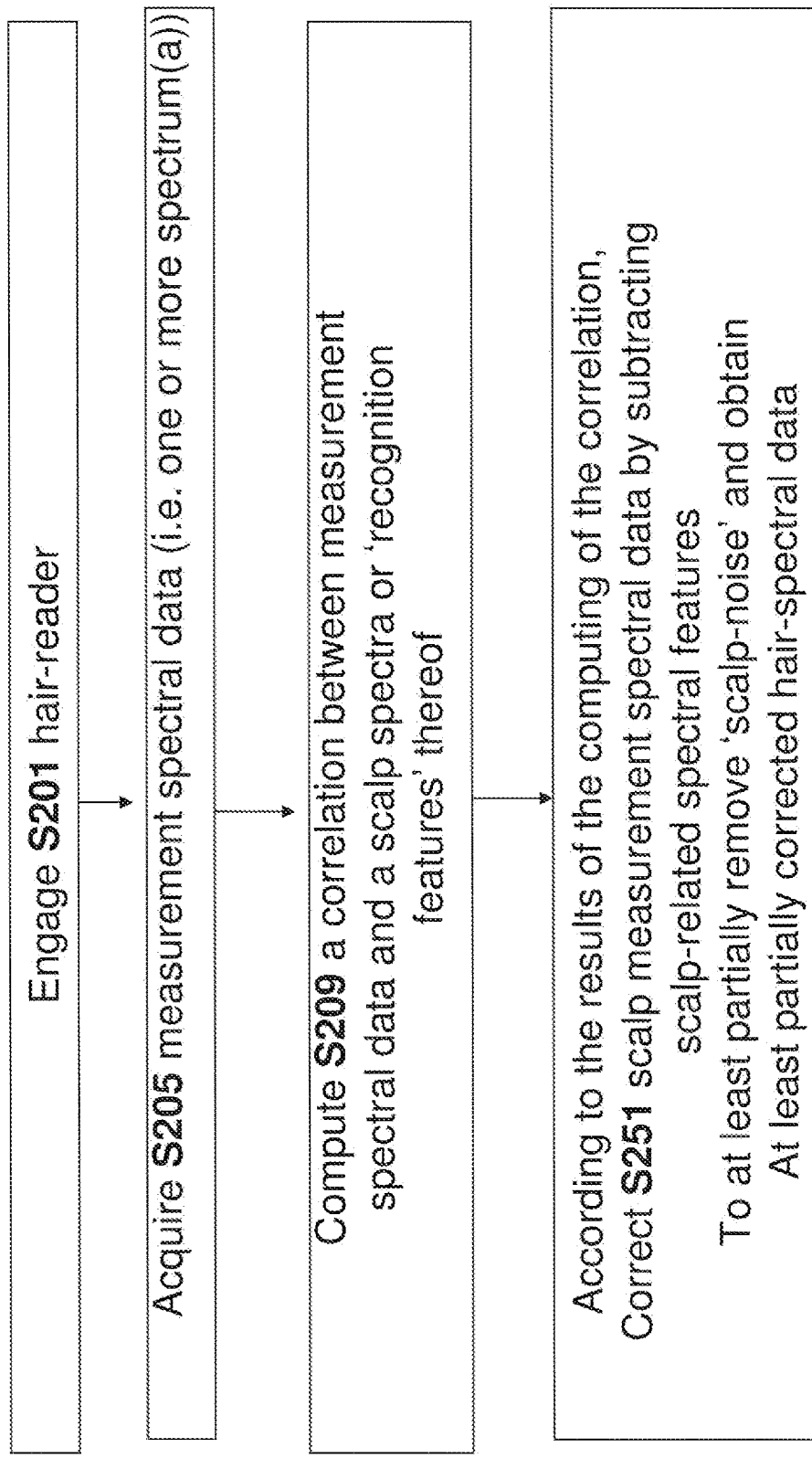
Figure 25A:
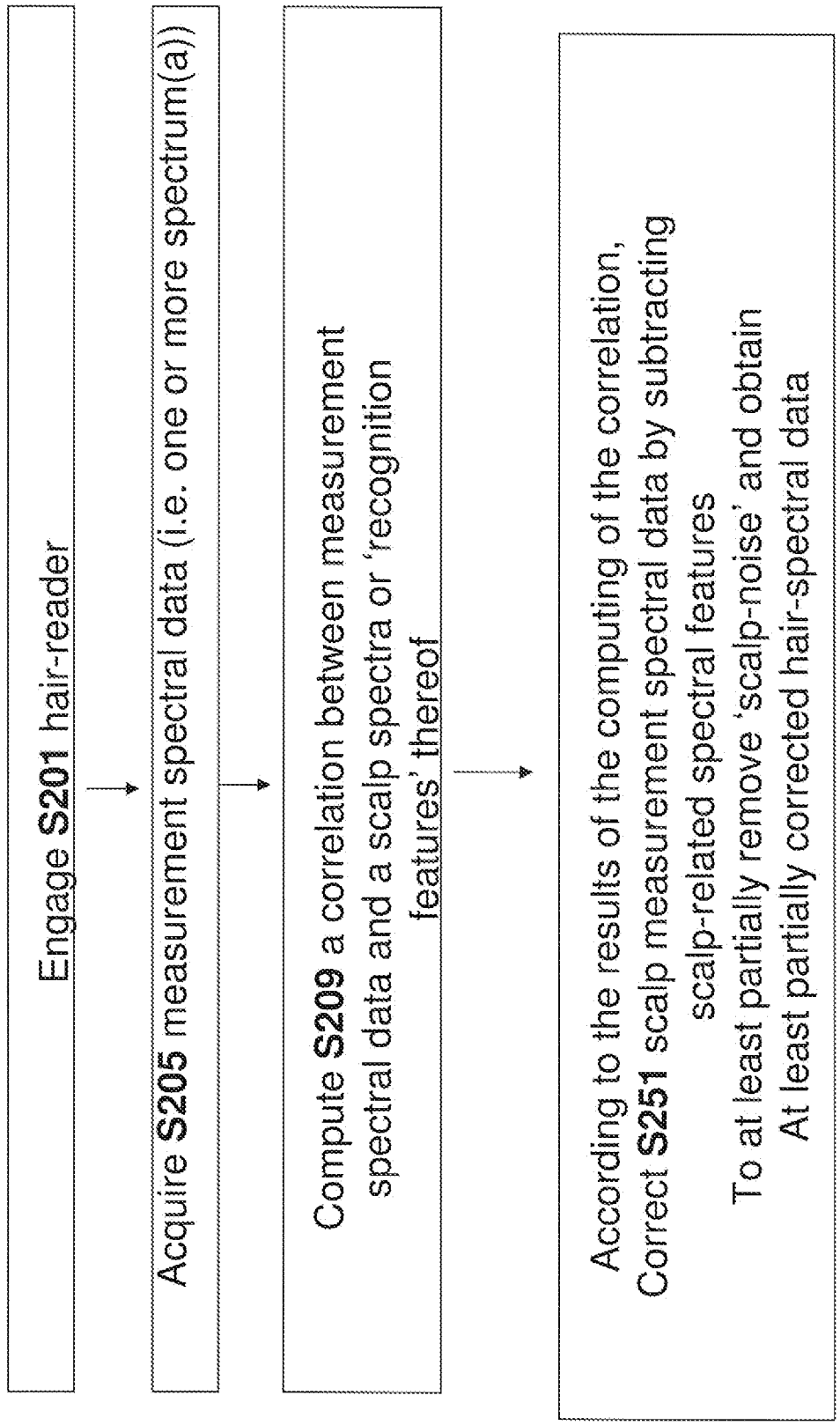
Figure 25B:
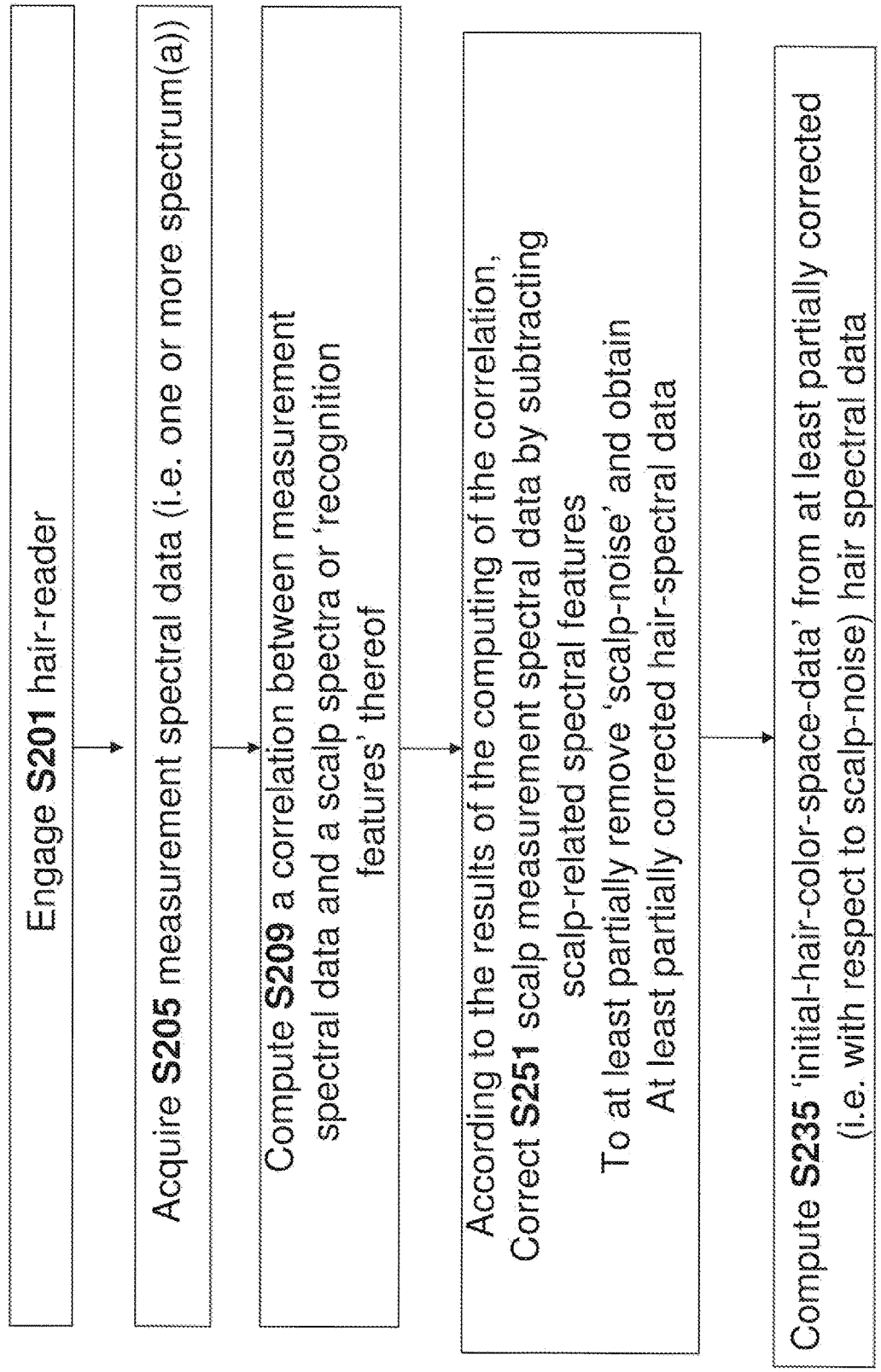
Figure 26:
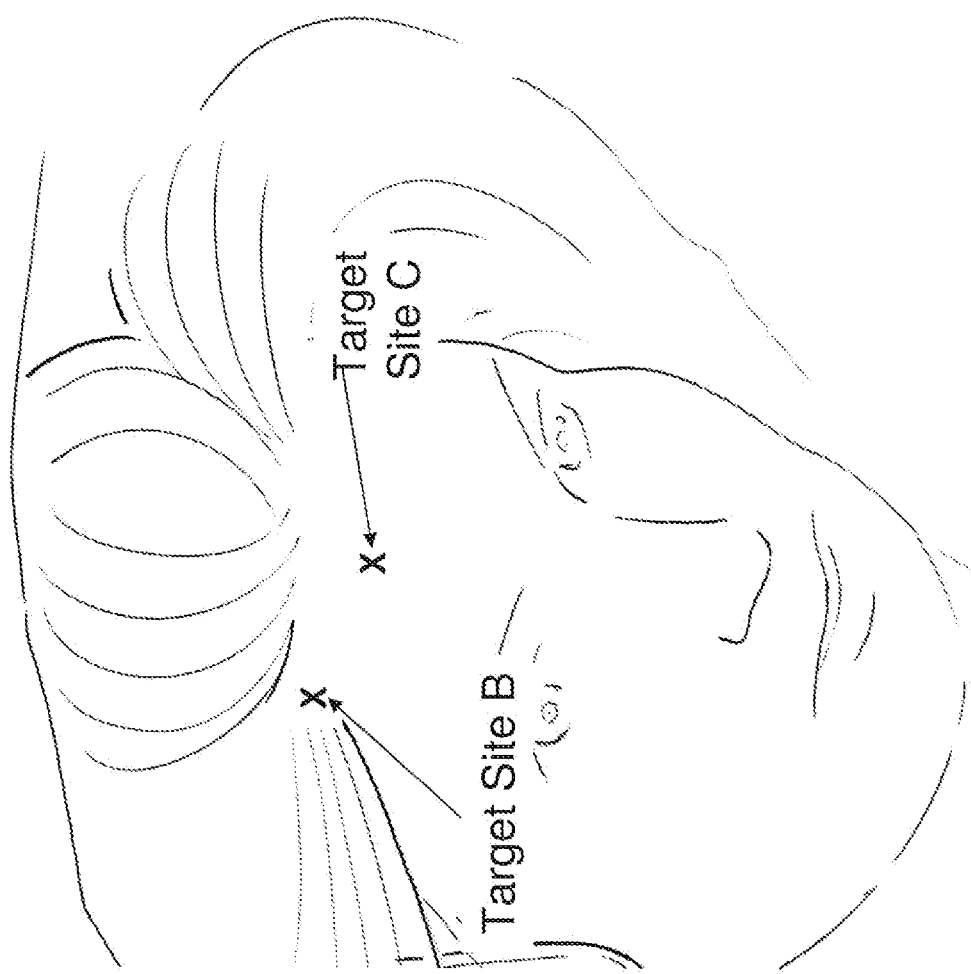

In FIG. 24, scalp-related noise may be removed in step S251.

It is not always clear a-priori how much influence scalp has upon a user-measurement, and thus it is not always clear a-priori what 'magnitude' or 'coefficient' of a scalp spectrum or portion thereof (e.g. pre-stored) may be applied to the scalp spectrum when subtracting off scalp-spectrum data (in step S251) from measurement data. This problem is addressed in FIGS. 25A-26B.

Figure 27:
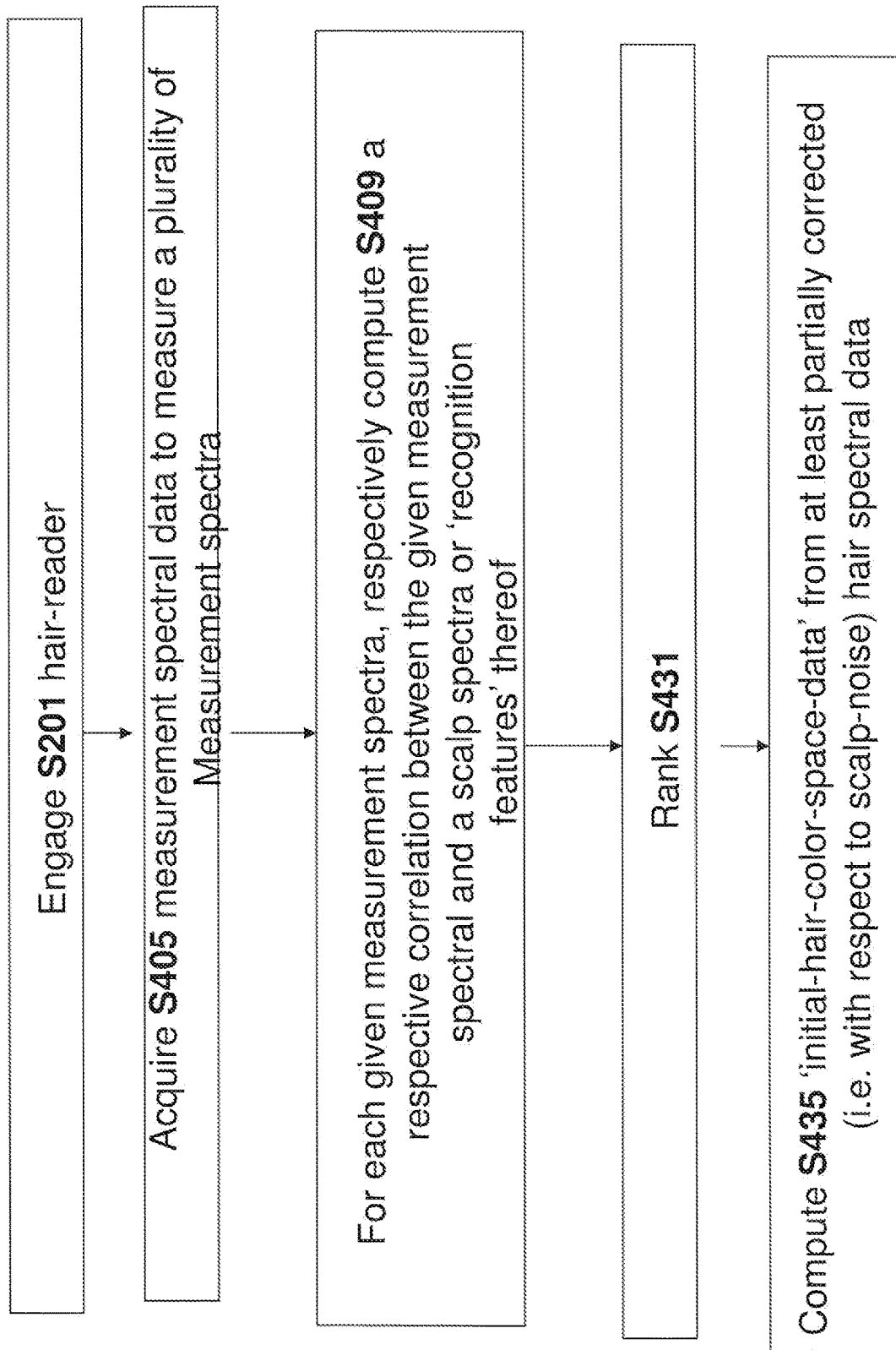

FIG. 27 relates to the situation where a plurality of spectra of measured—e.g. using any technique disclosed herein (see, e.g. FIGS. 5-13). In this case, for each of the spectra it is possible to measure a respective strength of correlation, and when computing an initial hair-color value (e.g. in LAB space), to use the spectra having the least amount of 'scalp noise' therein.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

All references cited herein are incorporated by reference in their entirety. Citation of a reference does not constitute an admission that the reference is prior art.

The articles "a" and "an" are used herein to refer to one or to more than one. (i.e., to at least one) of the grammatical object of the article. By way of example, "an element" means one element or more than one element.

The term "including" is used herein to mean, and is used interchangeably with, the phrase "including but not limited" to.

The term "or" is used herein to mean, and is used interchangeably with, the term "and/or," unless context clearly indicates otherwise.

The term "such as" is used herein to mean, and is used interchangeably, with the phrase "such as but not limited to".

Having thus described the foregoing exemplary embodiments it will be apparent to those skilled in the art that various equivalents, alterations, modifications, and improvements thereof are possible without departing from the scope and spirit of the claims as hereafter recited. In particular, different embodiments may include combinations of features other than those described herein. Accordingly, the claims are not limited to the foregoing discussion.

What is claimed is:

1. A method of predicting a result of a hair-color-modifying treatment on a sample of hair, the method comprising:
   a) for each given region of a plurality of distinct regions, respectively measuring a region-specific spectrum of respective material of the hair-sample respectively disposed within the given region to obtain a plurality of measured region-specific spectra; and
   b) computing first and second predicted post-treatment spectra respectively from first and second initial spectra by respectively predicting a transformation of the first and second initial spectra following subjecting the sample of hair to the hair-color-modifying treatment, the first and second initial spectra being distinct and (i) derived from the plurality of measured region-specific spectra and/or (ii) corresponding to first and second instances of the plurality of measured region-specific spectra, the method further comprising:

computing from the first and second predicted post-treatment spectra, a predicted sample-representative post-treatment spectrum representing a predicted spectrum for the entire sample of hair after subjecting to the hair-color-modifying treatment, wherein the predicted sample-representative post-treatment spectrum is further computed in accordance with a hair-shaft color-heterogeneity parameter of the hair-sample which describes relative fractions of natural white shafts and natural-pigmented shafts within a sample of natural gray hair.

2. The method of claim 1 wherein:

the hair-sample is a sample of natural-gray hair that is a mixture of natural white shafts and natural-pigment-containing shafts;

each measured region-specific spectrum of a first set of the measured region-specific spectra is generated primarily by light scattered from natural white shaft(s);

each measured region-specific spectrum of a second set of the measured region-specific spectra is generated primarily by light scattered from natural-pigment-containing shaft(s);

the first and second initial spectra are respectively representative of the first and second set of spectra and are respectively derived therefrom.

3. The method of claim 1 wherein the hair-sample is a sample of formerly natural-gray hair that:
  (A) was formerly mixture of natural white shafts and natural-pigment-containing shafts; and
  (B) is presently a mixture of shafts of first and second color-types that are respectively derived from the natural white and the natural-pigmented-containing shafts;

each measured region-specific spectrum of a first set of the measured region-specific spectra is generated primarily by light scattered from shaft(s) of the first color-type;

each measured region-specific spectrum of a second set of the measured region-specific spectra is generated primarily by light scattered from shaft(s) of the second color-type; and the first and second initial spectra are respectively representative of the first and second set of spectra and are respectively derived therefrom.

4. The method of claim 1 wherein multiple region-specific spectra are compared to each other, and the predicted sample-representative post-treatment spectrum is computed according to the results of the comparing of the region-specific spectra.

5. The method of claim 1 wherein a different predicted sample-representative post-treatment spectrum is respectively computed for each candidate hair-color-modifying treatment of a plurality of candidate hair-color-modifying treatments, and wherein a recommended hair-color-modifying treatment is obtained upon comparing predictions for each of the candidate hair-color-modifying treatments.

6. The method of claim 1 further comprising computing a combination of ingredients for a hair-coloring composition in accordance with the sample-representative post-treatment spectrum, and dispensing the computed combination of ingredients.

7. The method of claim 1, wherein step (b) is performed respectively for each candidate hair-color-modifying treatment of a plurality of candidate hair-color-modifying treatments, and wherein a recommended hair-color-modifying treatment is obtained upon comparing predictions for each of the candidate hair-color-modifying treatments.

8. The method of claim 1, further comprising computing in a combination of ingredients for a hair-coloring composition in accordance with the predicted post-treatment spectra computed in step (b).

9. The method of claim 1 wherein each measured region-specific spectrum includes at least one reading in the [600+N*50 nm, 1000 nm] range, wherein N is an integer having a value of at least 1 or at least 2 or at least 3 or at least 4 or at least 5.

10. The method of claim 1 wherein each measured region-specific spectrum includes at least one reading in all of the following ranges: {[400 nm, 500 nm], [500 nm, 600 nm], [600 nm, 700 nm], [700 nm, 800 nm]}.

11. A method of optically acquiring data from a sample of hair by a measurement device defining object and image planes, the method comprising:
  a) disposing the hair sample so that the object plane passes through the sample of hair; and
  b) optically processing light reflected by hair of the sample of that, upon reaching the image plane:
    i) along each given line of a set of parallel lines in the image plane, only light from a corresponding line of a set of parallel lines in the object plane reaches the given line in the image plane;
    ii) for each given point along each given line of the set of parallel lines in the image plane, light of only a single wavelength from multiple locations along the corresponding line in the object plane reaches the given point of the given line; and
    iii) along each given line of the set of parallel lines in the image plane, the wavelength of light received from the object plane monotonically increases.

12. The method of claim 11, wherein the processed light is received by an array of photodetectors to detect one or more spectrum of the sample of hair or of a portion thereof.

13. The method of claim 11 performed to measure spectra as follows: for each given region of a plurality of regions, a respective region-specific spectrum of respective material of the hair-sample respectively disposed within the given region is measured.

14. The method of claim 13 wherein:

the sample hair is disposed so that the object plane passes through each of the regions;

a perpendicular projection of each region into the object plane yields a respective elongated area of the object-plane defining an elongate axis;

each elongated area defined by a projection of a respective region into the object plane has a respective aspect ratio equal to at least 5 or at least 10 and/or a respective width of each elongated area of the object plane is at most 100 microns or at most 50 microns or at most 25 microns or at most 15 microns; and all of the elongated axes are aligned with each other.

15. The method of claim 14, performed on a sample of hair-shafts that are aligned with each other to define an hair-alignment-axis, the hair-alignment axis being aligned with each of the elongate axes of the elongated areas.

16. Apparatus for predicting a result of a hair-color-modifying treatment on a sample of hair, the apparatus comprising:
   a) a spectrum-measuring device configured to measure a plurality of spectra as follows: for each given region of a plurality of distinct regions, respectively measuring a region-specific spectrum of respective material of the hair-sample respectively disposed within the given region to obtain a plurality of measured region-specific spectra; and
   b) electronic circuitry configured to compute first and second predicted post-treatment spectra respectively from first and second initial spectra by respectively predicting a transformation of the first and second initial spectra following subjecting the sample of hair to the hair-color-modifying treatment, the first and second initial spectra being distinct and (i) derived from the plurality of measured region-specific spectra and/or (ii) corresponding to first and second instances of the plurality of measured region-specific spectra,
   the electronic circuitry being further configured to:
   compute from the first and second predicted post-treatment spectra, a predicted sample-representative post-treatment spectrum representing the predicted spectrum for the entire sample of hair after subjecting to the hair-color-modifying treatment,
   wherein
   the predicted sample-representative post-treatment spectrum is further computed in accordance with a hair-shaft color-heterogeneity parameter of the hair-sample which describes relative fractions of natural white shafts and natural-pigmented shafts within a sample of natural gray hair.

17. The apparatus of claim 16 wherein the spectrum measuring device includes by color-dispersion optics.

18. The apparatus of claim 16 wherein the spectrum measuring device includes a hyperspectral device.

* * * * *

UNITED STATES PATENT AND TRADEMARK OFFICE
CERTIFICATE OF CORRECTION

PATENT NO. : 10,806,234 B2  
APPLICATION NO. : 15/303727  
DATED : October 20, 2020  
INVENTOR(S) : Efraim Miklatzky et al.

Page 1 of 1

It is certified that error appears in the above-identified patent and that said Letters Patent is hereby corrected as shown below:

On the Title Page

Item (63), Line 1-2, please delete "Continuation-in-part of application No. PCT/IL2014/050850, filed on Sep. 28, 2014.";

In the Claims

Column 35, Line 56, please change from "claim 1" to --claim 1,--;

Column 35, Line 61, please change from "claim 1" to --claim 1,--;

Column 36, Line 1, please change from "claim 1" to --claim 1,--; and

Column 36, Line 65, after "axes" please insert --of each of the elongated areas--.

Signed and Sealed this  
Twenty-second Day of June, 2021

Drew Hirshfeld  
*Performing the Functions and Duties of the*  
*Under Secretary of Commerce for Intellectual Property and*  
*Director of the United States Patent and Trademark Office*